US011234960B2

(12) United States Patent
Rinsch et al.

(10) Patent No.: US 11,234,960 B2
(45) Date of Patent: Feb. 1, 2022

(54) COMPOSITIONS AND METHODS FOR IMPROVING MITOCHONDRIAL FUNCTION AND TREATING NEURODEGENERATIVE DISEASES AND COGNITIVE DISORDERS

(71) Applicant: Amazentis SA, Lausanne (CH)

(72) Inventors: Christopher L. Rinsch, Lausanne (CH); William Blanco-Bose, La Croix (Lutry) (CH); Bernard Schneider, Pully (CH); Charles Thomas, Dijon (FR); Carmen Sandi, Bremblens (CH); Johan Auwerx, Buchillon (CH); Penelope Andreux, Eclepens (CH); Richardus Houtkooper, Weesp (NL); Eija Pirinen, Lausanne (CH); Laurent Mouchiroud, Morges (CH); David Genoux, Lausanne (CH)

(73) Assignee: Amazentis SA, Lausanne (CH)

( * ) Notice: Subject to any disclaimer, the term of this patent is extended or adjusted under 35 U.S.C. 154(b) by 585 days.

(21) Appl. No.: 14/644,912

(22) Filed: Mar. 11, 2015

(65) Prior Publication Data
US 2016/0213643 A1    Jul. 28, 2016

Related U.S. Application Data

(62) Division of application No. 13/336,841, filed on Dec. 23, 2011, now Pat. No. 9,872,850.

(60) Provisional application No. 61/426,957, filed on Dec. 23, 2010.

(51) Int. Cl.
| | |
|---|---|
| *A61K 31/366* | (2006.01) |
| *A23L 33/105* | (2016.01) |
| *A61K 36/185* | (2006.01) |
| *A61K 31/7048* | (2006.01) |
| *A61K 9/00* | (2006.01) |
| *A61K 31/352* | (2006.01) |

(52) U.S. Cl.
CPC .......... *A61K 31/366* (2013.01); *A23L 33/105* (2016.08); *A61K 9/0014* (2013.01); *A61K 9/0053* (2013.01); *A61K 9/0056* (2013.01); *A61K 31/352* (2013.01); *A61K 31/7048* (2013.01); *A61K 36/185* (2013.01); *A23V 2002/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,411,757 A * | 5/1995 | Buist | A23J 1/00 426/656 |
| 6,133,311 A | 10/2000 | Bok et al. | |
| 6,440,436 B1 | 8/2002 | Ghosal | |
| 9,872,850 B2 | 1/2018 | Rinsch et al. | |
| 10,028,932 B2 | 7/2018 | Rinsch et al. | |
| 10,485,782 B2 | 11/2019 | Rinsch et al. | |
| 10,857,126 B2 | 12/2020 | Rinsch et al. | |
| 2003/0078212 A1 | 4/2003 | Li et al. | |
| 2005/0282781 A1 | 12/2005 | Ghosal | |
| 2007/0184136 A1 | 8/2007 | Aviram | |
| 2008/0031862 A1 | 2/2008 | Ghosal | |
| 2008/0206275 A1 | 8/2008 | Ramazanov et al. | |
| 2008/0213401 A1 | 9/2008 | Smith | |
| 2008/0214656 A1 | 9/2008 | Lim et al. | |
| 2009/0246300 A1 | 10/2009 | Swilling | |
| 2009/0326057 A1 * | 12/2009 | Seeram | A61K 31/195 514/460 |
| 2010/0004334 A1 | 1/2010 | Jouni et al. | |
| 2010/0021533 A1 | 1/2010 | Mazed et al. | |

(Continued)

FOREIGN PATENT DOCUMENTS

| | | |
|---|---|---|
| CN | 101301319 A | 11/2008 |
| EP | 2033526 A1 | 3/2009 |
| EP | 2068864 A2 | 6/2009 |

(Continued)

OTHER PUBLICATIONS

Kaarniranta et al., Age-Related Macular Degeneration (AMD): Alzheimer's Disease in the Eye?, 2011, J Alzheimer's Disease, 24:615-631.*

(Continued)

*Primary Examiner* — Terry A McKelvey
*Assistant Examiner* — Catheryne Chen
(74) *Attorney, Agent, or Firm* — Foley Hoag LLP; Dana M. Gordon; Ila S. Anand

(57) ABSTRACT

Provided are compositions comprising compounds or precursors to compounds which may be used for a variety of therapeutic applications including, for example, treating and/or preventing a disease or disorder related to reduced or inadequate mitochondrial activity, including aging or stress, diabetes, obesity, and neurodegenerative diseases. The compounds relate generally to urolithins and precursors thereof, including but not limited to ellagitannins and urolithin A. In certain embodiments the compositions are presented in or as food products or nutritional supplements. These same compounds and compositions can also be used advantageously in generally healthy individuals to increase or maintain metabolic rate, decrease percent body fat, increase or maintain muscle mass, manage body weight, improve or maintain mental performance (including memory), improve or maintain muscle performance, improve or maintain mood, and manage stress.

21 Claims, 46 Drawing Sheets

Specification includes a Sequence Listing.

(56) References Cited

U.S. PATENT DOCUMENTS

| | | | |
|---|---|---|---|
| 2010/0055247 A1 | 3/2010 | Tirrito | |
| 2021/0059982 A1 | 3/2021 | Rinsch et al. | |

FOREIGN PATENT DOCUMENTS

| | | | |
|---|---|---|---|
| EP | 2654461 | A2 | 10/2013 |
| EP | 3278800 | A2 | 2/2018 |
| JP | H02304080 | A | 12/1990 |
| JP | 2008-503456 | A | 2/2008 |
| JP | 2010-280627 | A | 12/2010 |
| WO | WO-00/15044 | A1 | 3/2000 |
| WO | WO-01/49281 | A2 | 7/2001 |
| WO | WO-2005/097106 | A1 | 10/2005 |
| WO | WO-2006/127832 | A2 | 11/2006 |
| WO | WO-2007/127263 | A2 | 11/2007 |
| WO | WO 2007127263 | A2 * | 11/2007 |
| WO | WO-2008/016554 | A1 | 2/2008 |
| WO | WO-2009/031023 | A2 | 3/2009 |
| WO | WO-2009/153652 | A2 | 12/2009 |
| WO | WO-2011/011721 | A2 | 1/2011 |
| WO | WO-2012088519 | A2 | 6/2012 |
| WO | WO-2012/156600 | A1 | 11/2012 |

OTHER PUBLICATIONS

Larrosa, M. et al., "Ellagitannins, ellagic acid and vascular health", *Molecular Aspects of Medicine*, 31 (6):513-539 (Pergamon Press, Oxford, Great Britain, Dec. 1, 2010).

Viuda-Martos, M et al., "Pomegranate and its Many Functional Components as Related to Human Health: A Review", *Comprehensive Reviews in Food Science and Food Safety*, 9(6):635-654 (Oct. 22, 2010).

International Search Report and Written Opinion from related PCT application PCT/US2011/067229 dated Jul. 25, 2012.

Office Action from corresponding Colombian Patent Application No. 12-172.849 dated Aug. 28, 2014.

Larossa, M et al., "Anti-inflammatory properties of a pomegranate extract and its metabolite urolithin-A in a colitis rat model and the effect of colon inflammation on phenolic metabolism", *Journal of Nutritional Biochemistry*, 21:717-725 (Elsevier Inc., 2010).

Seeram, N. P. et al., "Pomegranate Ellagitannin-Derived Metabolites Inhibit Prostate Cancer Growth and Localize to the Mouse Prostate Gland", *J. Agric. Food Chem.*, 55:7732-7737 (American Chemcal Society, USA, 2007).

Partial European Search Report for European Application No. 17186188.3 dated Oct. 27, 2017.

"What is Atherosclerosis?" NHLBI, National Institutes of Health (2016).

Espin et al., "Iberian pig as a model to clarify obscure points in the bioavailability and metabolism of ellagitannins in humans," J Agric Food Chem, 55(25): 10476-10485 (2007).

Bhattacharyya et al., "Beneficial Effect of Processed Shilajit on Swimming Exercise Induced Impaired Energy Status of Mice," Pharmacologyonline, 1: 817-825 (2009).

Bhattacharyya et al., "Shilajit Dibezno-alpha-Pyrones: Mitochondria Targeted Antioxidants," Pharmacologyonline, 2: 690-698 (2009).

Cerda, et al., "Identification of Urolithin A as a metabolite produced by human colon microflora from ellagic acid and related compounds," J Agric Food Chem, 53(14): 5571-5576 (2005).

Cerda, et al., "Pomegranate juice supplementation in a chronic obstructive pulmonary disease: a 5-week, randomized, double-blind, placebo-controlled trial," Eur J Clin Nutr, 60: 245-253 (2006).

Dell'agli, et al., "Ellagitannins of fruit rind of pomegranate (*Punica granatum*) antagonize in vitro the host inflammatory response mechanism involved in the onset of malaria," Malaria J, 9: 208 (2010).

Examination Report No. 2 dated Mar. 9, 2016 from corresponding Australian patent application No. 2011348068.

Johanningsmeier et al., "Pomegranate as a functional food and nutraceutical source," Ann Rev Food Sci Technol, 2:181-201 (2010).

Kasimsetty, et al., "Colon cancer ch emo preventive activities of pomegranate ellagitannins and Urolithins," J Agric Food Chem, 58(4): 2180-2187 (2010).

Office Action from corresponding Mexican Patent Application No. MX/a/2013/007262, dated Mar. 11, 2016.

Trombold, J. R. et al., "Ellagitannin Consumption Improves Strength Recovery 2-3 d after Eccentric Exercise", *Medicine and Science in Sports and Exercise*, 42:493-498 (American College of Sports Medicine, Mar. 2010).

Basu et al., "Pomegranate juice: A heart-healthy fruit juice," Nutr Rev, 67(1): 49-56 (2009).

Esmaillzadeh et al., "Concentrated pomegranate juice improves lipid profiles in diabetic patients with hyperlipidemia," J Med Food, 7(3): 305-308 (2004).

Rock et al., "Consumption of wonderful variety pomegranate juice and extract by diabetic patients increases paraoxonase 1 association with high-density lipoprotein and stimulates its catalytic activities," J Agric Food Chern, 56(18): 8704-8713 (2008).

Sumner et al., "Effects of pomegranate juice consumption on myocardial perfusion in patients with coronary heart disease," Am J Cardiol, 96(6): 810-814 (2005).

Hartman, R. E. et al. "Pomegranate juice decreases amyloid load and improves behavior in a mouse model of Alzheimer's disease", *Neurobiology of Disease*, 24(3):506-515 (Elsevier Inc., St. Louis, MO 2006).

Lee, H.-J. et al., "β-Secretase (BACE1) Inhibitors from Sanguisorbae Radix", *Arch. Pharm. Res.*, 28(7):799-803 (Korea, 2005).

Office Action from corresponding Japanese application No. JP2013-546456 dated Oct. 27, 2015.

Abstract of unexamined Japanese application No. JP2010-280627 published Dec. 16, 2010.

Kaarniranta et al., "Age-Related Macular Degeneration (AMD): Alzheimer's Diesease in the Eye?," Journal of Alzheimer's Disease, 24(4):615-631 (2011).

Sorgen, "Eat Smart for a Healthier Brain," WebMD, accessed online:https://www.webmd.com/diet/features/eat-smart-healthier-brain?print=true.

Extended European Search Report issued by the European Patent Office in corresponding Application No. EP18166897 dated May 28, 2018.

Notice of Allowance for U.S. Appl. No. 14/656,096 dated Jun. 14, 2018.

Verzelloni et al., "Antiglycative and Neuroprotective Activity of Colon-Derived Polyphenol Catabolites" Molecular Nutrition and Food Research, 55(1): S35-S43 (2011).

Puzzo et al., "Behavioral assays with mouse models of Alzheimer's disease: practical considerations and guidelines," Biochemical Pharmacology, 88(4): 46 pages (2014).

Raza et al., "Effect of Bitter Melon (*Momordica charantia*) Fruit Juice on the Hepatic Cytochrome P450-Dependent Monooxygenases and Glutathione S-Transferases in Streptozotocin-lnduced Diabetic Rats," Biochemical Pharmacology, 52:1639-1642 (1996).

Raza et al., "Modulation of Xenobiotic Metabolism and Oxidative Stress in Chronic Streptozotocin-lnduced Diabetic Rats Fed with Momordica charantia Fruit Extract," J Biochem Molecular Toxicology, 14(3): 131-139 (2000).

Sanders et al., "The place of the hippocampus in fear conditioning," European Journal of Pharmacology, 463: 217-223 (2003).

Taylor et al., "Behavioral phenotyping of mouse models of Parkinson's Disease," Behavioural Brain Research, 211(1): 19 pages (2010).

Gonzalez-Sarrias et al., "Dissimilar In Vitro and In Vivo Effects of Ellagic Acid and Its Microbiota-Derived Metabolites, Urolithins, on the Cytochrome P450 1A1," Journal of Agricultural and Food Chemistry, 57: 5623-5632 (2009).

Hoefer et al., "Fear conditioning in frontotemporal lobar degeneration and Alzheimer's disease," Brian, 131: 1646-1657 (2008).

Bishop et al., "Neural mechanisms of ageing and cognitive decline," Nature, 464(7288):529-535 (2010).

(56) References Cited

OTHER PUBLICATIONS

Kharkevich, "Parmakolociva" [Pharmacology], Manual for Students of Medical Institutes, Moscow, Meditsina, 47-48 (1987).

* cited by examiner

Urolithin A (UA)

Ellagic Acid (EA)

Tellimagrandin (TL)

Punicalagin (PA)

Punicalin (PB)

*** p<0.001 when compared to differentiated control cells

* p< 0.05,  p<0.01, * p<0.001 when compared to differentiated control cells

* p< 0.05,  p<0.01, * p<0.001 when compared to differentiated control cells

* p< 0.05,  p<0.01, * p<0.001 when compared to differentiated control cells

*** p<0.001 when compared to differentiated control cells

*** p<0.001 when compared to differentiated control cells

*** p<0.001 when compared to differentiated control cells

* p< 0.05,  p<0.01, * p<0.001 when compared to differentiated control cells p<0.01, * p<0.001 when compared to differentiated control cells

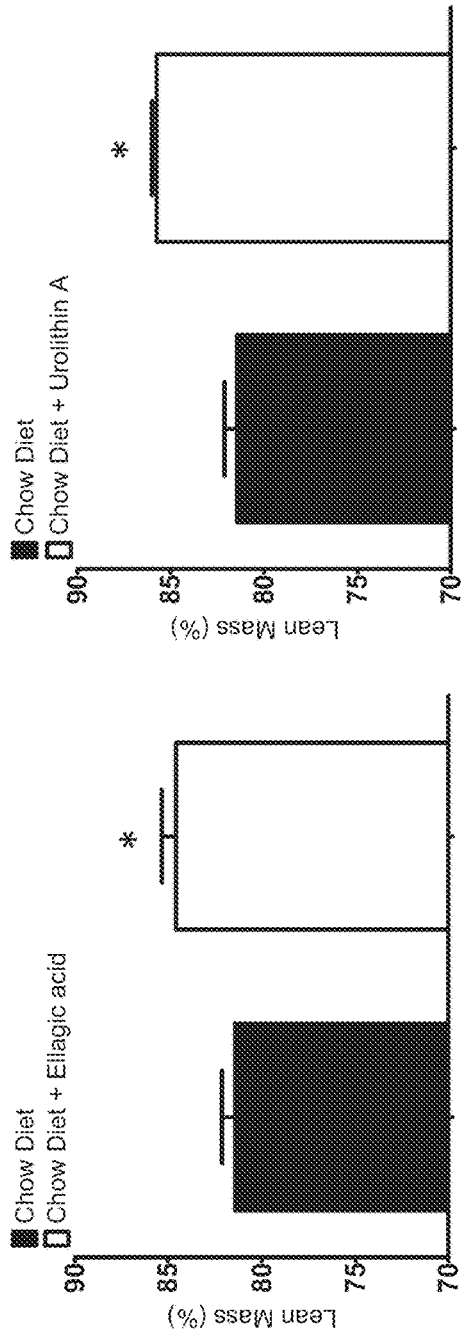
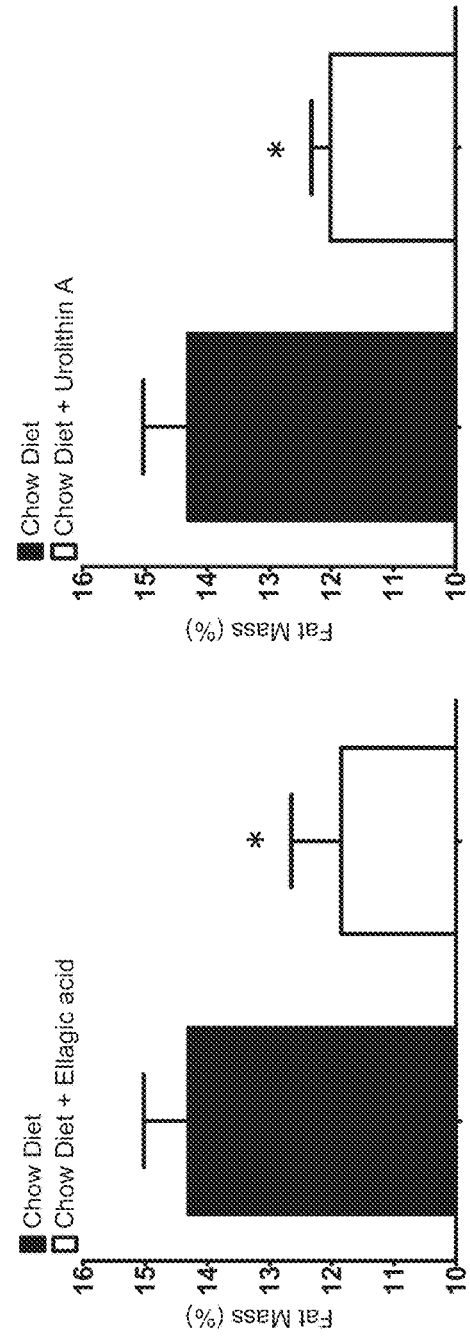
Figure 18A
Figure 18B

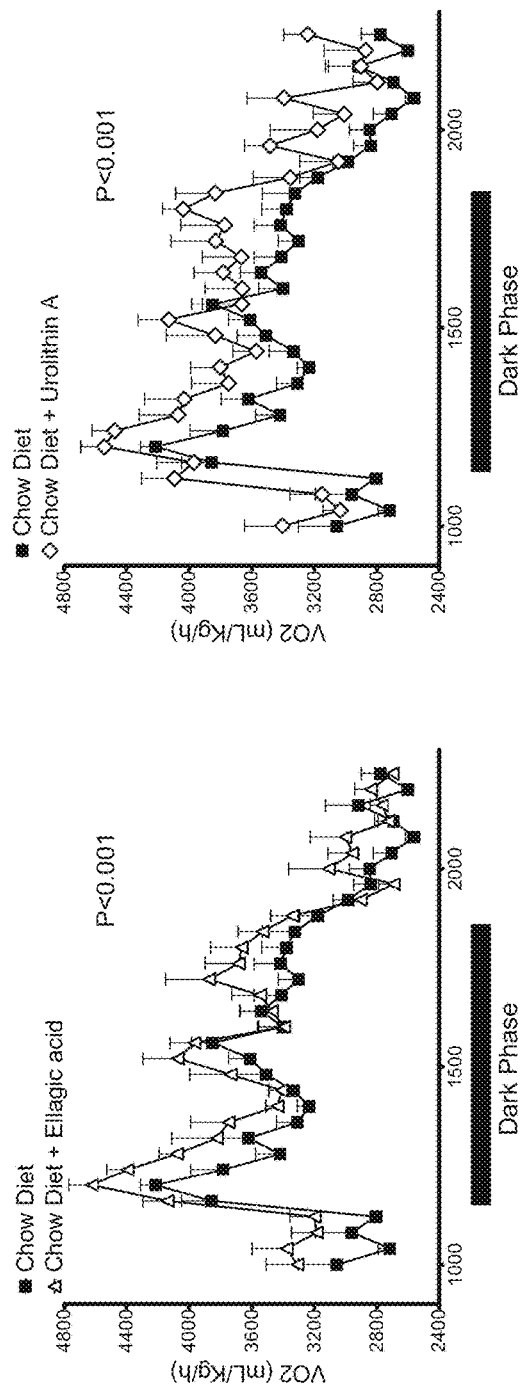
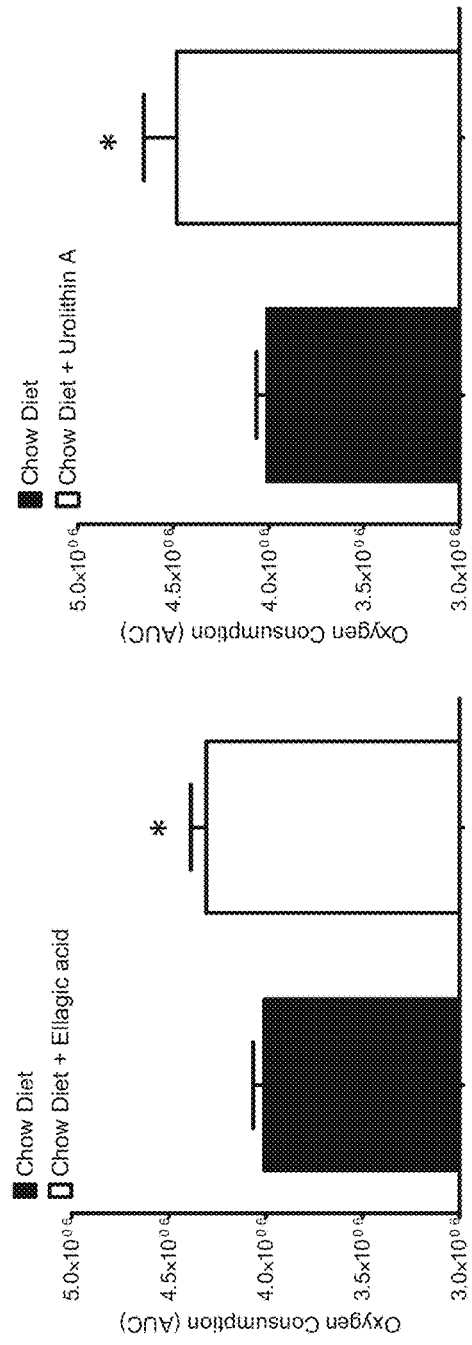
Figure 19A
Figure 19B

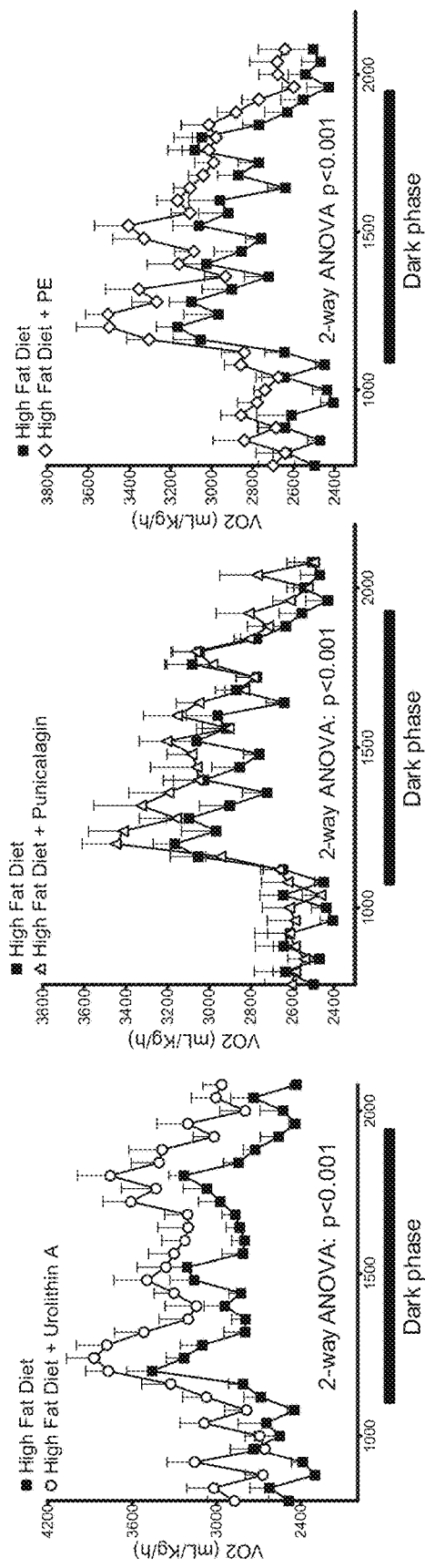
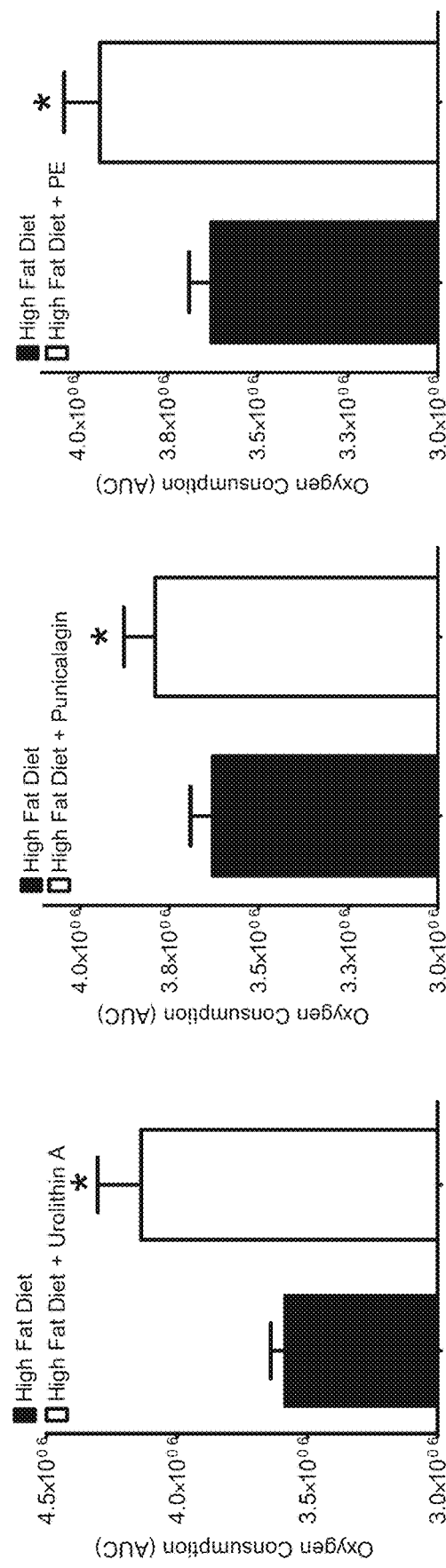
Figure 20A
Figure 20B

```
                             SEQUENCE LISTING

<160> NUMBER OF SEQ ID NOS: 18

<210> SEQ ID NO 1
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 1
aagtgtggaa ctctctggaa ctg                                              23

<210> SEQ ID NO 2
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 2
gggttatctt ggttggcttt atg                                              23

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
aagtgttttt ccagcatggg                                                  20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
ggctgcaatt ttcctaacca                                                  20

<210> SEQ ID NO 5
<211> LENGTH: 17
```

```
<212> TYPE: DNA
<213> ORGANISM: Artificial sequence
<220> FEATURE:
<223> OTHER INFORMATION: Synthetic oligonucleotide

<400> SEQUENCE: 5
tcatggaata gagcgcc                                                        17

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
gtgtgctcac cgattctaca                                                     20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
cccatgtgct cctaccagat                                                     20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ccttgaagaa gcgacctttg                                                     20

<210> SEQ ID NO 9
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 9
gatcgcaatg ggtgcttttg atagaa                                              26

<210> SEQ ID NO 10
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 10
agctgattgg caatgtctcc agcaaa                                              26

<210> SEQ ID NO 11
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 11
```

```
gtagcttatg aatgtgtgca actc                                          24

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 12
gtcttgcgat cagctctttc atta                                          24

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
gcacacattt ccccacactg                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cccaacctgc ccattctgat                                               20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
tccatcaggg tatcctctcc                                               20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ggaggcaagc ataagactgg                                               20

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
acgtcaaagg gtacctgtcc a                                             21

<210> SEQ ID NO 18
<211> LENGTH: 21
<212> TYPE: DNA
<213> ORGANISM: Artificial sequence
```

-continued

```
<220> FEATURE:
<223> OTHER INFORMATION: Synthetic oligonucleotide

<400> SEQUENCE: 18
caatcccaga tggcagaact t                                              21
```

COMPOSITIONS AND METHODS FOR IMPROVING MITOCHONDRIAL FUNCTION AND TREATING NEURODEGENERATIVE DISEASES AND COGNITIVE DISORDERS

RELATED APPLICATION

This application is a divisional of U.S. patent application Ser. No. 13/336,841, filed Dec. 23, 2011, which claims benefit under 35 U.S.C. 119(e) of U.S. Provisional Patent Application No. 61/426,957, filed Dec. 23, 2010.

SEQUENCE LISTING

The sequence listing contained in the 5 kb ASCII text file named "AZX-005.01 ST.25.txt", created on Dec. 22, 2011, is incorporated herein by reference.

BACKGROUND OF THE INVENTION

Ellagitannins are monomeric, oligomeric, and polymeric polyphenols that are abundant in some fruits, berries and nuts, such as pomegranates, raspberries, strawberries, black raspberries, walnuts and almonds. The fruits and berries are widely consumed fresh and as beverages, such as juice, and these have been reported to promote health.

In commercial fruit juice processing methods, ellagitannins, which are particularly abundant in some fruit peels, are extracted in large quantities into the juice. Ellagitannins belong to the chemical class of hydrolyzable tannins, which release ellagic acid upon hydrolysis. In vitro studies have suggested that ellagitannins, at concentrations in the range of 10-100 micromolar ($\mu$M), have potential anti-oxidant, anti-atherogenic, anti-thrombotic, anti-inflammatory, and anti-angiogenic effects. Fruits may have different ellagitannins that are predominant, for example, in fruit juice prepared from pomegranate, the predominant ellagitannin is punicalagin [2,3 hexahydroxydiphenoyl-4,6-gallagylglucose], which occurs as a mixture of isomers. The reported potent anti-oxidant properties of pomegranate juice have been attributed to the high content of punicalagin isomers, which can reach levels >2 g/L of juice. Ellagitannins have also been identified as the active anti-atherogenic compounds in pomegranate juice. It has also been suggested that pomegranate ellagitannins and pomegranate fruit extracts inhibit the proliferation of human cancer cells and modulate inflammatory sub-cellular signaling pathways and apoptosis. See, for example, Seeram et al. (2005) *J Nutr Biochem.* 16:360-7; Adams et al. (2006) *J Agric Food Chem.* 54:980-85; Afaq et al. (2005) *Photochem Photobiol.* 81:38-45; Afaq et al. (2005) *Int J Cancer.* 113:423-33. Pomegranate fruit extract has also been reported to reduce prostate tumor growth and prostate serum antigen (PSA) levels in athymic nude mice implanted with CWR22Rv1 prostate cells. Malik et al. (2005) *Proc Natl Acad Sci.* 102:14813-8.

Unfortunately, for the most part ellagitannins are poorly absorbed by the human gut. However, a number of metabolites derived from ellagitannins are absorbed by the human gut, including certain metabolites ultimately formed in the gut by commensal microorganisms (i.e., intestinal microflora).

Ellagitannins release ellagic acid under physiological conditions in vivo, and ellagic acid is then gradually metabolized by the gut microflora in the intestine to produce urolithin D, urolithn C, urolithin A (UA) and urolithin B (UB). Once the metabolites are absorbed, they undergo glucuronidation and once in the liver, they are further metabolized to produce glucuronides, and/or sulfates, to give a combination of metabolites secreted in the bile.

Urolithins are metabolites of ellagic acid, punicalagin (PA), punicalin (PB), tellimagrandin (TL), and other ellagitannins (Cerda, Espin et al. 2004; Cerda, Periago et al. 2005). Ellagic acid (EA) is abundant in pomegranate juice (Gil, Tomas-Barberan et al. 2000). The ellagitannin tellimagrandin (TL) has been previously isolated and characterized before from pomegranate and other plants (Tanaka, Nonaka et al. 1986; Tanaka, Nonaka et al. 1986; Satomi, Umemura et al. 1993). Structural formulas for UA, PA, PB, EA, and TL are presented in FIG. 1.

Considerable efforts have been made to understand the mechanism of metabolic disorders, neurodegeneration and cognitive decline, so as to better design treatment modalities including those based on natural products. One of the key observations has been the role of declining mitochondrial energy production, corresponding with increased oxidative stress and apoptosis, plays a significant role in degenerative diseases and the process of aging. A variety of degenerative diseases have now been shown to be caused by mutations in mitochondrial genes encoded by the mitochondrial DNA (mtDNA) or the nuclear DNA (nDNA). Importantly, somatic mtDNA mutations accumulate with age in post-mitotic tissues in association with the age-related decline in mitochondrial function and are thought to be an important factor in aging and senescence. Inherited diseases can result from mtDNA base substitution and rearrangement mutations and can affect the CNS, heart and skeletal muscle, and renal, endocrine and hematological systems.

Mitochondria generate most of the cellular energy by oxidative phosphorylation (OXPHOS), and they produce most of the toxic reactive oxygen species (ROS) as a by-product. Genetic defects that inhibit OXPHOS also cause the redirection of OXPHOS electrons into ROS production, thus increasing oxidative stress. A decline in mitochondrial energy production and an increase in oxidative stress can impinge on the mitochondrial permeability transition pore (mtPTP) to initiate programmed cell death (apoptosis). The interaction of these three factors is believed to play a major role in the pathophysiology of degenerative diseases and the aging process, which affects all tissues of the body.

In the normal brain, optimal cognitive function mainly relies on the activity and communication between neurons, highly complex cells able to convey electric signals and elicit chemical neurotransmission. Neuronal function depends on long and complex cellular processes that can extend over centimeters or even meters to connect neurons or target cells, and can make more than 100,000 synaptic contacts. As such, neurons are highly dependent on energy supply and, therefore, are exposed to oxidative stress damage. Cognitive function is dependent on a careful balance of intracellular signaling that takes place within a complex network of neurons. Optimal cognitive function can be impaired by numerous factors such as aging, cellular stress, chronic stress, and neurodegenerative disorders. Cognitive decline may be characterized by a decrease in performance in thinking, learning, memory, alertness, and/or impaired psychological skills, as well as by depression and anxiety.

Mitochondrial function has also been shown to be important in metabolic disorders. Diabetes and obesity have been correlated with compromises in mitochondrial function. It has been suggested that the coupling efficiency in mitochondria, or the proportion of oxygen consumption necessary to make ATP, is related to levels of obesity, with high coupling efficiency possibly resulting in higher deposition of fat stores (Harper, Green et al. 2008). In diabetes, recent work has suggested that mitochondrial dysfunction is a cause of insulin insensitivity in myocytes and adipocytes, as a result of insufficient energy supply or defects in the insulin signaling pathway (Wang, Wang et al. 2010).

SUMMARY OF THE INVENTION

The invention relates to compositions comprising compounds or precursors to compounds which may be used for a variety of therapeutic applications including, for example, treating and/or preventing disease or disorders related to reduced or inadequate mitochondrial activity, including aging or stress, diabetes, obesity, and neurodegenerative diseases. These same compounds and compositions can also be used advantageously in generally healthy individuals to increase or maintain metabolic rate, decrease percent body fat, increase or maintain muscle mass, manage body weight, improve or maintain mental performance (including memory), improve or maintain muscle performance, improve or maintain mood, and manage stress.

An object of the present invention provides a plant extract, active fraction thereof, or one or more active components or metabolites isolatable therefrom or synthesized, for use in the prophylaxis or treatment of a disease state initiated or characterized (i) by inadequate mitochondrial activity; (ii) by metabolic disorders such as diabetes and obesity; (iii) by a decline in cognitive function; or (iv) by mood disturbances.

Accordingly, in a first aspect, the invention provides a fruit extract, active fraction thereof, or one or more active components isolatable therefrom, for use as an inducer of mitochondrial function.

As used herein, the term "fraction" refers to purified or partially purified extracts.

In another aspect, the invention provides a fruit extract, active fraction thereof, or one or more active components isolatable therefrom, for use in the prophylaxis or treatment of a disease state initiated or characterized by reduced mitochondrial function.

In another aspect, the invention provides the use of a fruit or an extract, or active fraction thereof, or one or more active components isolatable therefrom, as hereinbefore defined for the manufacture of a medicament for use in (i) the prophylaxis or treatment of a disease state initiated or characterized by reduced mitochondrial function; or (ii) improving cognitive or muscular function. Such disease states can include, without limitation, neurodegenerative disease, cognitive disorder, mood disorder, anxiety disorder, metabolic disorder, diabetes mellitus, and obesity.

In another aspect, the invention provides a process for the manufacture of a medicament for use in (i) the prophylaxis or treatment of a disease state initiated or characterized by reduced mitochondrial function; or (ii) improving cognitive or muscular function; which process is characterized by the use, as an essential ingredient of the medicament, of a fruit, or an extract or active fraction thereof or one or more active components isolatable therefrom as hereinbefore defined.

In a still further aspect, the invention provides a pharmaceutical composition comprising an active component derived from a fruit or an extract or active fraction or one or more active components isolatable therefrom as hereinbefore defined and a pharmaceutically acceptable carrier.

An object of the present invention is to provide plant extracts, active fraction thereof, or one or more active components or metabolites isolatable therefrom, or synthesized, for use in treating diseases or disorders in a subject that would benefit from increased mitochondrial activity, for improving (i) brain function, (ii) metabolic function, including diabetes or obesity, (iii) muscle performance and (iv) increasing tissue ATP levels.

An object of the present invention is to provide extracts, compositions and compounds which are neuroprotective, neurotrophic, and/or promote neurite outgrowth and, consequently, improve cognitive function, as well as methods of use of these compounds and compositions.

An object of the present invention is to provide compounds and compositions that improve, protect, and maintain brain function and cognition. Another object of this invention is to improve, protect against and manage mood disorders. Another object of this invention is to protect against stress-induced or stress-associated disorders or symptoms.

An object of this invention is to provide neuroprotective compounds to protect the brain from insults, as well as improve cognitive performance and memory in normal adults. Another object of the present invention is to provide new compounds that stimulate neuronal plasticity. Neuronal plasticity is well known to be a key process necessary for memory and cognitive functions. Such compounds may influence neurite outgrowth, number of branches per cells, mean processes per cells and even numbers of synapses formed.

The invention also relates to several polyphenol compounds and derivatives thereof, related to ellagitannins, as bioactive natural compounds found in pomegranate and other fruit, as well as bioactive natural extracts which contain these compounds. These compounds include ellagitannins, punicalagin, and ellagic acid, all which are found in the pomegranate, but can also be isolated from other fruits and berries, as well as metabolites of these compounds. As disclosed herein, these compounds have now been shown to have beneficial effects on (i) mitochondrial function, (ii) cellular metabolism, and (iii) neuronal plasticity.

Using in vitro modeling of neurite outgrowth and process formation in neuronal cell culture and primary cells, various compounds were examined for their beneficial effects. As described above, aging, neurodegeneration, and chronic stress have negative impacts on neurite outgrowth. Remarkably, it has been discovered that the compounds of the present invention have neuroprotective properties, exhibit strong stimulatory activity in PC-12 cells and primary mesencephalic neurons, and improve cognitive function and memory in animal models.

In one aspect, the invention relates to a composition, such as a pharmaceutical, a medical food, a functional food, a food additive, or a dietary supplement, comprising the compounds or a mixture thereof of the invention. The composition may also optionally contain an additional therapeutic agent, or may be administered in combination with another therapeutic compound. Packaged products, containing the above-mentioned composition and a label and/or instructions for use in improving memory and cognitive performance and or for the treatment of a disease or condition associated with damage to the brain typical for conditions found in the aging adult, are also provided.

An aspect of the invention is a food product or nutritional supplement comprising an effective amount of pomegranate extract: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

An aspect of the invention is a food product or nutritional supplement comprising an effective amount of an ellagitannin: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

An aspect of the invention is a food product or nutritional supplement comprising an effective amount of punicalagin: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

An aspect of the invention is a food product or nutritional supplement comprising an effective amount of ellagic acid: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

An aspect of the invention is a food product or nutritional supplement comprising an effective amount of a urolithin: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

In each of the foregoing, in one embodiment the condition is obesity.

In each of the foregoing, in one embodiment the condition is reduced metabolic rate.

In each of the foregoing, in one embodiment the condition is metabolic syndrome.

In each of the foregoing, in one embodiment the condition is diabetes mellitus.

In each of the foregoing, in one embodiment the condition is cardiovascular disease.

In each of the foregoing, in one embodiment the condition is hyperlipidemia.

In each of the foregoing, in one embodiment the condition is neurodegenerative disease.

In each of the foregoing, in one embodiment the condition is cognitive disorder.

In each of the foregoing, in one embodiment the condition is mood disorder.

In each of the foregoing, in one embodiment the condition is stress.

In each of the foregoing, in one embodiment the condition is anxiety disorder.

In each of the foregoing, in one embodiment the food product or nutritional supplement is for weight management.

In each of the foregoing, in one embodiment the food product or nutritional supplement is for increasing muscle performance.

In each of the foregoing, in one embodiment the food product or nutritional supplement is for increasing mental performance.

An aspect of the invention is a method of increasing or maintaining mitochondrial function. The method includes the step of contacting cells with an effective amount of a urolithin or a precursor thereof, to increase function of the mitochondria.

An aspect of the invention is a method of treating, preventing, or managing a mitochondria-related disease or condition associated with an altered mitochondrial function or a reduced mitochondrial density. The method includes the step of administering to a subject in need thereof a therapeutically effective amount of a urolithin or a precursor thereof, to treat the disease or condition associated with altered mitochondrial function or reduced mitochondrial density.

An aspect of the invention is a method of increasing metabolic rate. The method includes the step of administering to a subject in need thereof an effective amount of a urolithin or a precursor thereof, to increase metabolic rate.

An aspect of the invention is a method of preventing or treating metabolic syndrome. The method includes the step of administering to a subject in need thereof an effective amount of a urolithin or a precursor thereof, to prevent or treat metabolic syndrome.

An aspect of the invention is a method of preventing or treating obesity. The method includes the step of administering to a subject in need thereof an effective amount of a urolithin or a precursor thereof, to prevent or treat obesity.

An aspect of the invention is a method of preventing or treating cardiovascular disease. The method includes the step of administering to a subject in need thereof an effective amount of a urolithin or a precursor thereof, to prevent or treat cardiovascular disease.

An aspect of the invention is a method of treating hyperlipidemia. The method includes the step of administering to a subject in need thereof an effective amount of a urolithin or a precursor thereof, to treat hyperlipidemia. In one embodiment, the hyperlipidemia is hypertriglyceridemia. In one embodiment, the hyperlipidemia is elevated free fatty acids.

An aspect of the invention is a method of treating a metabolic disorder. The method includes the step of administering to a subject in need thereof a therapeutically effective amount of a urolithin or a precursor thereof, to treat the metabolic disorder. In one embodiment, the metabolic disorder is diabetes mellitus. In one embodiment, the metabolic disorder is obesity.

An aspect of the invention is a method of treating a neurodegenerative disease. The method includes the step of administering to a subject in need thereof a therapeutically effective amount of a urolithin or a precursor thereof, to treat the neurodegenerative disease. In one embodiment, the neurodegenerative disease is selected from the group consisting of AIDS dementia complex, Alzheimer's disease, amyotrophic lateral sclerosis, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Huntington's disease, Kennedy's disease, Krabbe disease, Lyme disease, Machado-Joseph disease, multiple sclerosis, multiple system atrophy, neuroacanthocytosis, Niemann-Pick disease, Parkinson's disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome. In one embodiment, the neurodegenerative disease is selected from the group consisting of Alzheimer's disease, amyotrophic lateral sclerosis, Huntington's disease, and Parkinson's disease. In one embodiment, the neurodegenerative disease is Alzheimer's disease.

An aspect of the invention is a method of improving cognitive function. The method includes the step of administering to a subject in need thereof an effective amount of a urolithin or a precursor thereof, to improve cognitive function. In one embodiment, the cognitive function is selected from the group consisting of perception, memory, attention, speech comprehension, speech generation, reading comprehension, creation of imagery, learning, and reasoning. In one embodiment, the cognitive function is selected from the group consisting of perception, memory, attention, and reasoning. In one embodiment, the cognitive function is memory.

An aspect of the invention is a method of treating a cognitive disorder. The method includes the step of administering to a subject in need thereof a therapeutically effective amount of a urolithin or a precursor thereof, to treat the cognitive disorder. In one embodiment, the cognitive disorder is selected from the group consisting of delirium, dementia, learning disorder, attention deficit disorder (ADD), and attention deficit hyperactivity disorder (ADHD). In one embodiment, the cognitive disorder is a learning disorder. In one embodiment, the cognitive disorder is attention deficit disorder (ADD). In one embodiment, the cognitive disorder is attention deficit hyperactivity disorder (ADHD). An aspect of the invention is a method of treating stress-induced or stress-related cognitive deficit. The method includes the step of administering to a subject in need thereof a therapeutically effective amount of a urolithin or a precursor thereof, to treat the stress-induced or stress-related deficit.

An aspect of the invention is a method of treating a mood disorder. The method includes the step of administering to a subject in need thereof a therapeutically effective amount of a urolithin or a precursor thereof, to treat the mood disorder. In one embodiment, the mood disorder is selected from the group consisting of depression, postpartum depression, dysthymia, and bipolar disorder. In one embodiment, the mood disorder is depression. In one embodiment, the mood disorder is dysthymia.

An aspect of the invention is a method of treating stress-induced or stress-related mood disorder, e.g., dysthymia. The method includes the step of administering to a subject in need thereof a therapeutically effective amount of a urolithin or a precursor thereof, to treat the stress-induced or stress-related mood disorder.

An aspect of the invention is a method of treating an anxiety disorder. The method includes the step of administering to a subject in need thereof a therapeutically effective amount of a urolithin or a precursor thereof, to treat the anxiety disorder. In one embodiment, the anxiety disorder is selected from the group consisting of generalized anxiety disorder, panic disorder, panic disorder with agoraphobia, agoraphobia, social anxiety disorder, obsessive-compulsive disorder, and post-traumatic stress disorder. In one embodiment, the anxiety disorder is generalized anxiety disorder. In one embodiment, the anxiety disorder is post-traumatic stress disorder.

An aspect of the invention is a method of treating stress-induced or stress-related anxiety. The method includes the step of administering to a subject in need thereof a therapeutically effective amount of a urolithin or a precursor thereof, to treat the stress-induced or stress-related anxiety.

An aspect of the invention is a method of enhancing muscle performance. The method includes the step of administering to a subject in need thereof a therapeutically effective amount of a urolithin or a precursor thereof, to increase muscle performance. In one embodiment, the muscle performance is selected from the group consisting of strength, speed, and endurance.

An aspect of the invention is a method of treating a muscle or neuromuscular disease. The method includes the step of administering to a subject in need thereof a therapeutically effective amount of a urolithin or a precursor thereof, to treat the muscle or neuromuscular disease. In one embodiment, the muscle or neuromuscular disease is a myopathy. In one embodiment, the muscle or neuromuscular disease is a muscular dystrophy. In one embodiment, the muscle or neuromuscular disease is Duchenne muscular dystrophy.

An aspect of the invention is a method of promoting neurite outgrowth. The method includes the step of contacting a nerve cell with an effective amount of a urolithin or a precursor thereof, to promote neurite outgrowth. In one embodiment, the contacting comprises administering to a subject in need thereof a therapeutically effective amount of the urolithin or precursor thereof, to promote neurite outgrowth.

The following embodiments can pertain to each aspect and embodiment of the invention described and, as appropriate, to each other.

In one embodiment, the urolithin or precursor thereof is an isolated urolithin.

In one embodiment, the urolithin or precursor thereof is an isolated urolithin precursor.

In one embodiment, the urolithin is selected from the group consisting of urolithin A, urolithin B, urolithin C, urolithin D, as well as their metabolites, including, by means of example, their glucuronidated, methylated, and sulfated forms, and combinations of these urolithins.

In one embodiment, the urolithin or precursor thereof is administered as a natural food selected from the group consisting of berries, grapes, pomegranates, rose hips, and nuts.

In one embodiment, the urolithin or precursor thereof is administered as a processed food product, including as means of example a juice, concentrate, or extract, based on a natural food selected from the group consisting of berries, grapes, pomegranates, rose hips, and nuts.

In one embodiment, the urolithin or precursor thereof is administered as pomegranate juice, concentrate, or extract.

In one embodiment, the urolithin or precursor thereof is administered as an ellagitannin.

In one embodiment, the urolithin or precursor thereof is administered as punicalagin.

In one embodiment, the urolithin or precursor thereof is administered as ellagic acid.

In one embodiment, the urolithin or precursor thereof is administered as a urolithin.

In one embodiment, the urolithin or precursor thereof is administered orally.

In one embodiment, the urolithin or precursor thereof is administered parenterally.

In one embodiment, the urolithin or precursor thereof is administered at least weekly. In various embodiments, the urolithin or precursor thereof is administered 1, 2, 3, 4, 5, 6, 7, 8, 9, 10, 11, 12, 13, 14, 15, 16, 17, 18, 19, 20, 21, 22, 23, 24, 25, 26, 27, or 28 times weekly.

In one embodiment, the urolithin or precursor thereof is administered at least daily.

In various embodiments, the urolithin or precursor thereof is administered 1, 2, 3, 4, 5, 6, 7, or 8 times daily.

In one embodiment, the urolithin or precursor thereof is administered in a dose equal or equivalent to 0.1-150 milligram (mg) of urolithin per kilogram (kg) body weight. In one embodiment, the urolithin or precursor thereof is administered in a dose equal or equivalent to 2-120 mg of urolithin per kg body weight. In one embodiment, the urolithin or precursor thereof is administered in a dose equal or equivalent to 4-90 mg of urolithin per kg body weight. In one embodiment, the urolithin or precursor thereof is administered in a dose equal or equivalent to 8-30 mg of urolithin per kg body weight.

In one embodiment, the urolithin or precursor thereof is administered in a dose sufficient to achieve a peak serum level of at least 0.001 micromolar ($\mu$M). In one embodiment, the urolithin or precursor thereof is administered in a dose sufficient to achieve a peak serum level of at least 0.01 $\mu$M. In one embodiment, the urolithin or precursor thereof is administered in a dose sufficient to achieve a peak serum level of at least 0.1 $\mu$M. In one embodiment, the urolithin or precursor thereof is administered in a dose sufficient to achieve a peak serum level of at least 1 $\mu$M. In one embodiment, the urolithin or precursor thereof is administered in a dose sufficient to achieve a peak serum level of at least 10 $\mu$M.

In one embodiment, the urolithin or precursor thereof is administered in a dose sufficient to achieve a sustained serum level of at least 0.001 micromolar ($\mu$M). In one embodiment, the urolithin or precursor thereof is administered in a dose sufficient to achieve a sustained serum level of at least 0.01 $\mu$M. In one embodiment, the urolithin or precursor thereof is administered in a dose sufficient to achieve a sustained serum level of at least 0.1 $\mu$M. In one embodiment, the urolithin or precursor thereof is administered in a dose sufficient to achieve a sustained serum level of at least 1 $\mu$M. In one embodiment, the urolithin or precursor thereof is administered in a dose sufficient to achieve a sustained serum level of at least 10 $\mu$M.

In one embodiment, the subject is not receiving a urolithin or a precursor thereof, to treat another condition calling for administration of a urolithin or a precursor or metabolite thereof, selected from the group consisting of atherosclerosis, thrombosis, cancer, unwanted angiogenesis, infection, and inflammation.

phosphorylated AMPK. Control: negative control; RSV: resveratrol positive control.

Figure 5A:
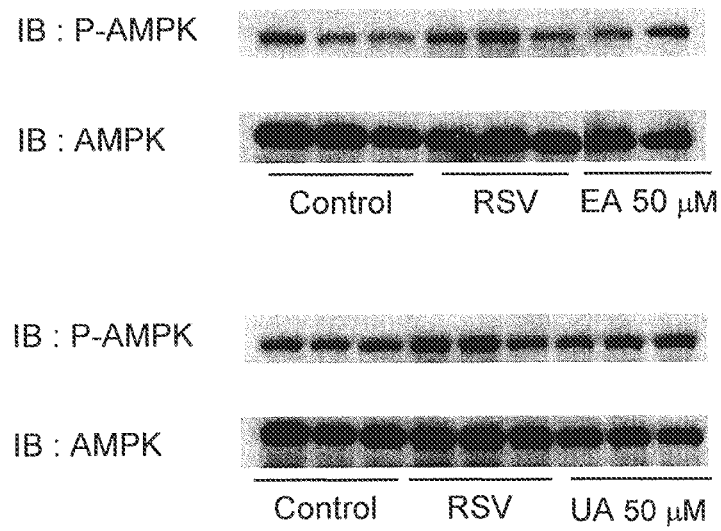
FIG. 5A is a collage of immunoblots (IB) depicting effects of ellagic acid (EA) and urolithin A (UA) at the indicated concentrations on levels of AMP-Activated Protein Kinase (AMPK) and activated, phosphorylated AMPK (P-AMPK). P-AMPK.
Figure 5B:
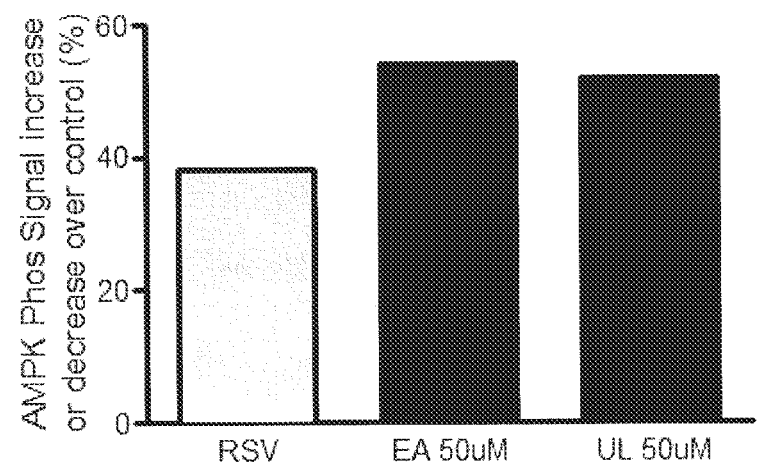

FIG. 5B is a bar graph depicting densitometric analysis of bands in FIG. 5A showing the relative level of activated P-AMPK following treatments as compared to control treated cells.

Figure 6:
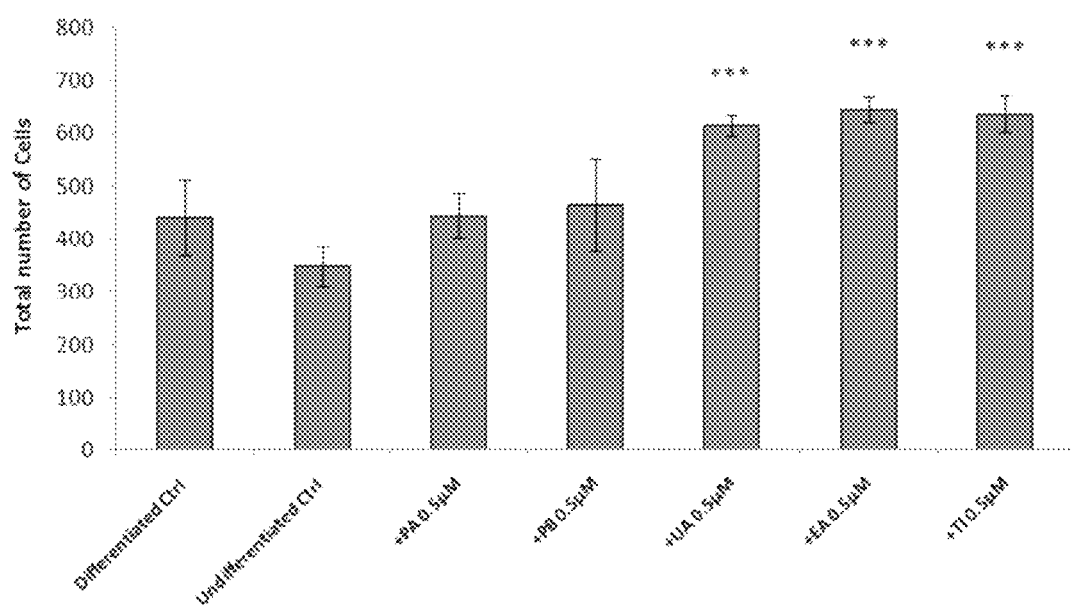

FIG. 6 is a bar graph depicting the total cell numbers for cultures of PC-12 cells following treatment with 0.5 $\mu$M of the indicated compounds. PA, punicalagin; PB, punicalin; UA, urolithin A; EA, ellagic acid; T1, tellimagrandin.

Figure 7:
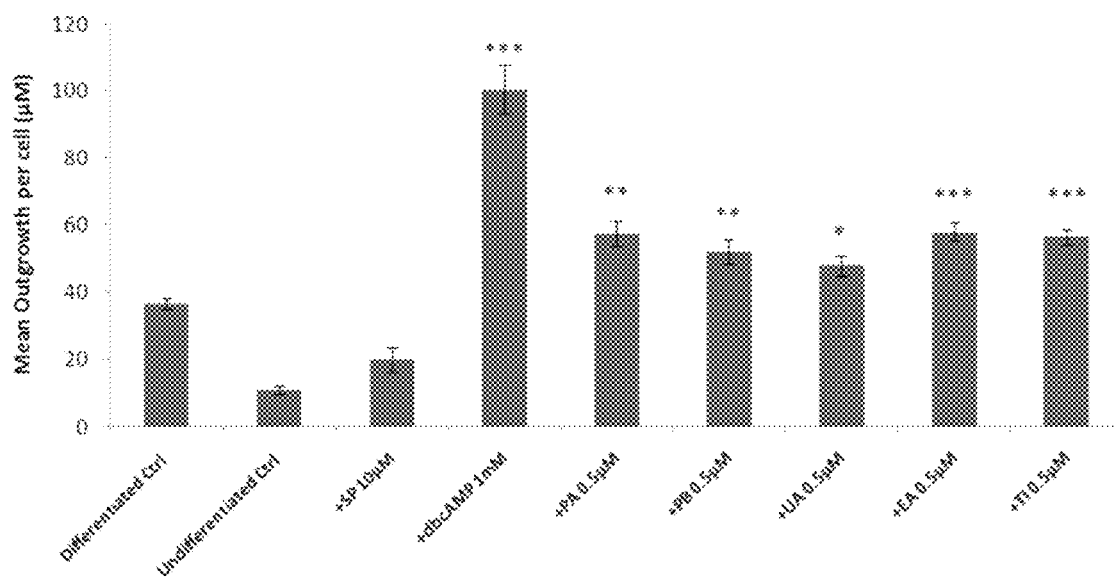

FIG. 7 is a bar graph depicting the mean neurite outgrowth ($\mu$m) in PC-12 cells following treatment with 0.5 $\mu$M of the indicated compounds. Outgrowth is expressed per cell. SP, SP600125; dbcAMP, dibutyryl cyclic AMP; PA, punicalagin; PB, punicalin; UA, urolithin A; EA, ellagic acid; T1, tellimagrandin.

Figure 8:
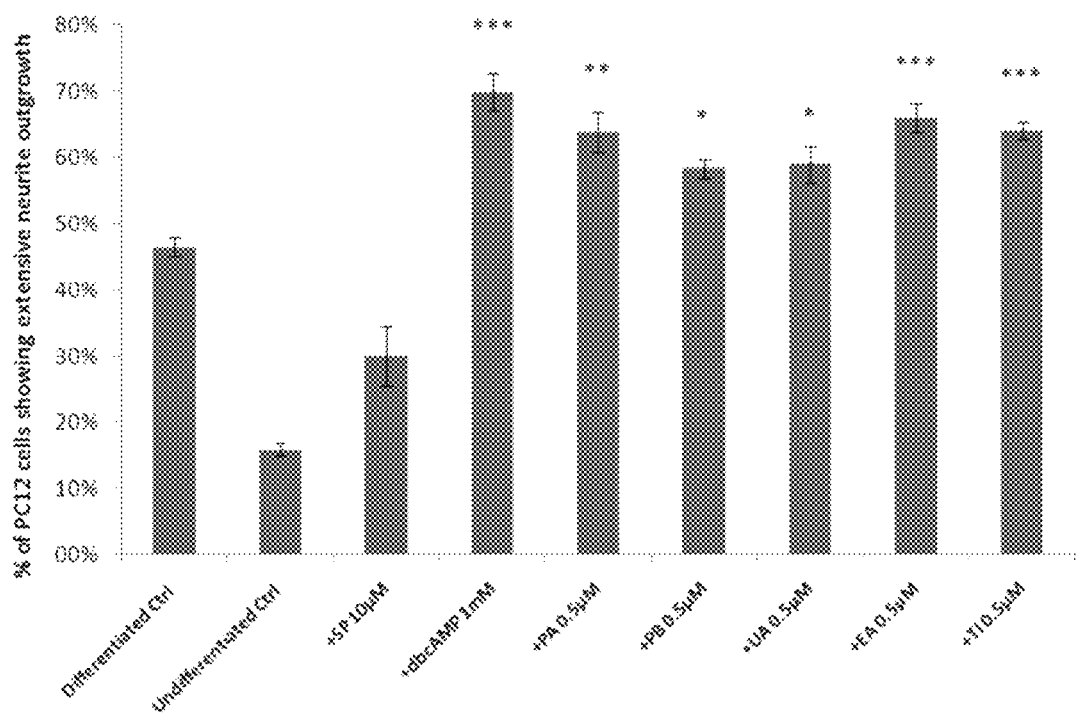

FIG. 8 is a bar graph depicting the percentage of PC-12 cells showing extensive neurite outgrowth (>20 $\mu$m) following treatment with 0.5 $\mu$M of the indicated compounds. SP, SP600125; dbcAMP, dibutyryl cyclic AMP; PA, punicalagin; PB, punicalin; UA, urolithin A; EA, ellagic acid; T1, tellimagrandin.

Figure 9:
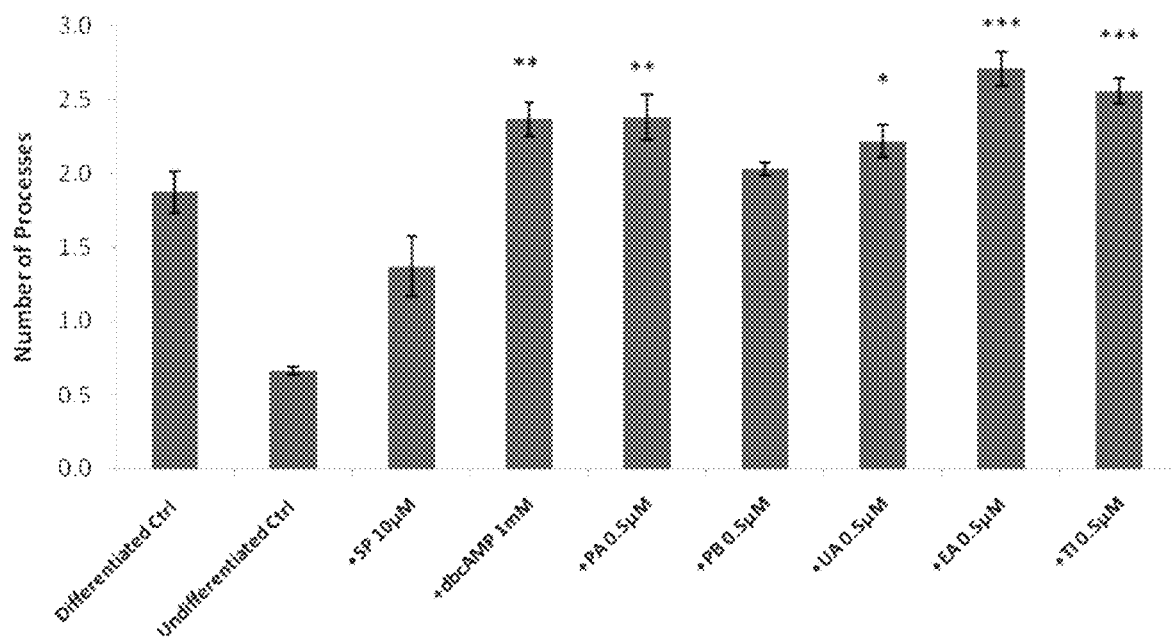

FIG. 9 is a bar graph depicting the mean process formation in PC-12 cells following treatment with 0.5 $\mu$M of the indicated compounds. SP, SP600125; dbcAMP, dibutyryl cyclic AMP; PA, punicalagin; PB, punicalin; UA, urolithin A; EA, ellagic acid; T1, tellimagrandin.

Figure 10:
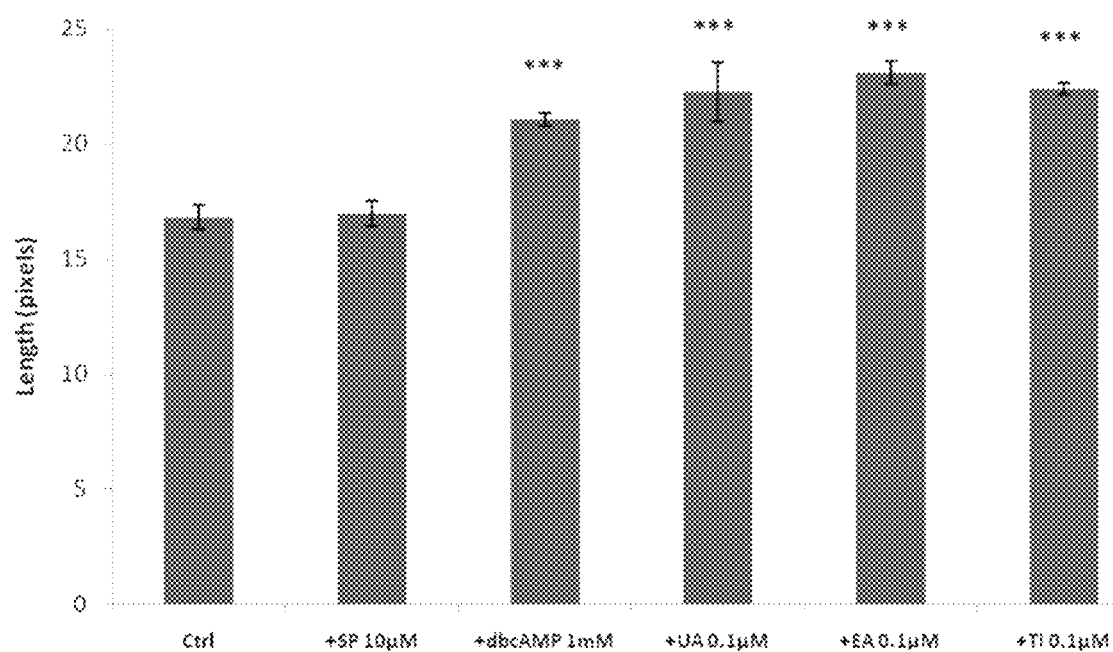

FIG. 10 is a bar graph depicting the mean outgrowth per cell of primary dopaminergic tyrosine hydroxylase (TH)-positive neurons following treatment with 0.1 $\mu$M of the indicated compounds. SP, SP600125; dbcAMP, dibutyryl cyclic AMP; UA, urolithin A; EA, ellagic acid; T1, tellimagrandin.

Figure 11:
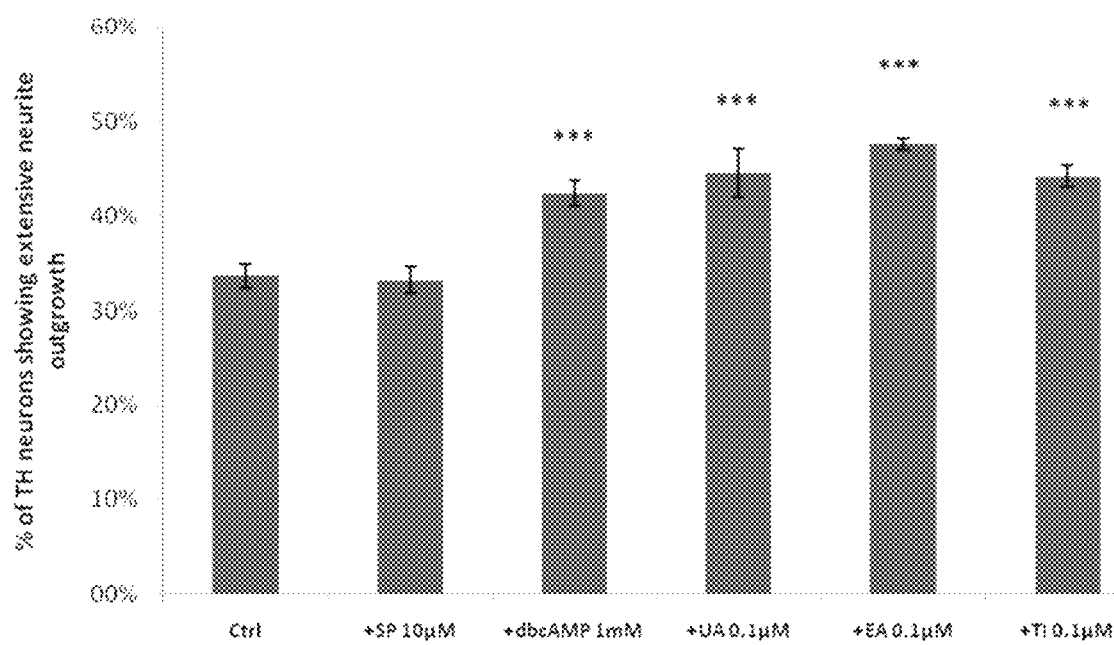

FIG. 11 is a bar graph depicting the percentage of primary dopaminergic TH-positive neurons showing extensive neurite outgrowth (>20 $\mu$m) following treatment with 0.1 $\mu$M of the indicated compounds. SP, SP600125; dbcAMP, dibutyryl cyclic AMP; UA, urolithin A; EA, ellagic acid; T1, tellimagrandin.

Figure 12:
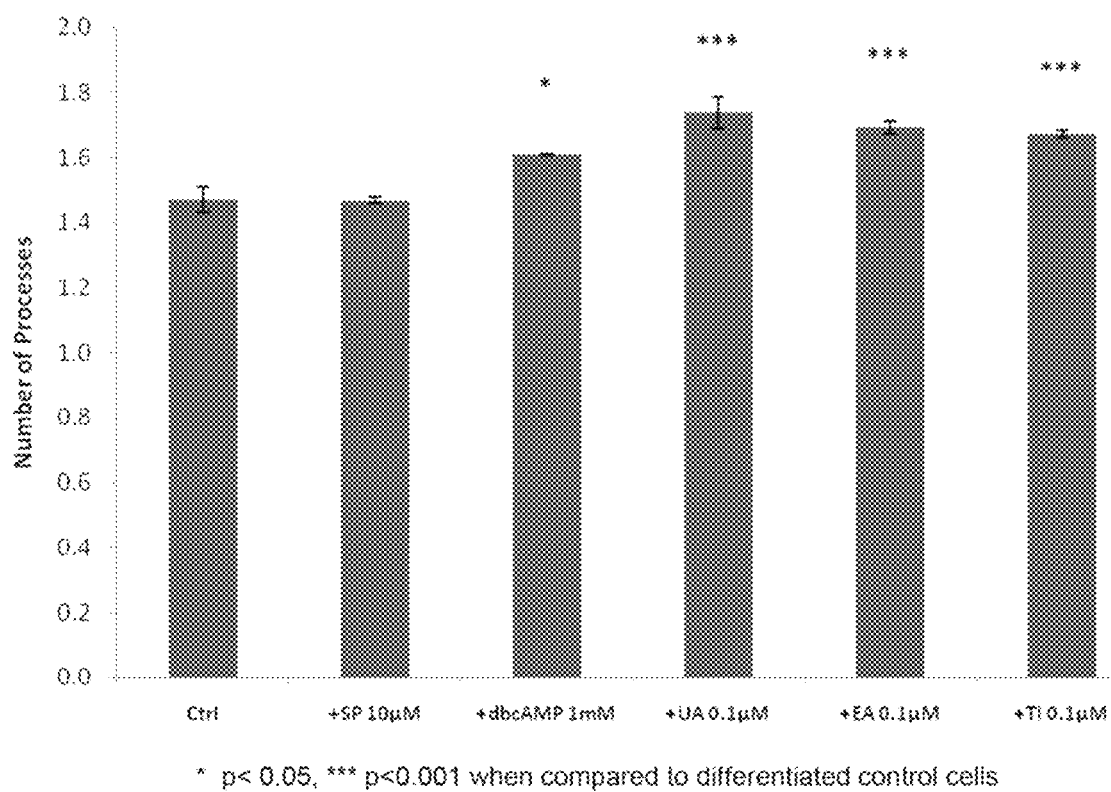

FIG. 12 is a bar graph depicting the mean number of processes formed in primary dopaminergic TH-positive neurons following treatment with 0.1 $\mu$M of the indicated compounds. SP, SP600125; dbcAMP, dibutyryl cyclic AMP; UA, urolithin A; EA, ellagic acid; T1, tellimagrandin.

Figure 13:
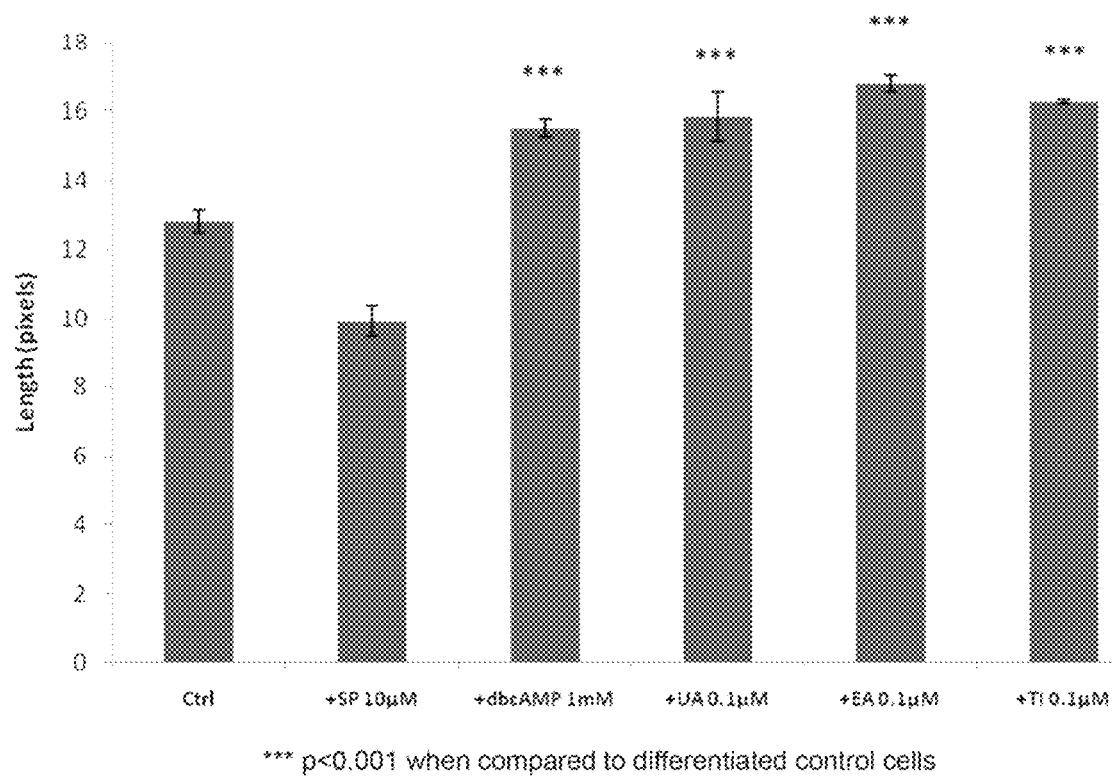

FIG. 13 is a bar graph depicting the maximum process length in primary dopaminergic TH-positive neurons following treatment with 0.1 $\mu$M of the indicated compounds. SP, SP600125; dbcAMP, dibutyryl cyclic AMP; UA, urolithin A; EA, ellagic acid; T1, tellimagrandin.

Figure 14:
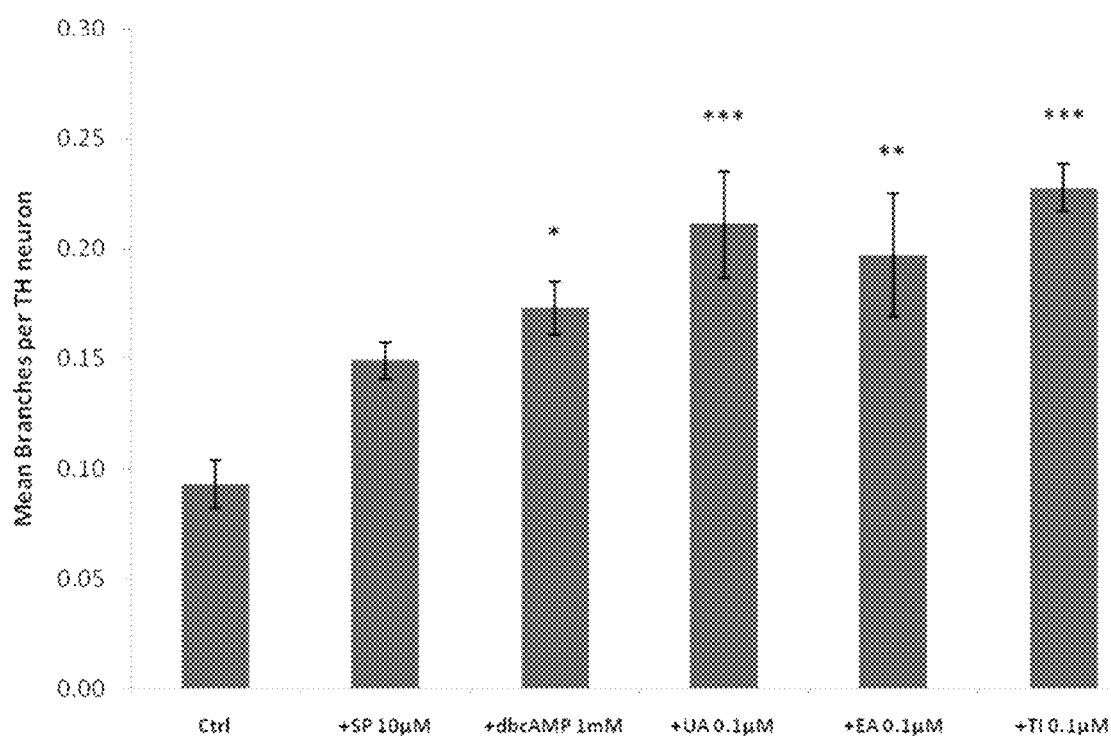

FIG. 14 is a bar graph depicting the mean branches per primary dopaminergic TH-positive neuron following treatment with 0.1 $\mu$M of the indicated compounds. SP, SP600125; dbcAMP, dibutyryl cyclic AMP; UA, urolithin A; EA, ellagic acid; T1, tellimagrandin.

Figure 15:
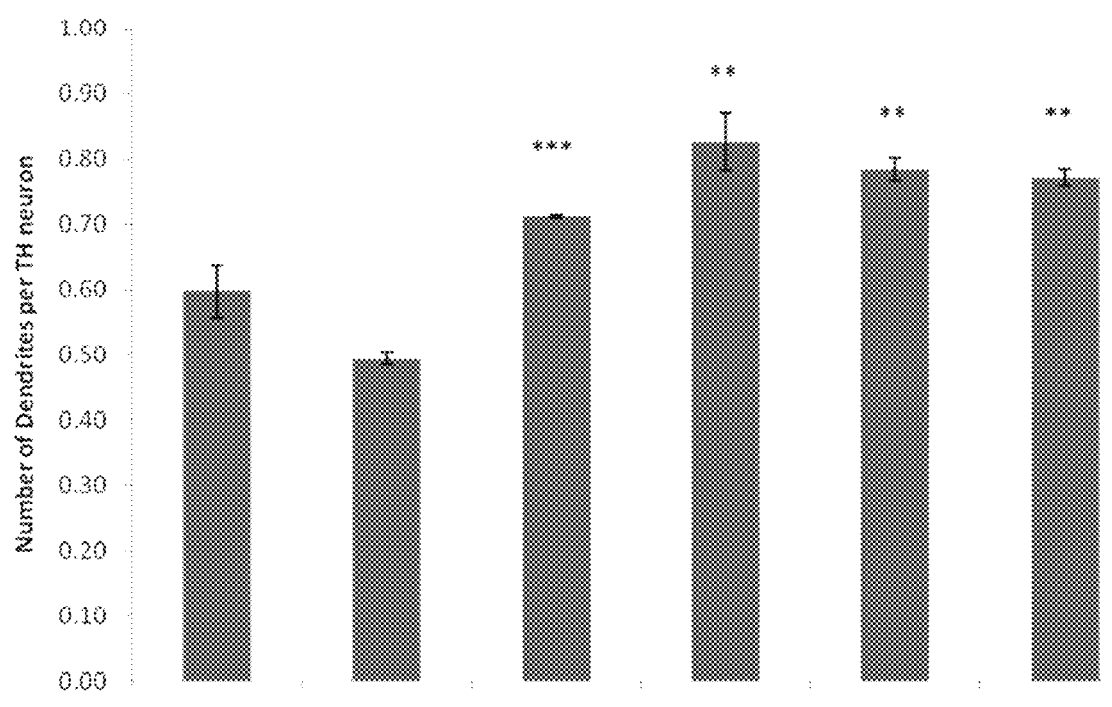

FIG. 15 is a bar graph depicting the mean number of dendrites per primary dopaminergic TH-positive neuron following treatment with 0.1 $\mu$M of the indicated compounds. SP, SP600125; dbcAMP, dibutyryl cyclic AMP; UA, urolithin A; EA, ellagic acid; T1, tellimagrandin.

Figure 16:
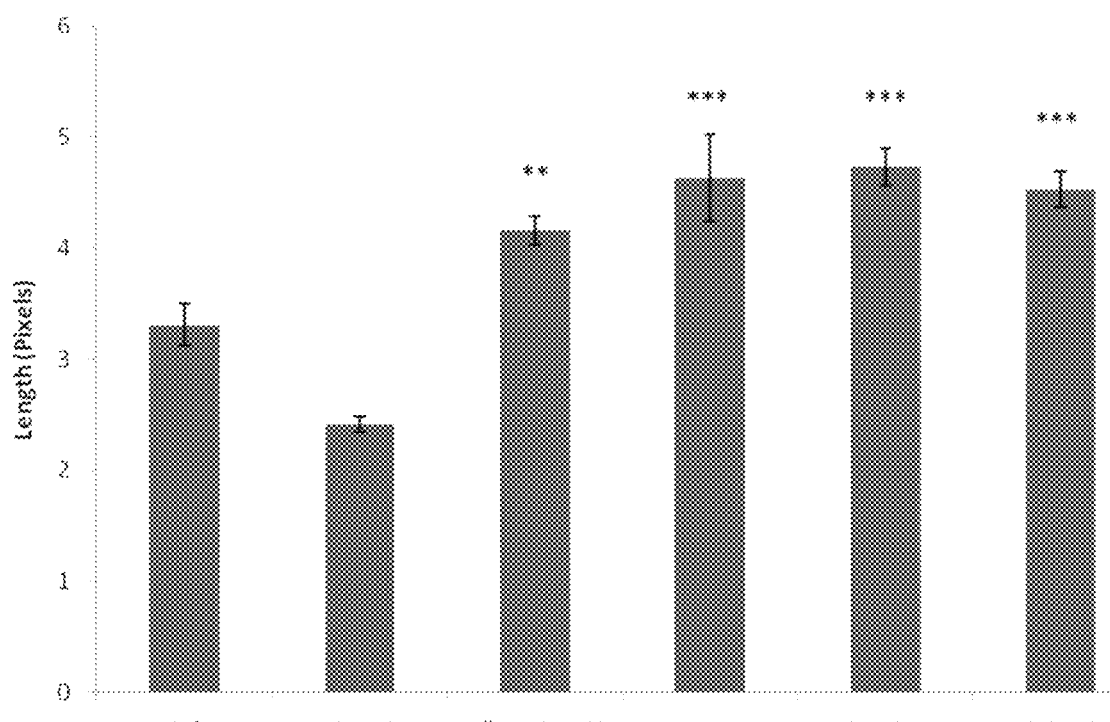

FIG. 16 is a bar graph depicting the mean dendrite length per primary dopaminergic TH-positive neuron following treatment with 0.1 $\mu$M of the indicated compounds. SP, SP600125; dbcAMP, dibutyryl cyclic AMP; UA, urolithin A; EA, ellagic acid; T1, tellimagrandin.

Figure 17A:
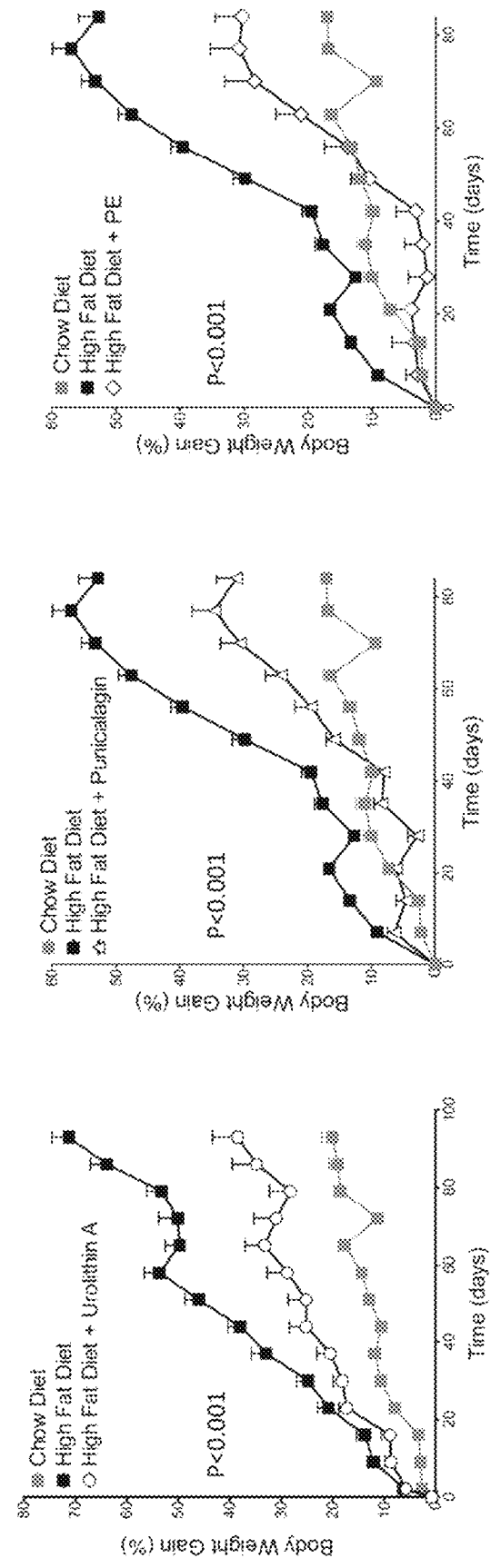

FIG. 17A is a series of three graphs depicting effects of urolithin A, punicalagin, and pomegranate extract (PE) treatment on the onset of obesity in high fat diet (HFD)-fed mice. Urolithin A was administered as food admix; PE and punicalagin were administered by gavage. The figure shows body weight follow-up expressed as percentage increase compared to initial body weight. Group composition: HFD control (food admix): n=10; HFD control (gavage): n=10; HFD plus urolithin A (food admix): n=9; HFD plus punicalagin (gavage): n=8; HFD plus PE (gavage): n=7. Results are expressed as mean±SEM. Results were analyzed by 2-way ANOVA. Values of p are indicated.

Figure 17B:
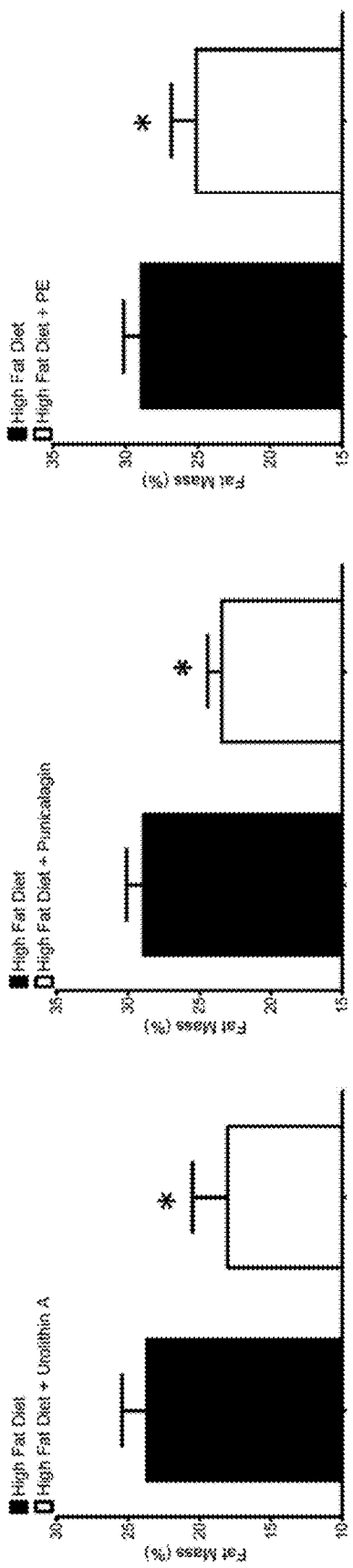

FIG. 17B is a series of three bar graphs depicting effects of urolithin A, punicalagin, and pomegranate extract (PE) treatment on the onset of obesity in high fat diet (HFD)-fed mice. Urolithin A was administered as food admix; PE and punicalagin were administered by gavage. The figure shows percentage fat mass measured by EchoMRI after 5 weeks of treatment. Group composition: HFD control (food admix): n=10; HFD control (gavage): n=10; HFD plus urolithin A (food admix): n=9; HFD plus punicalagin (gavage): n=8; HFD plus PE (gavage): n=7. Results are expressed as mean±SEM. *p<0.05 (Student's t-test).

Figure 17C:
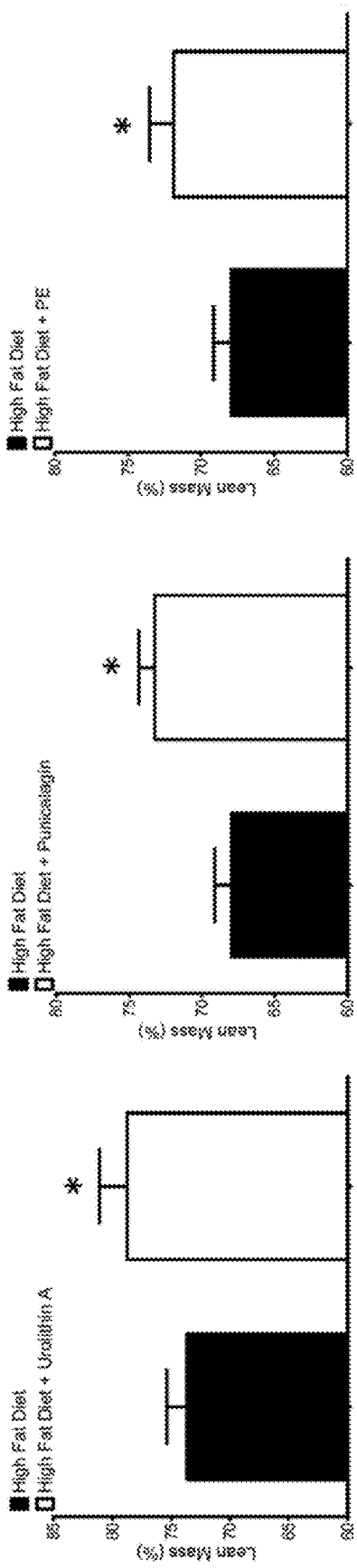

FIG. 17C is a series of three bar graphs depicting effects of urolithin A, punicalagin, and pomegranate extract (PE) treatment on the onset of obesity in high fat diet (HFD)-fed mice. Urolithin A was administered as food admix; PE and punicalagin were administered by gavage. The figure shows percentage lean mass measured by EchoMRI after 5 weeks of treatment. Group composition: HFD control (food admix): n=10; HFD control (gavage): n=10; HFD plus urolithin A (food admix): n=9; HFD plus punicalagin (gavage): n=8; HFD plus PE (gavage): n=7. Results are expressed as mean±SEM. *p<0.05 (Student's t-test).

FIG. 18A is a pair of bar graphs depicting effects of ellagic acid and urolithin A on lean mass in mice fed standard chow diet. The figure shows percentage of lean mass (muscle) measured by EchoMRI after 2 weeks of treatment. Group composition: Chow diet control (food admix): n=8; Chow diet plus ellagic acid (food admix): n=7; Chow diet plus urolithin A (food admix): n=7. Results are expressed as mean±SEM. *p<0.05 (Student's t-test).

FIG. 18B is a pair of bar graphs depicting effects of ellagic acid and urolithin A on fat mass in mice fed standard chow diet. The figure shows percentage of fat mass measured by EchoMRI after 2 weeks of treatment. Group composition: Chow diet control (food admix): n=8; Chow diet plus ellagic acid (food admix): n=7; Chow diet plus urolithin A (food admix): n=7. Results are expressed as mean±SEM. *p<0.05 (Student's t-test).

FIG. 19A is a pair of graphs depicting effects of ellagic acid and urolithin A on oxygen consumption in mice fed standard chow diet. The figure shows follow-up of oxygen consumption over a 20 h period. Filled bars correspond to the dark phase (7 pm to 7 am). The rest corresponds to the light phase. Group composition: Chow diet control (food admix): n=8; Chow diet plus ellagic acid (food admix): n=7; Chow diet plus urolithin A (food admix): n=7. Results are expressed as mean±SEM. Results were analyzed by 2-way ANOVA. Value of p is indicated (Chow diet control vs Chow diet plus treatment).

FIG. 19B is a pair of bar graphs depicting effects of ellagic acid and urolithin A on oxygen consumption in mice fed standard chow diet. The figure shows oxygen consumption represented as the area under the curve (AUC). Group composition: Chow diet control (food admix): n=8; Chow diet plus ellagic acid (food admix): n=7; Chow diet plus urolithin A (food admix): n=7. Results are expressed as mean±SEM. *p<0.05 (Student's t-test).

FIG. 20A is a series of graphs depicting effect of urolithin A, punicalagin, and pomegranate extract (PE) on oxygen consumption in mice fed a high-fat diet (HFD). The figure shows follow-up of oxygen consumption over a 20 h period. Filled bars correspond to the dark phase (7 pm to 7 am). The rest corresponds to the light phase. Group composition: HFD control (food admix): n=10; HFD control (gavage): n=10; HFD plus urolithin A (food admix): n=9; HFD plus punicalagin (gavage): n=8; HFD plus PE (gavage): n=7. Results are expressed as mean±SEM. Results were analyzed by 2-way ANOVA.

FIG. 20B is a series of bar graphs depicting effect of urolithin A, punicalagin, and pomegranate extract (PE) on oxygen consumption in mice fed a high-fat diet (HFD). The figure shows oxygen consumption represented as the area under the curve (AUC). Group composition: HFD control (food admix): n=10; HFD control (gavage): n=10; HFD plus urolithin A (food admix): n=9; HFD plus punicalagin (gavage): n=8; HFD plus PE (gavage): n=7. Results are expressed as mean±SEM. *p<0.05 (Student's t-test).

Figure 21A:
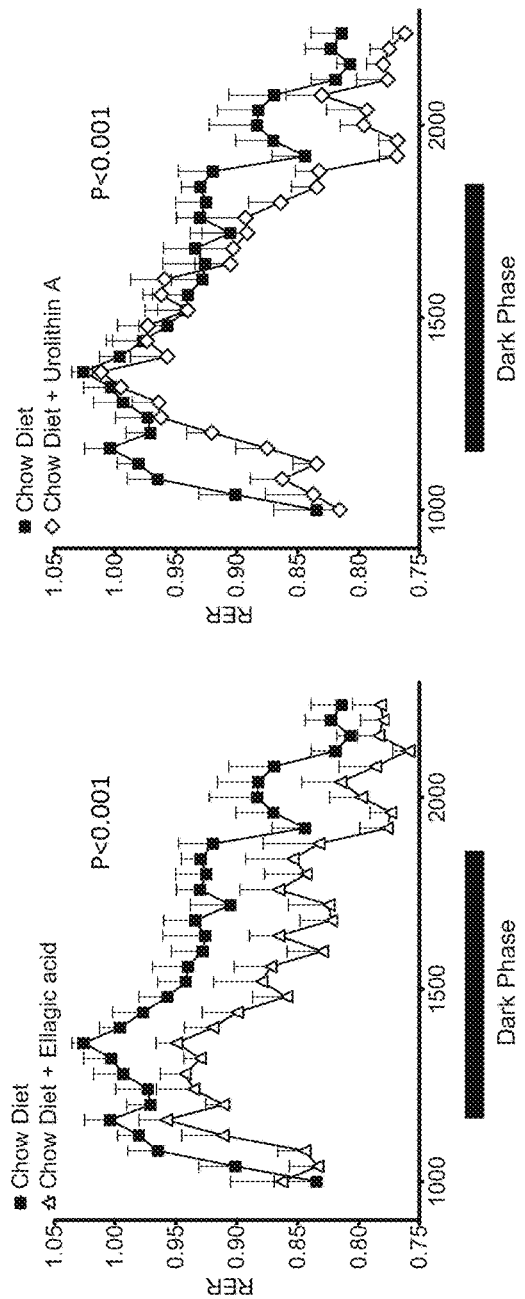

FIG. 21A is a pair of graphs depicting effect of ellagic acid and urolithin A on respiratory exchange ratio (RER) in mice fed standard chow diet. The figure shows follow-up of RER over a 20 h period. Filled bars correspond to the dark phase (7 pm to 7 am). The rest corresponds to the light phase. Group composition: Chow diet control (food admix): n=8; Chow diet plus ellagic acid (food admix): n=7; Chow diet plus urolithin A (food admix): n=7. Results are expressed as mean±SEM. Results were analyzed by 2-way ANOVA. Value of p is indicated (Chow diet control vs Chow diet plus treatment).

Figure 21B:
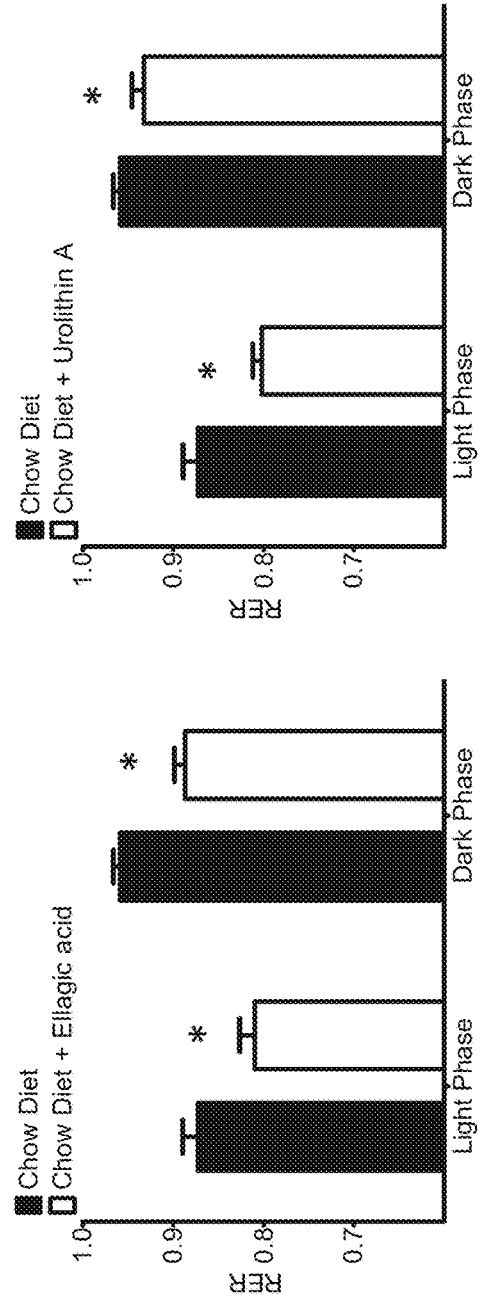

FIG. 21B is a pair of bar graphs depicting effect of ellagic acid and urolithin A on respiratory exchange ratio (RER) in mice fed standard chow diet. The figure shows RER represented as mean RER. Group composition: Chow diet control (food admix): n=8; Chow diet plus ellagic acid (food admix): n=7; Chow diet plus urolithin A (food admix): n=7. Results are expressed as mean±SEM. *p<0.05 (Student's t-test).

Figure 22A:
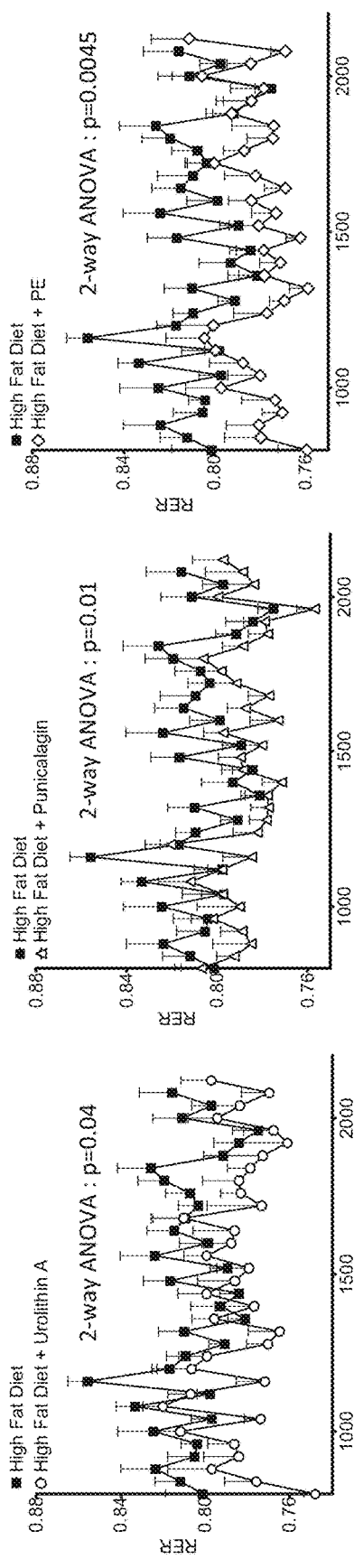

FIG. 22A is a series of graphs depicting effect of urolithin A, punicalagin, and pomegranate extract (PE) on respiratory exchange ratio (RER) in mice fed a high-fat diet (HFD). The figure shows follow-up of RER over a 20 h period. Group composition: HFD control (food admix): n=10; HFD plus urolithin A (food admix): n=9; HFD plus punicalagin (food admix): n=10; HFD plus PE (food admix): n=10. Results are expressed as mean±SEM. Results were analyzed by 2-way ANOVA.

Figure 22B:
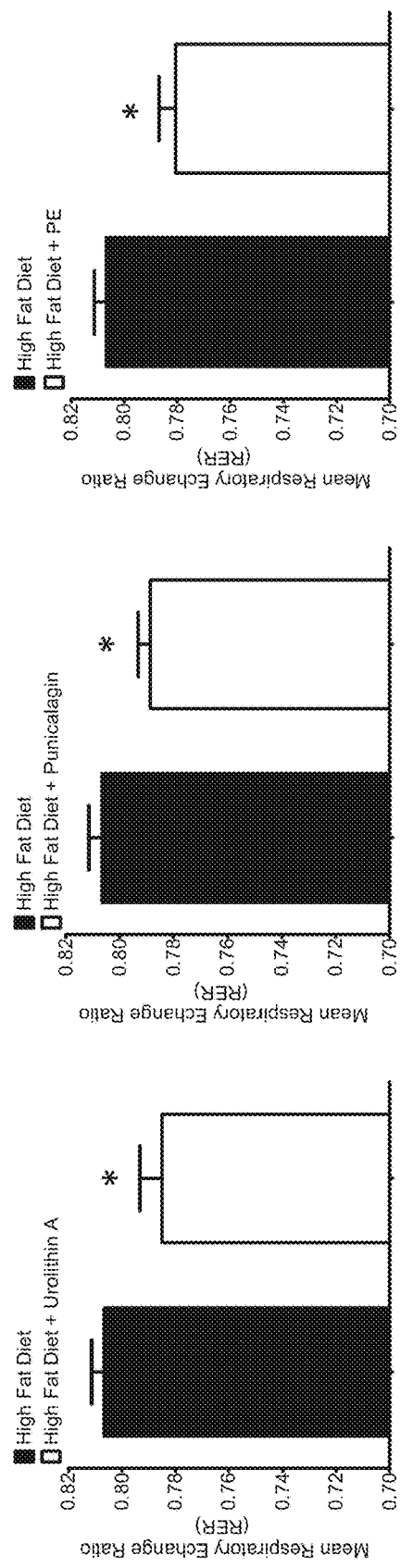

FIG. 22B is a series of bar graphs depicting effect of urolithin A, punicalagin, and pomegranate extract (PE) on respiratory exchange ratio (RER) in mice fed a high-fat diet (HFD). The figure shows RER represented as the mean RER. Group composition: HFD control (food admix): n=10; HFD plus urolithin A (food admix): n=9; HFD plus punicalagin (food admix): n=10; HFD plus PE (food admix): n=10. Results are expressed as mean±SEM. *p<0.05 (Student's t-test).

Figure 23A:
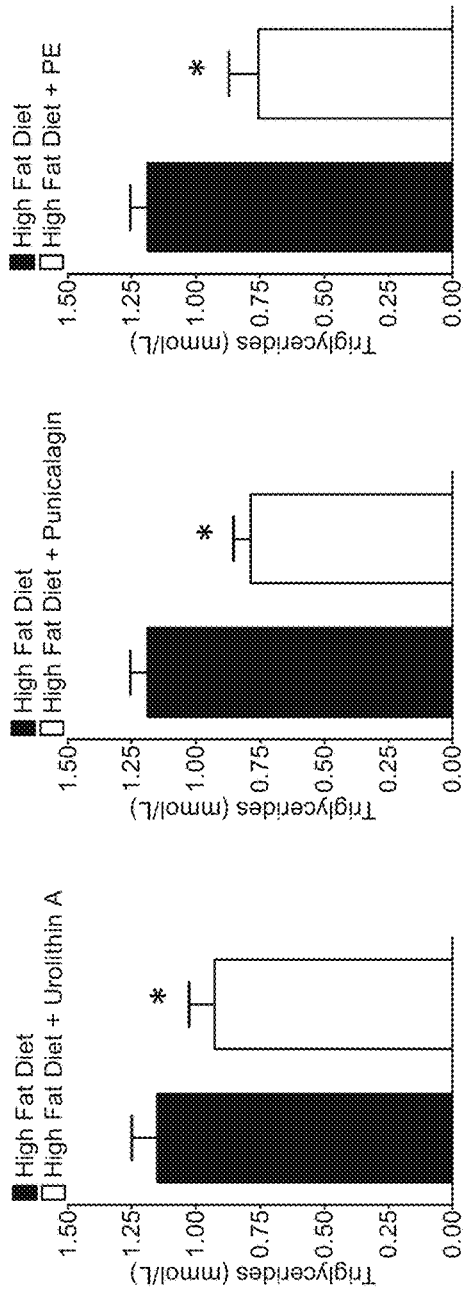

FIG. 23A is a series of graphs depicting effect of urolithin A, punicalagin, and pomegranate extract (PE) on triglycerides in mice fed a high-fat diet (HFD). The figure shows plasma levels of triglycerides in HFD-fed mice treated for 14 weeks. Group composition: HFD control (food admix): n=10; HFD control (gavage): n=10; HFD plus urolithin A (food admix): n=9; HFD plus punicalagin (gavage): n=8;

HFD plus PE (gavage): n=7. Results are expressed as mean±SEM. *p<0.05 (Student's t-test).

Figure 23B:
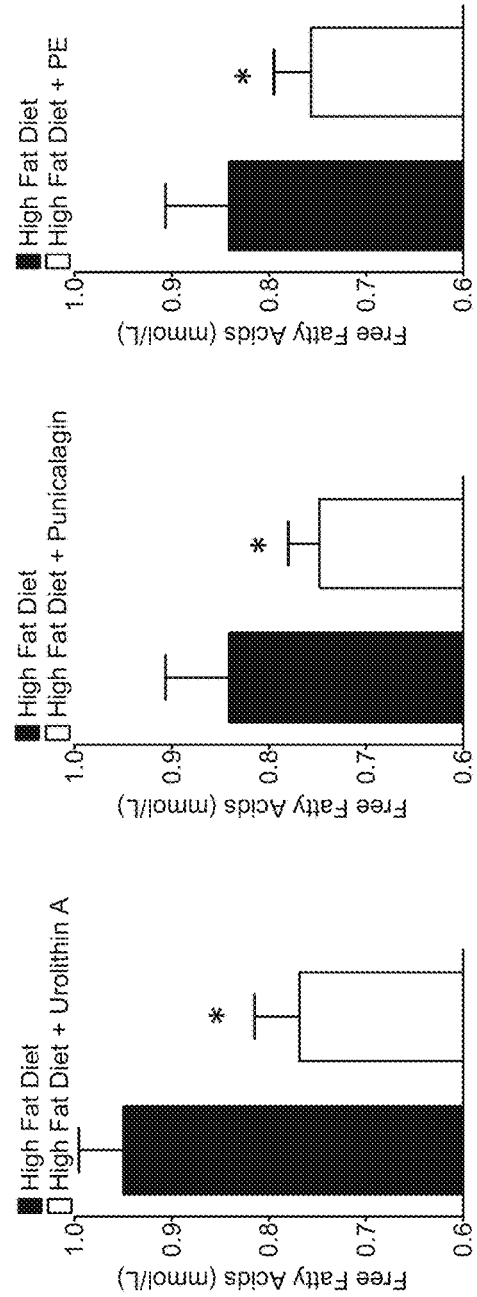

FIG. 23B is a series of graphs depicting effect of urolithin A, punicalagin, and pomegranate extract (PE) on free fatty acids in mice fed a high-fat diet (HFD). The figure shows plasma levels of free fatty acids in HFD-fed mice treated for 14 weeks. Group composition: HFD control (food admix): n=10; HFD control (gavage): n=10; HFD plus urolithin A (food admix): n=9; HFD plus punicalagin (gavage): n=8; HFD plus PE (gavage): n=7. Results are expressed as mean±SEM. *p<0.05 (Student's t-test).

Figure 24B:
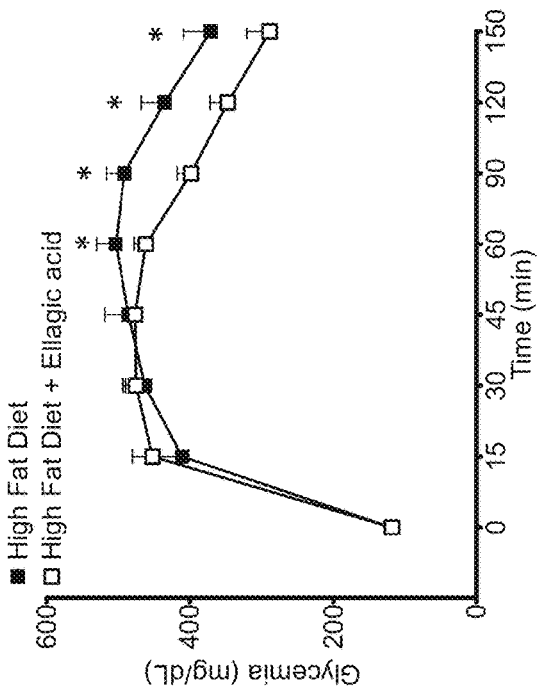
Figure 24A:
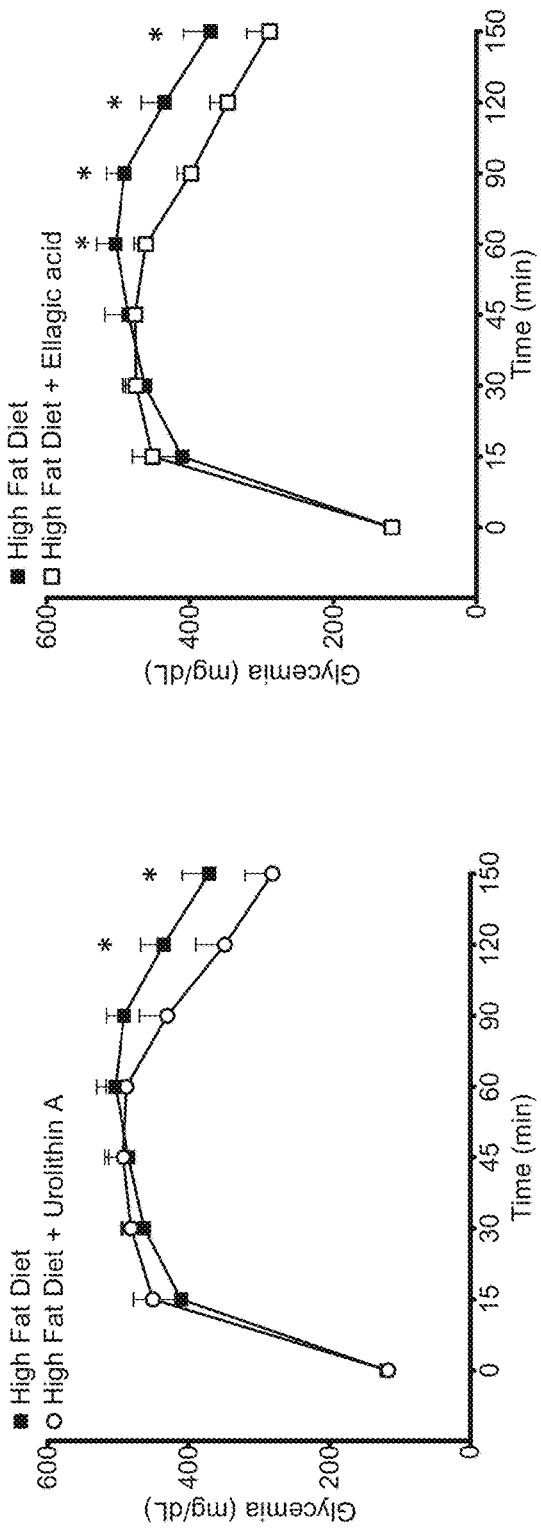

FIG. 24A is a graph depicting effect of urolithin A on glycemia in mice fed a high-fat diet (HFD). The figure shows glucose tolerance test in HFD-fed mice treated by food admix with urolithin A for 10 weeks. Group composition: HFD control (food admix): n=10; HFD plus urolithin A (food admix): n=9. Results are expressed as mean±SEM. *p<0.05 (Student's t-test).

FIG. 24B is a graph depicting effect of ellagic acid on glycemia in mice fed a high-fat diet (HFD). The figure shows glucose tolerance test in HFD-fed mice treated by food admix with ellagic acid for 10 weeks. Results are expressed as mean±SEM. *p<0.05 (Student's t-test).

Figure 24C:
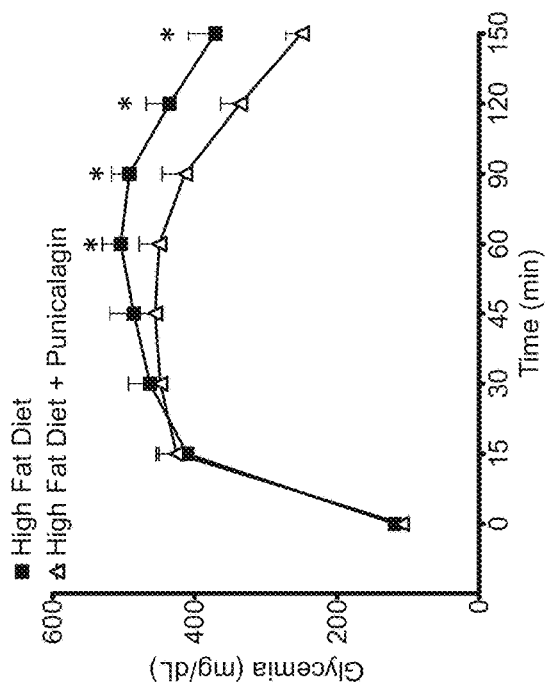

FIG. 24C is a graph depicting effect of punicalagin on glycemia in mice fed a high-fat diet (HFD). The figure shows glucose tolerance test in HFD-fed mice treated by food admix with punicalagin for 10 weeks. Group composition: HFD control (food admix): n=10; HFD plus punicalagin (food admix): n=10. Results are expressed as mean±SEM. *p<0.05 (Student's t-test).

Figure 25B:
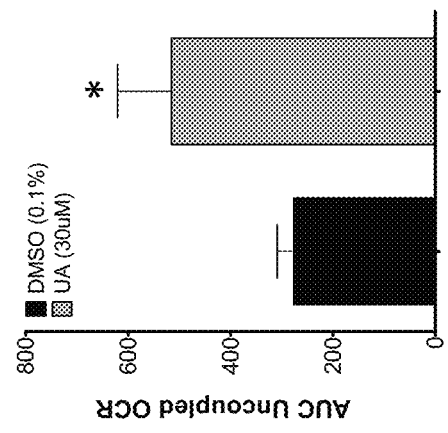
Figure 25A:
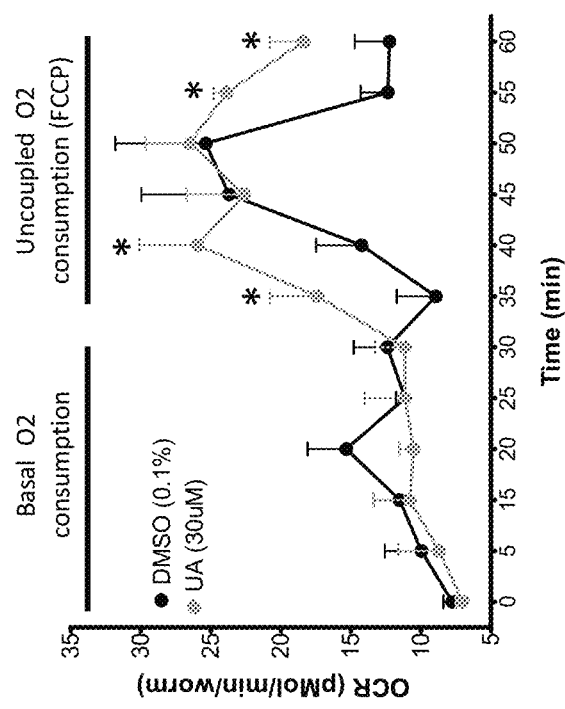

FIG. 25A is a line graph depicting effect of urolithin A (UA) on basal and uncoupled respiration (oxygen consumption) in old (10-day-old) *C. elegans*. The figure shows basal and uncoupled respiration (FCCP) in 10-day-old control worms treated with 0.1% DMSO and 10 day-old-worms treated with 30 µM urolithin A in 0.1% DMSO. Results are expressed as mean±SEM. *p<0.05 (Student's t-test). OCR, oxygen consumption rate.

FIG. 25B is a bar graph depicting effect of urolithin A (UA) on uncoupled respiration (oxygen consumption) in old (10-day-old) *C. elegans*. The figure shows representative area under the curve (AUC) of uncoupled (FCCP) respiration in 10-day-old control worms treated with vehicle (0.1% DMSO) or 30 µM urolithin A in 0.1% DMSO. Results are expressed as mean±SEM. *p<0.05 (Student's t-test). OCR, oxygen consumption rate.

Figure 26:
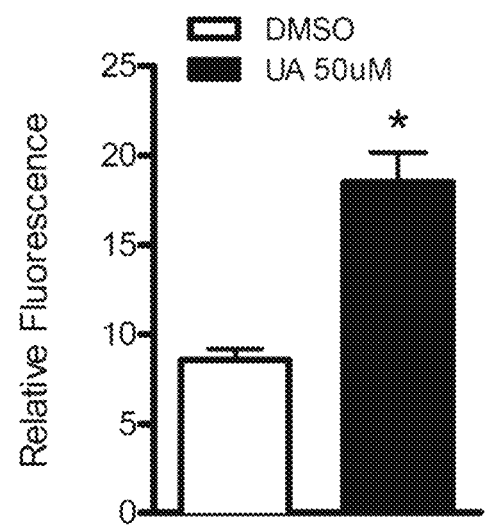

FIG. 26 is a bar graph depicting the effect of urolithin A on mitochondria in muscle of *C. elegans*. Transgenic *C. elegans* strain SJ4103 shows fluorescence due to muscle-specific expression of green fluorescent protein (GFP) which is targeted to the mitochondria membrane. Mitochondria presence in the muscle of the *C. elegans* is shown by an increase in fluorescence. Results are expressed as mean±SEM. *p=0.0014 (Student's t-test).

Figure 27:
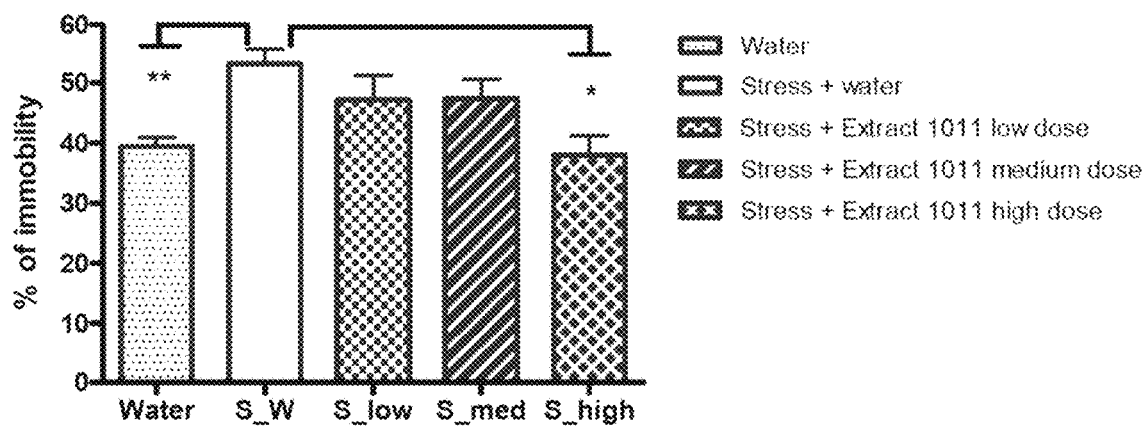

FIG. 27 is a bar graph depicting the mobility of mice subjected to chronic stress with or without treatment with pomegranate extract.

Figure 28:

FIG. 28 is a bar graph depicting the extent of a "freezing" response of mice in an anxiety-inducing context with or without treatment with pomegranate extract.

Figure 29:
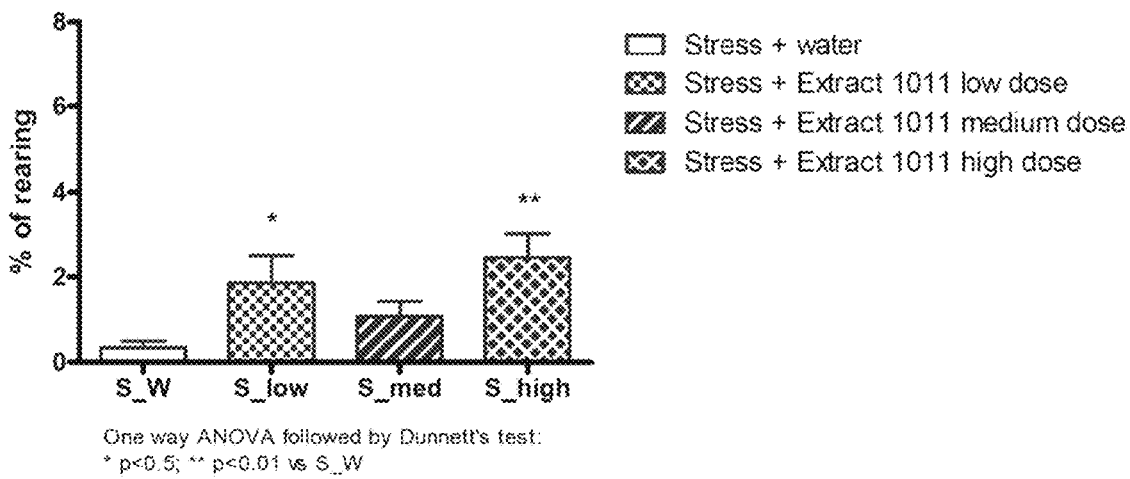

FIG. 29 is a bar graph depicting the effect on mice of administration of pomegranate extract on the extent of anxiety-induced inhibition of rearing.

Figure 30:
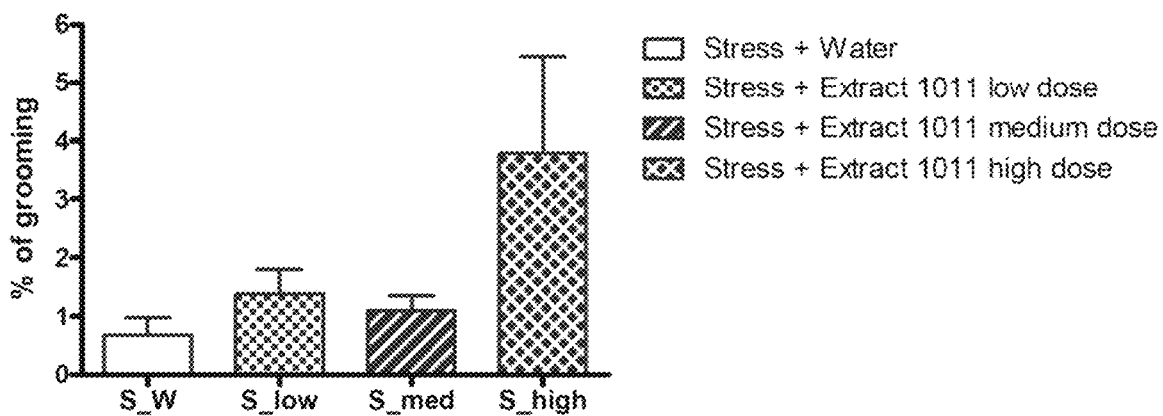

FIG. 30 is a bar graph depicting the effect of the administration of pomegranate extract on the extent of anxiety-induced inhibition of grooming in mice.

Figure 31:
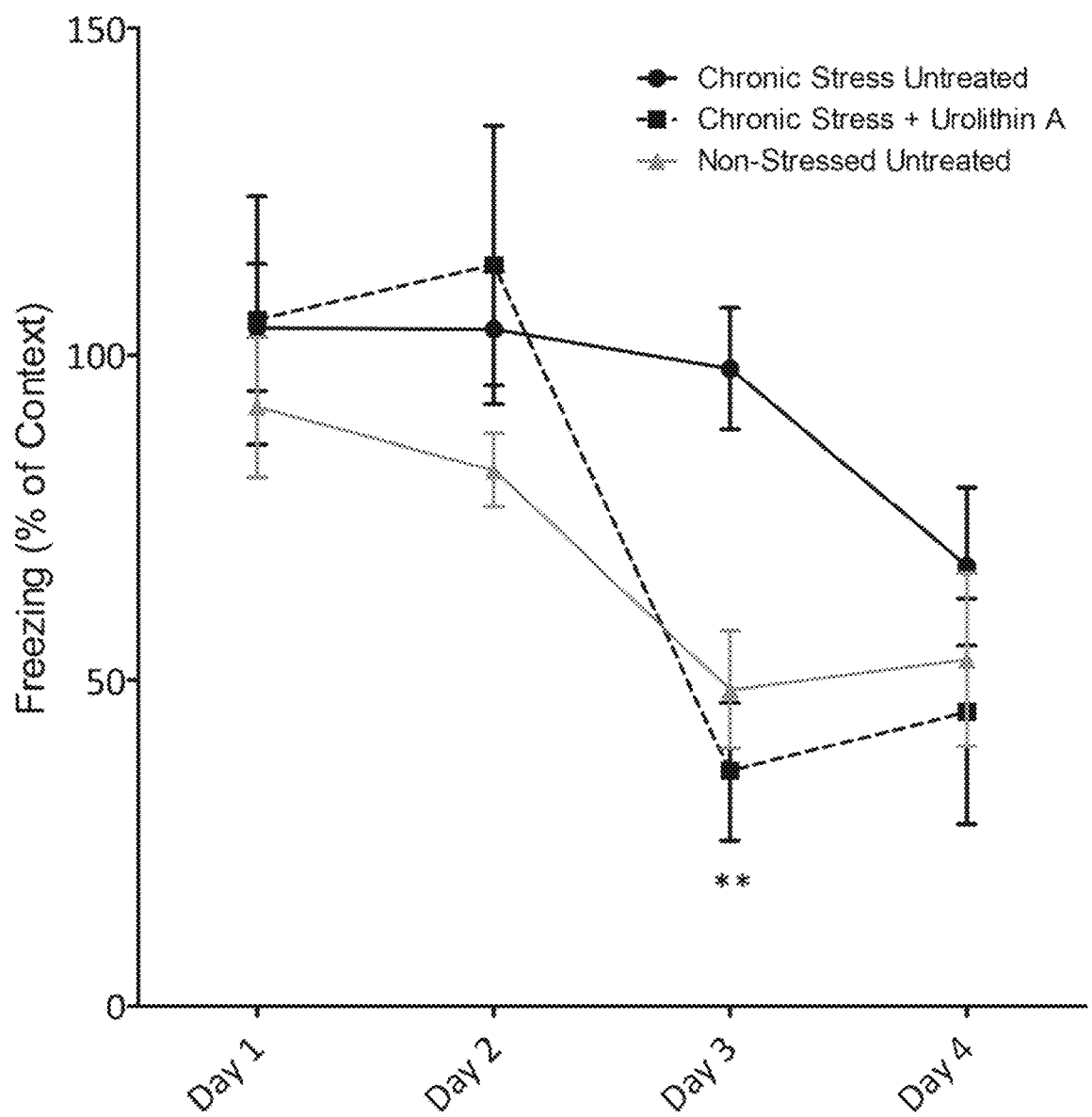

FIG. 31 is a line graph depicting the extinction of a memory to a particular adverse context when repeatedly exposed to the context in the absence of the adverse effect. Data is shown for mice that have undergone early-life stress, normally reared control mice, and mice that have undergone early-life stress but are treated with the ellagitannin punicalagin. Freezing (%) is expressed as a percentage of the freezing time during the initial exposure to the context.

Figure 32:
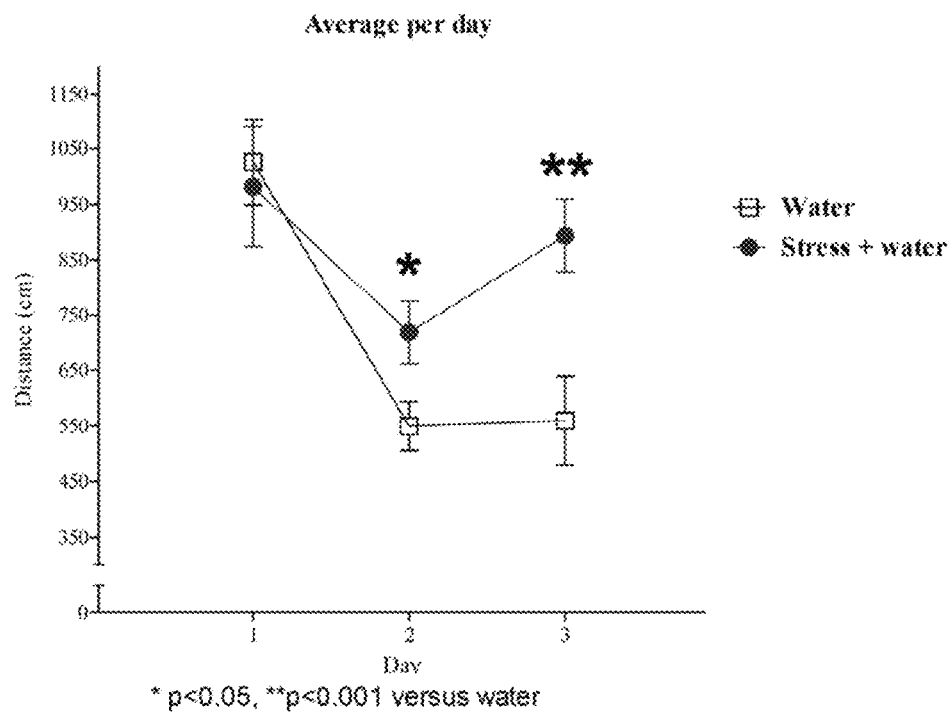

FIG. 32 is a graph depicting the effect on mice of chronic stress on effective learning in the Morris water maze.

Figure 33:
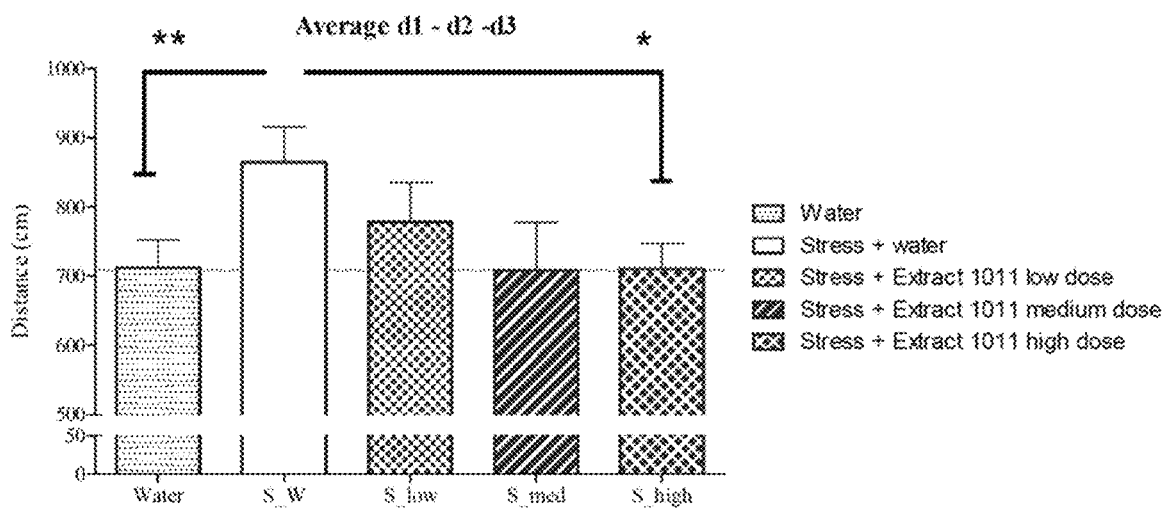

FIG. 33 is a bar graph depicting the effect on chronically stressed mice of administration of pomegranate extract on learning performance in the Morris water maze.

Figure 34:
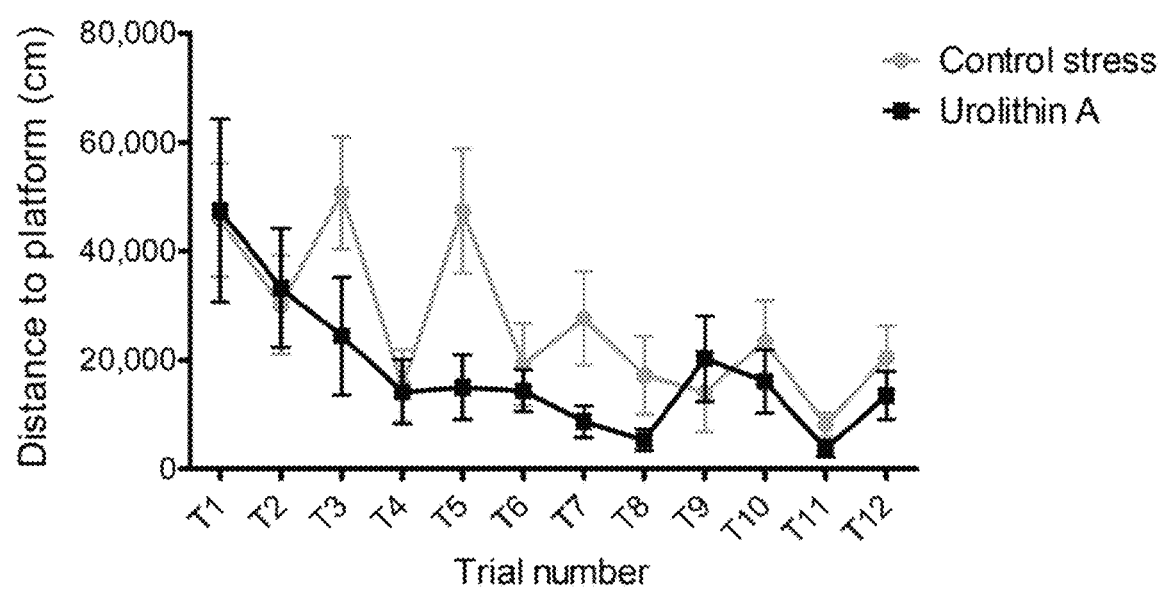

FIG. 34 is a graph depicting the accumulated distance from a hidden platform for several trials during the training phase in the Morris water maze, a measurement of cognitive learning. Data is shown for mice that have undergone early-life stress, normally reared control mice, and mice that have undergone early-life stress but are treated with the ellagitannin punicalagin. Distance to platform is the sum of accumulated distances between the mouse and the hidden platform for all intervals measured (25 intervals/sec) during the observation period (60 sec).

Figure 35:
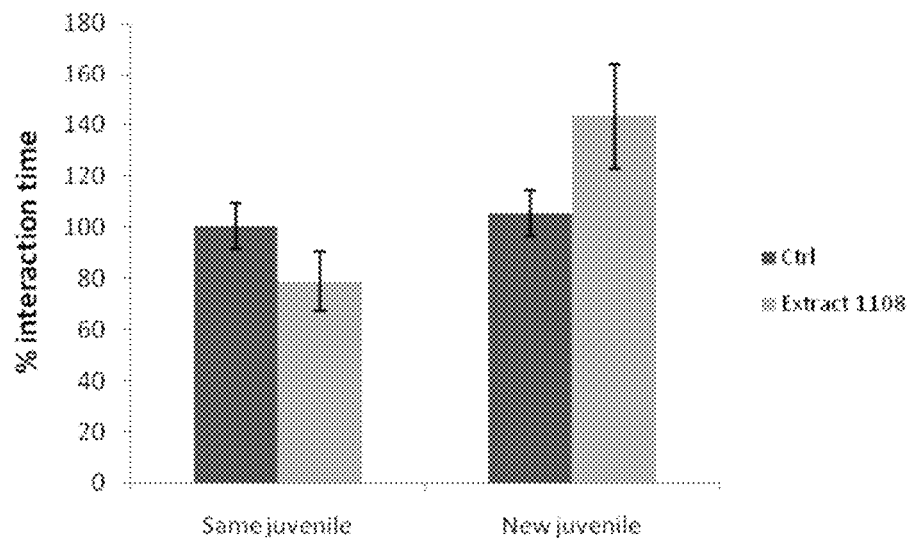

FIG. 35 is a bar graph depicting memory of aged rats in a social recognition test when treated with either the pomegranate extract 1108 or a control (Ctrl).

Figure 36:
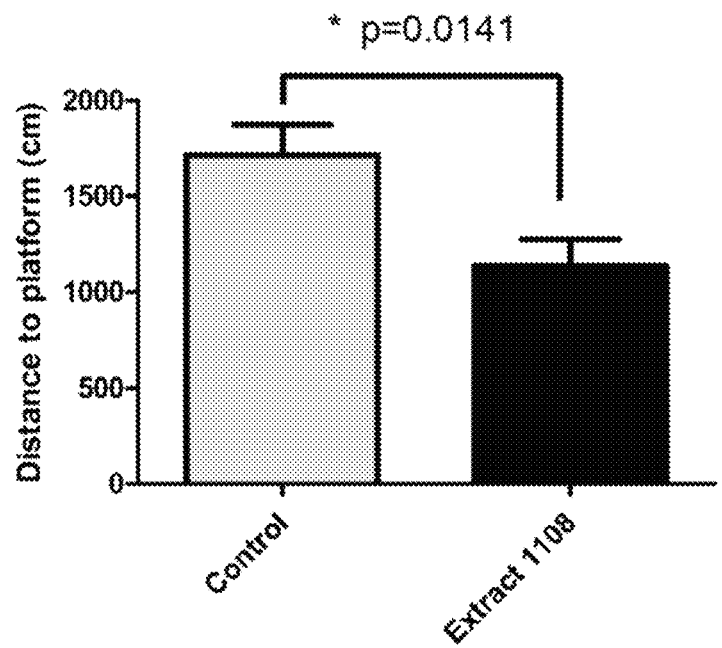

FIG. 36 is a bar graph depicting Morris water maze results for aged rats treated with pomegranate extract 1108 or control (Ctrl).

Figure 37:
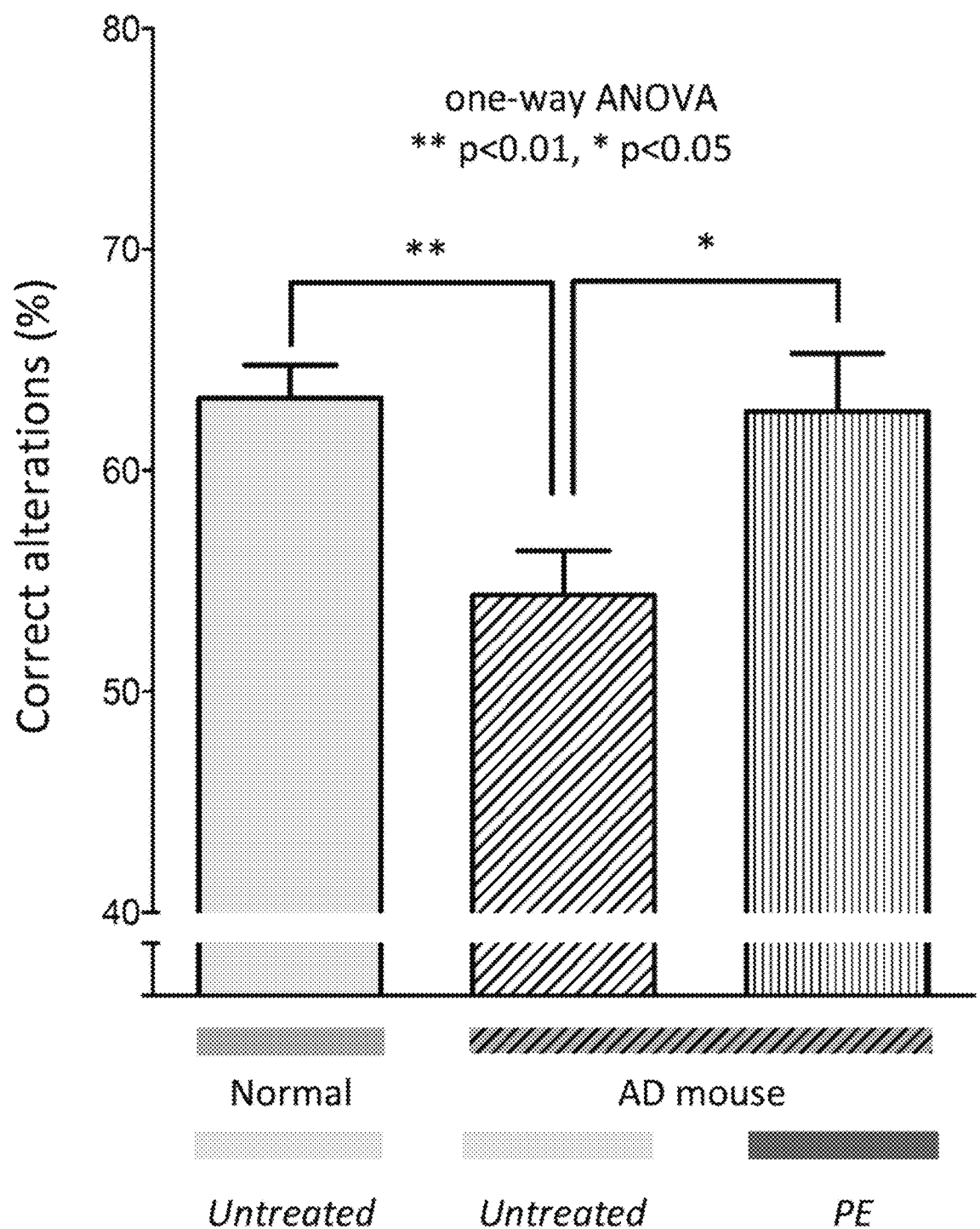

FIG. 37 is a bar graph depicting the percent of correct alterations in a Y maze for the Alzheimer disease mouse model 5XFAD, both treated and untreated, as well as normal control mice. Significance: **p<0.01, *p<0.05, one way ANOVA.

Figure 38:
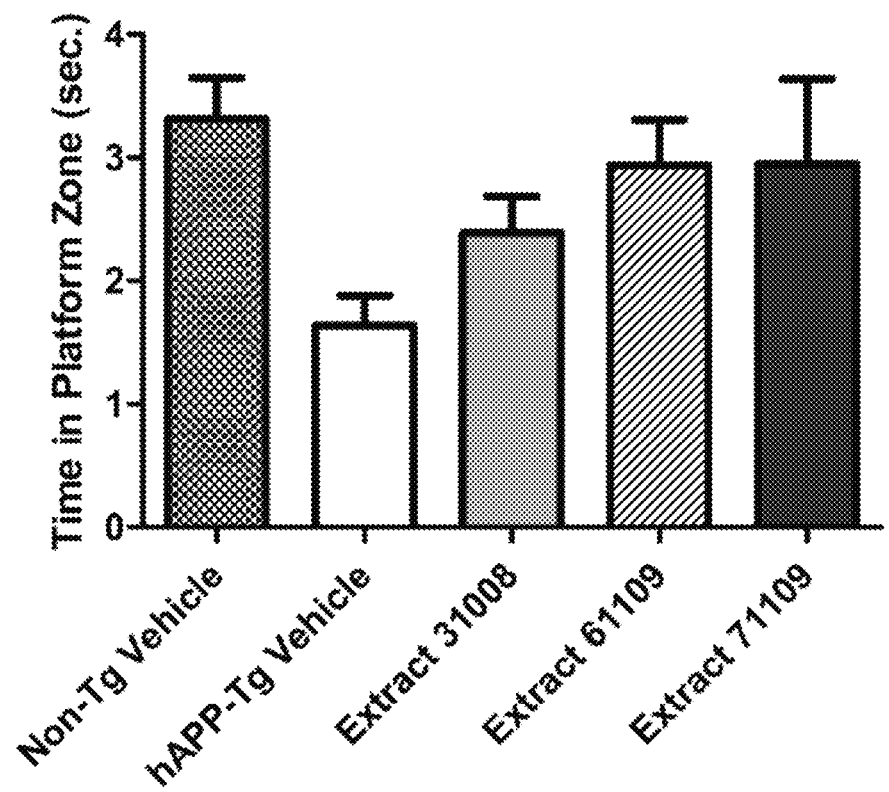

FIG. 38 is a bar graph depicting Morris water maze results for transgenic mice modeling Alzheimer's disease (hAPP-Tg) treated with pomegranate-derived extracts 31008, 61109, 71109, or control (Vehicle). Also shown are results for wild-type mice (Non-Tg) treated with control (Vehicle).

Figure 39:
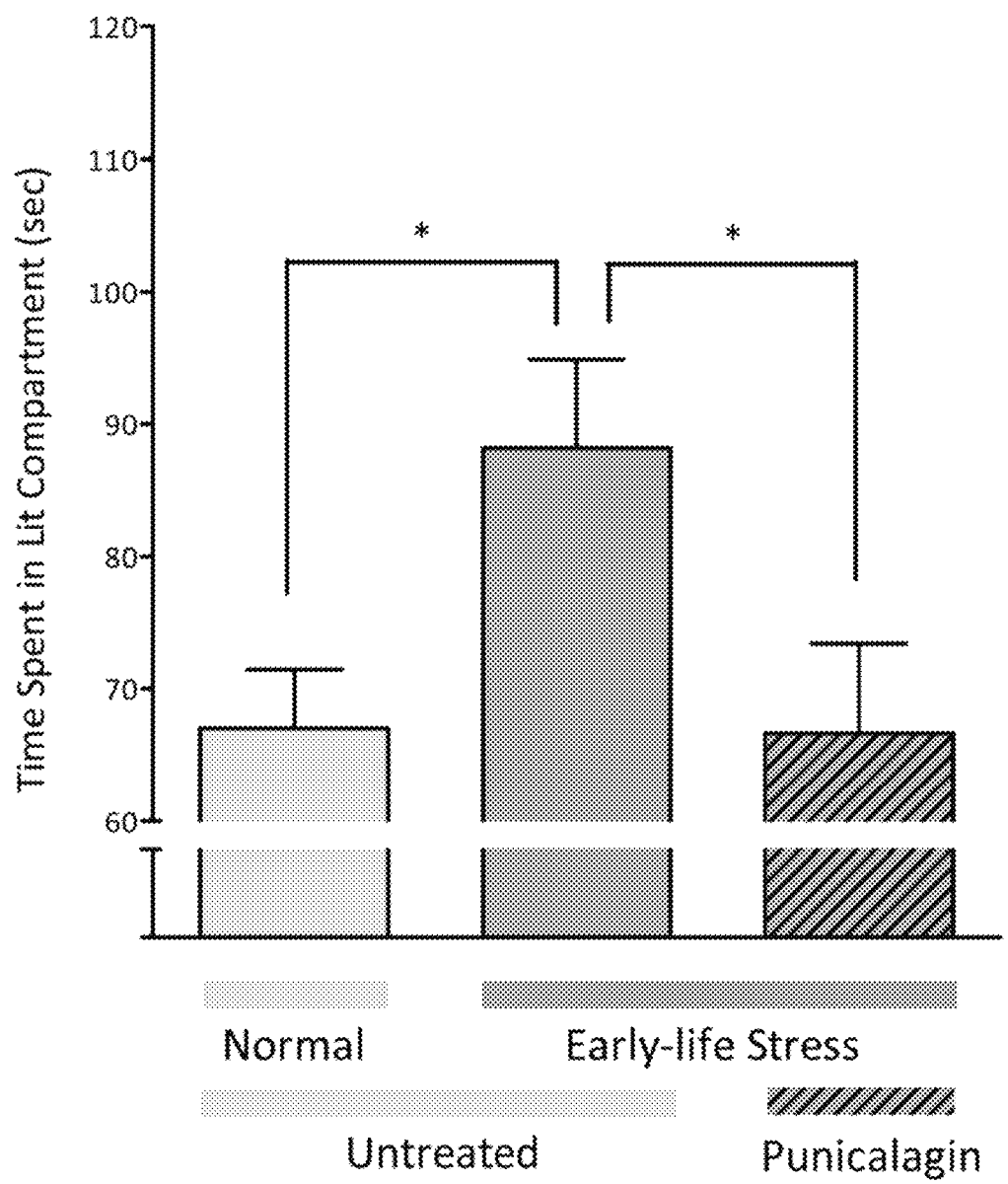

FIG. 39 is a bar graph depicting dark/light box results for mice that have undergone early-life stress versus normally reared control mice, and mice having undergone early-life stress and treated with the ellagitannin punicalagin. Results are expressed as mean±SEM. Significance: *p<0.05, (Student's t-test).

Figure 40:
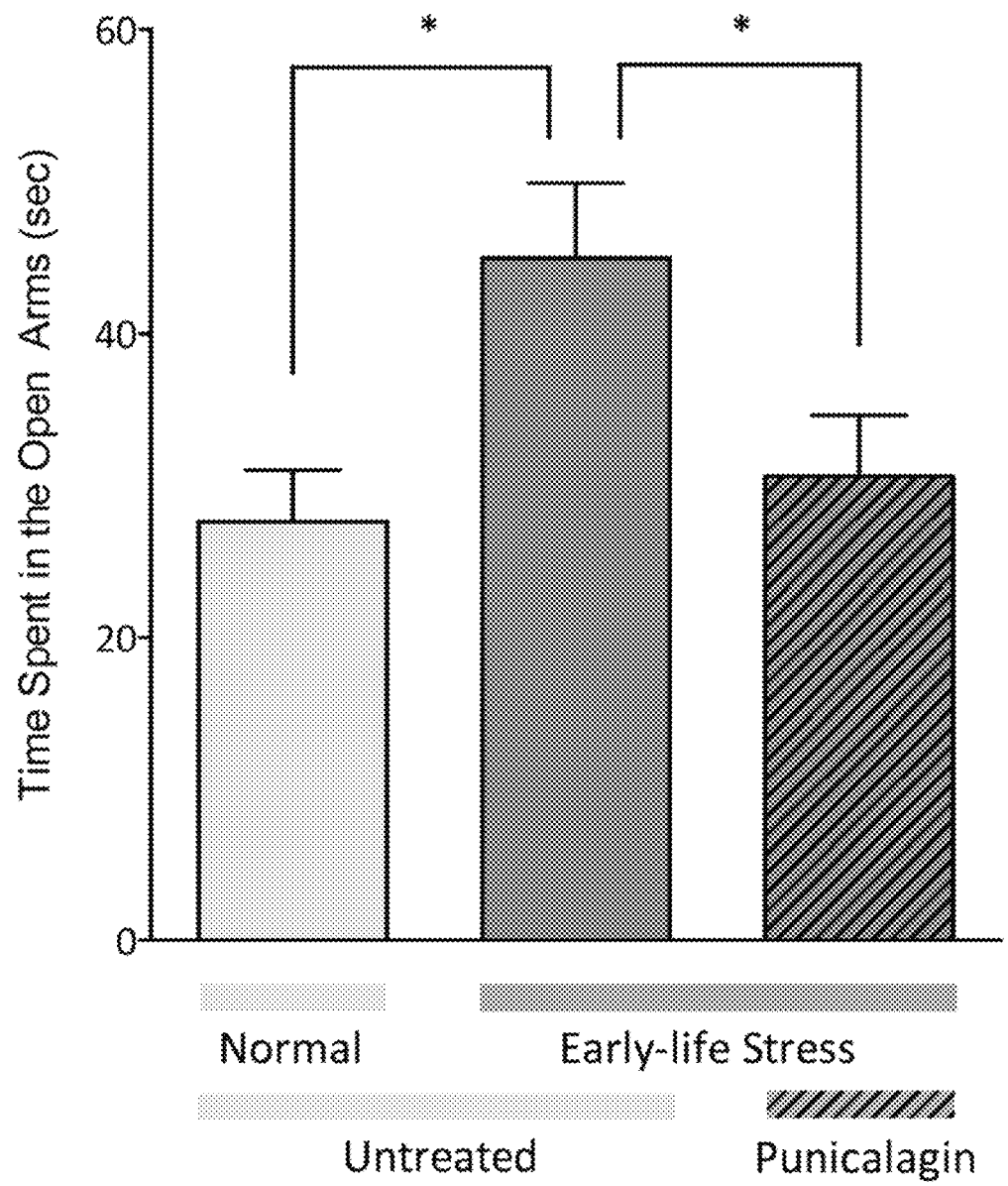

FIG. 40 is a bar graph depicting results for the elevated O-maze for mice that have undergone early-life stress versus normally reared control mice, and mice having undergone early-life stress and treated with the ellagitannin punicalagin. Results are expressed as mean±SEM. Significance: *p<0.05, (Student's t-test).

Figure 41:
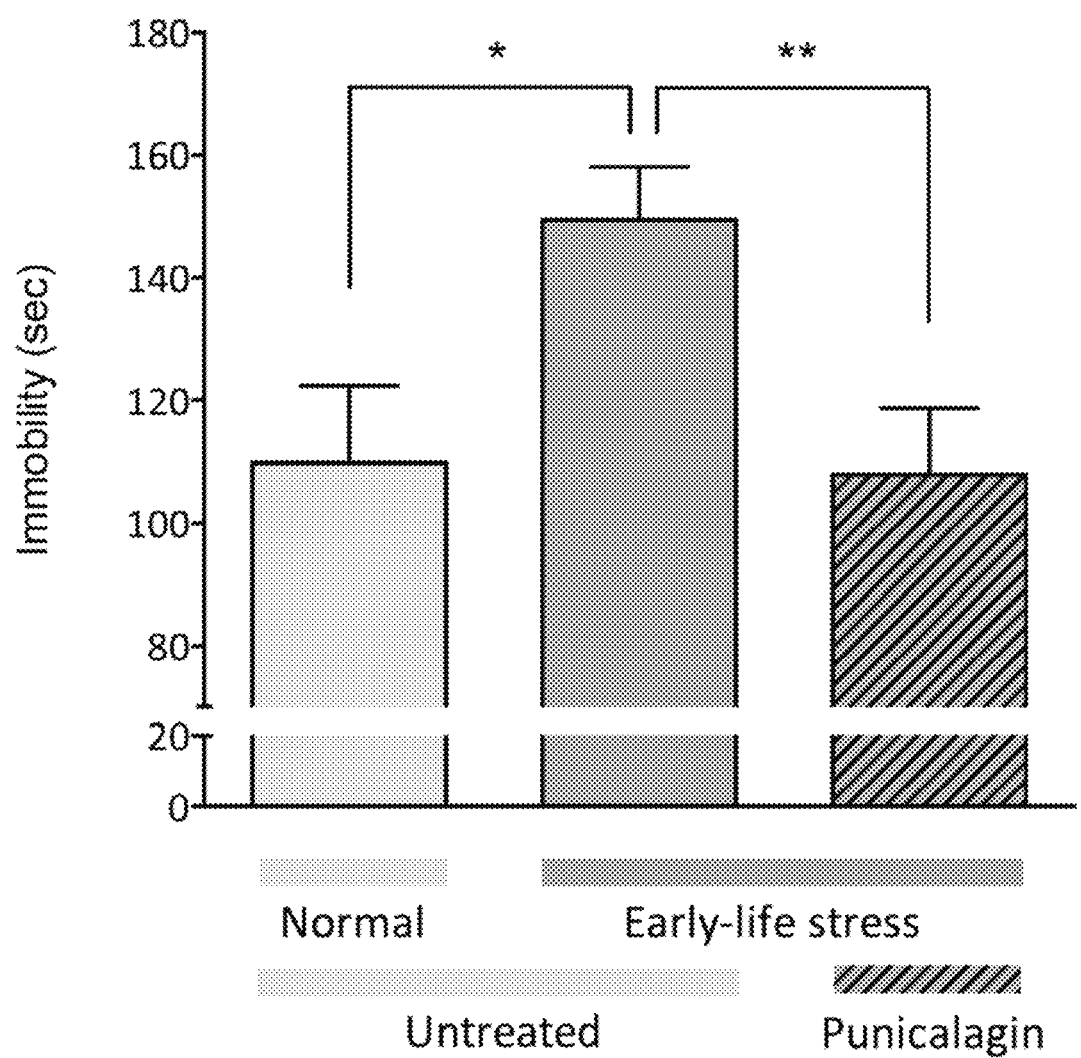

FIG. 41 is a bar graph depicting results for the forced swim test for mice that have undergone early-life stress versus normally reared control mice, and mice having undergone early-life stress and treated with the ellagitannin punicalagin. Results are expressed as mean±SEM. Significance: *p<0.05, **p<0.01 (Student's t-test).

Figure 42:
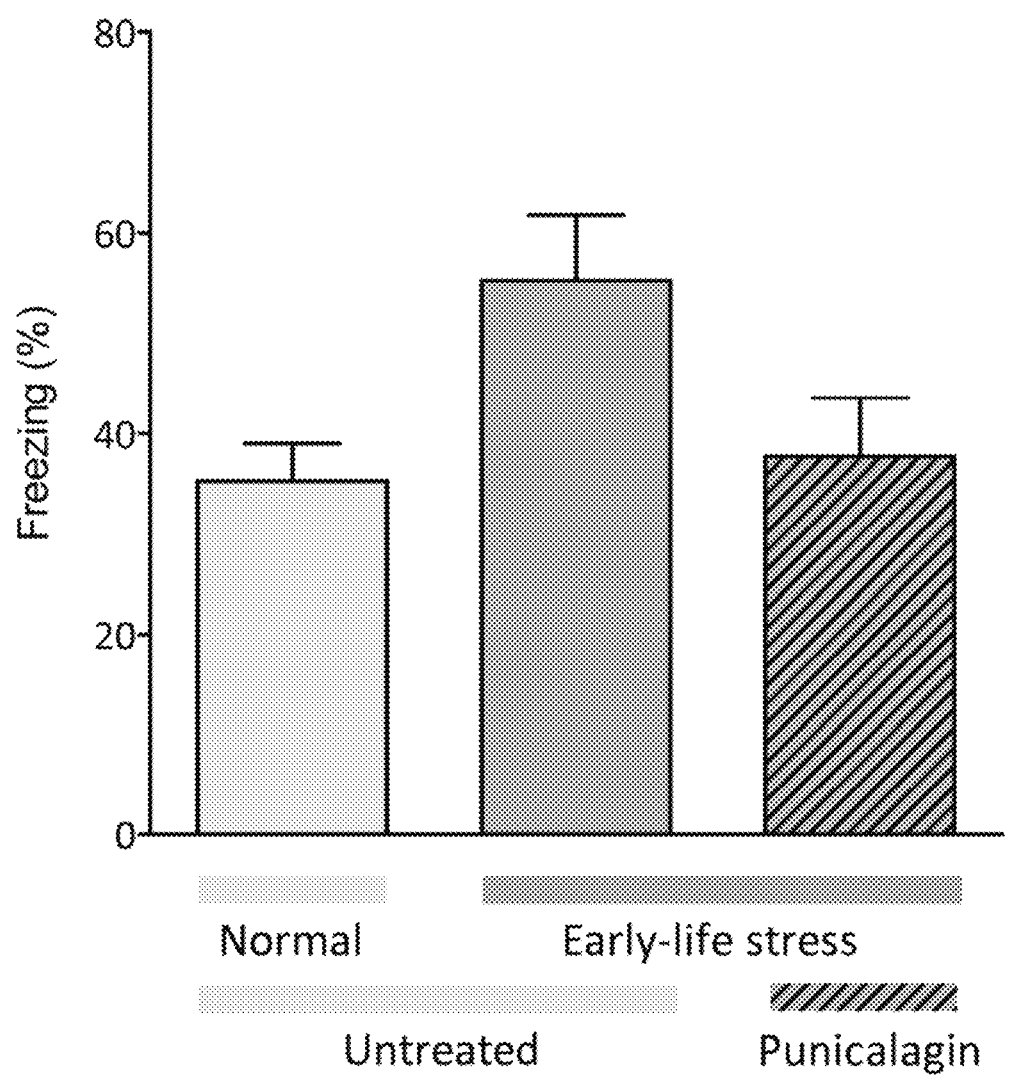

FIG. 42 is a bar graph depicting results for the training in the contextual fear conditioning paradigm during the first mild shock which takes place at 4 min. Results are shown for mice that have undergone early-life stress versus normally reared control mice, and mice that have undergone early-life stress and treated with the ellagitannin punicalagin. Results are expressed as mean±SEM.

Figure 43:
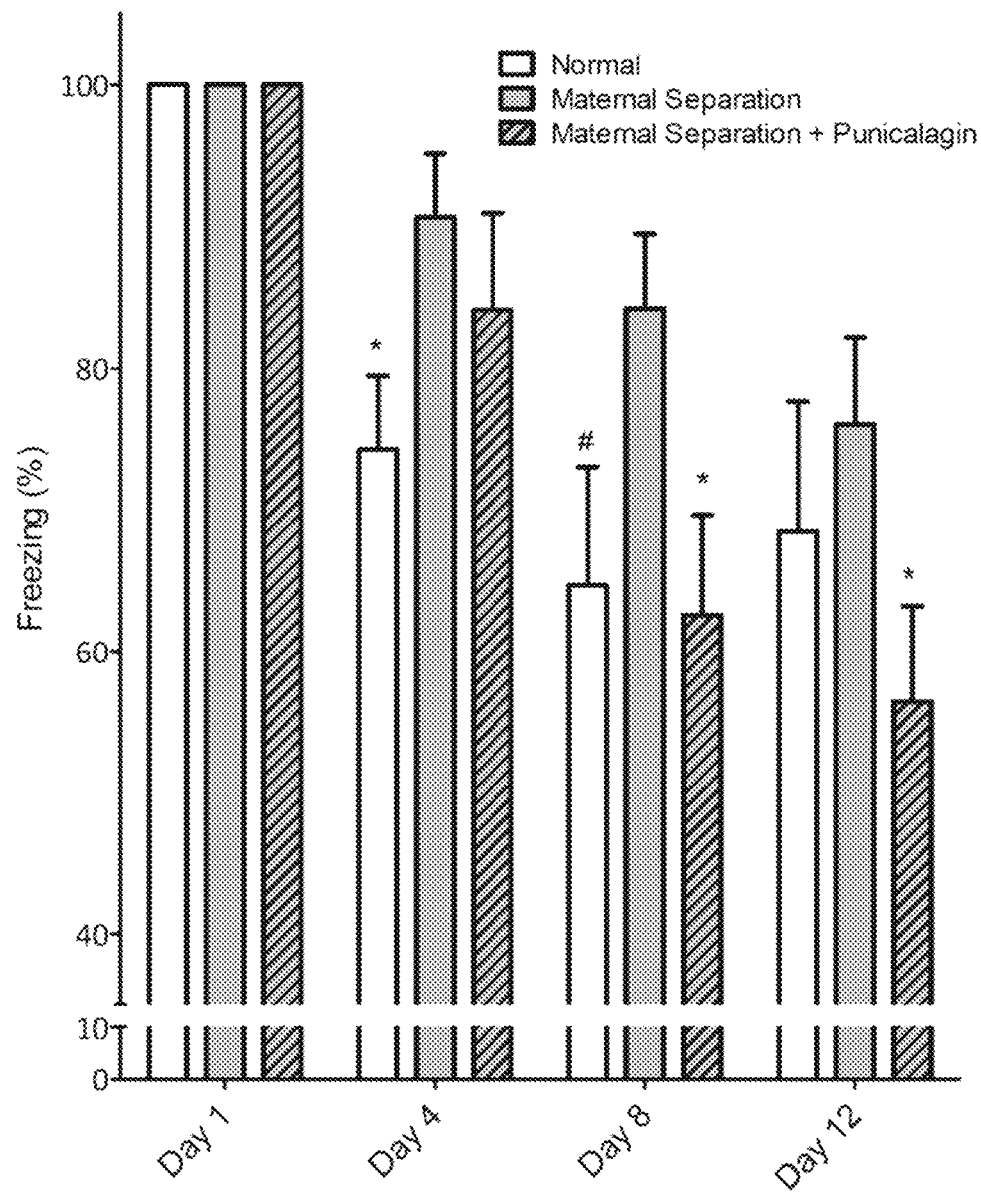

FIG. 43 is a bar graph depicting the extinction of a memory to a particular adverse context when repeatedly exposed to the context in the absence of the adverse effect.

Data is shown for mice that have undergone early-life stress, normally reared non-stressed control mice, and mice that have undergone early-life stress and treatment with the ellagitannin punicalagin. Results are expressed as mean±SEM. Significance: *p<0.05, #p=0.05 (Student's t-test). Normal non-stressed animals are compared to early-life stressed animals (i.e., maternal separation). Punicalagin treated early-life stressed animals are compared to untreated early-life stressed animals.

Figure 44:
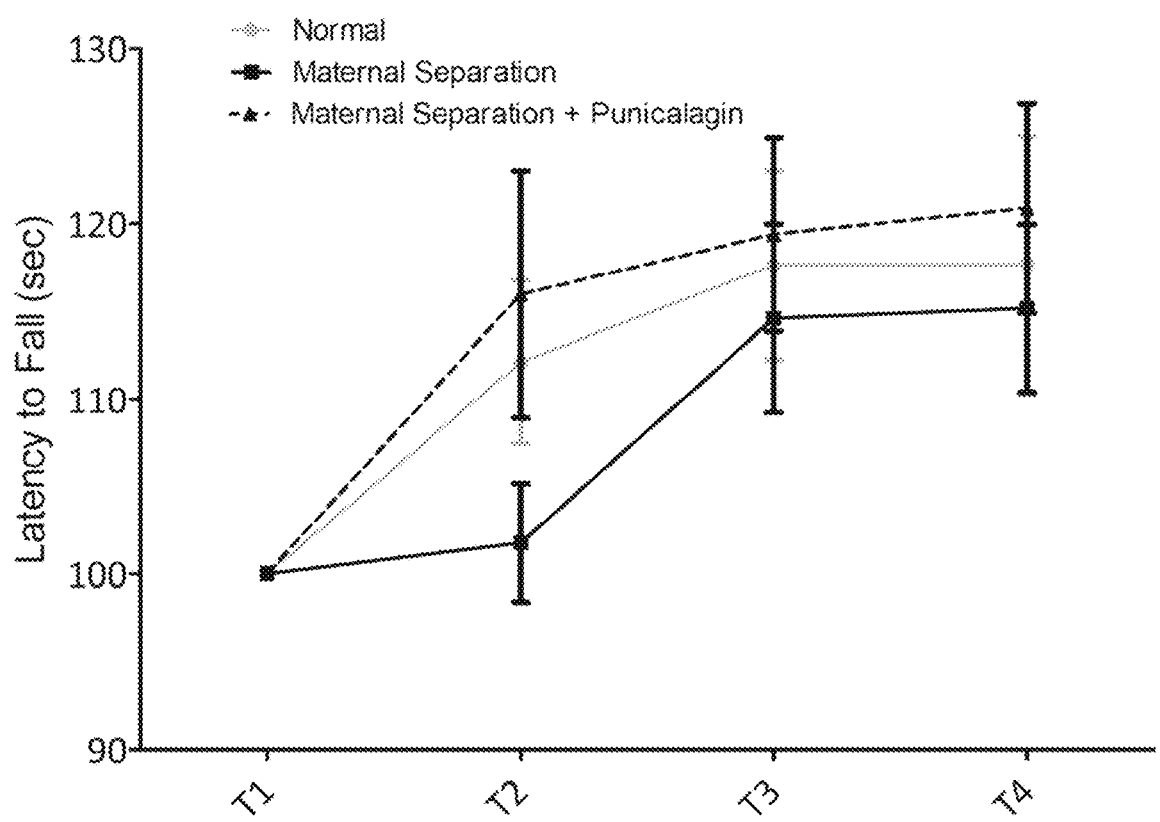

FIG. 44 is a line graph demonstrating the level of motor learning as measured by the latency in seconds to fall from a rotating rod. Data is shown for mice that have undergone early-life stress, normally reared control mice, and mice that have undergone early-life stress and have been treated with the ellagitannin punicalagin. Results are expressed as mean±SEM.

Figure 45:
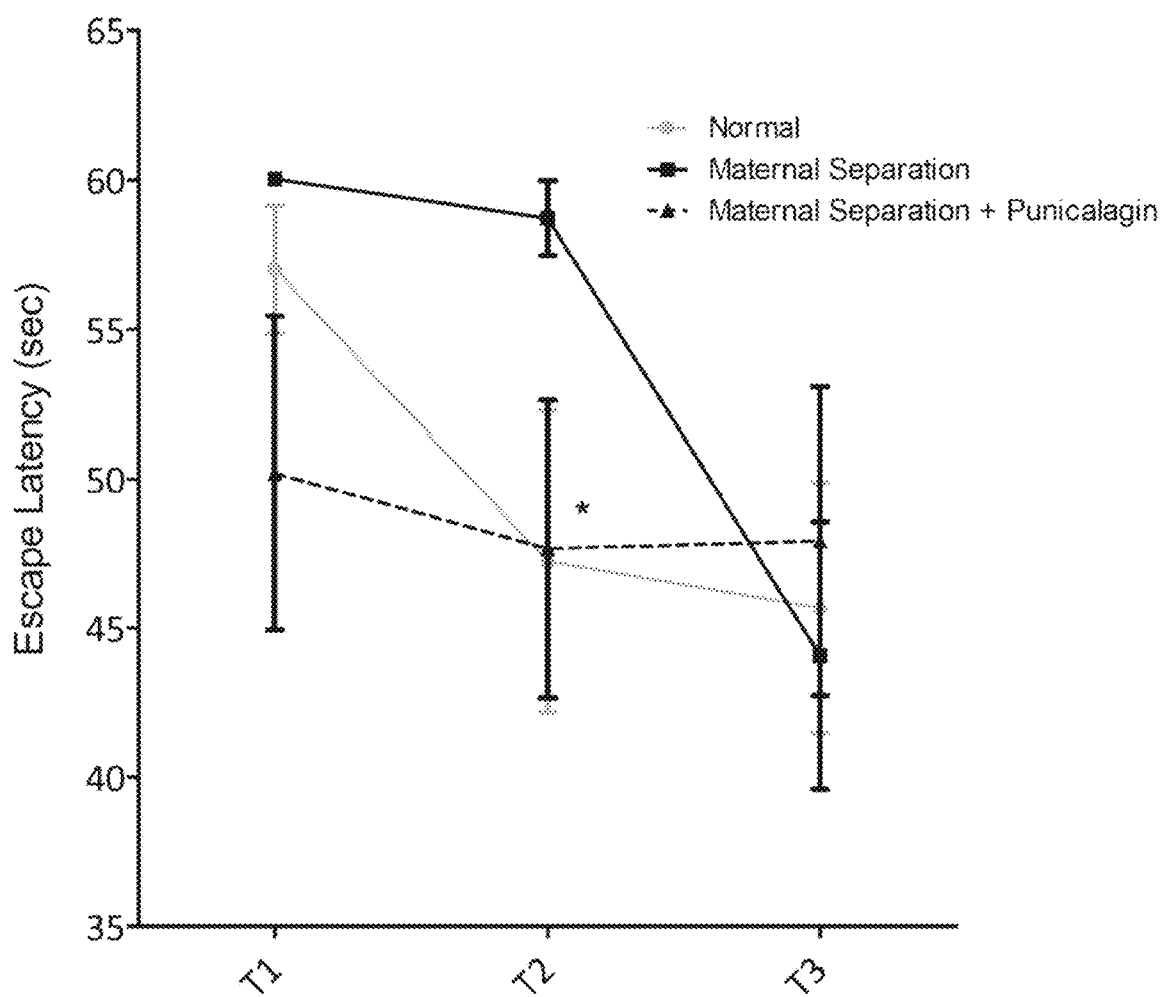

FIG. 45 is a graph depicting the escape latency in seconds from the Morris water maze during the training phase, a measurement of cognitive learning. Data is shown for mice that have undergone early-life stress, normally reared control mice, and mice that have undergone early life stress and have been treated with the ellagitannin punicalagin. Results are expressed as mean±SEM. Significance: *p<0.05 (Student's t-test).

Figure 46:
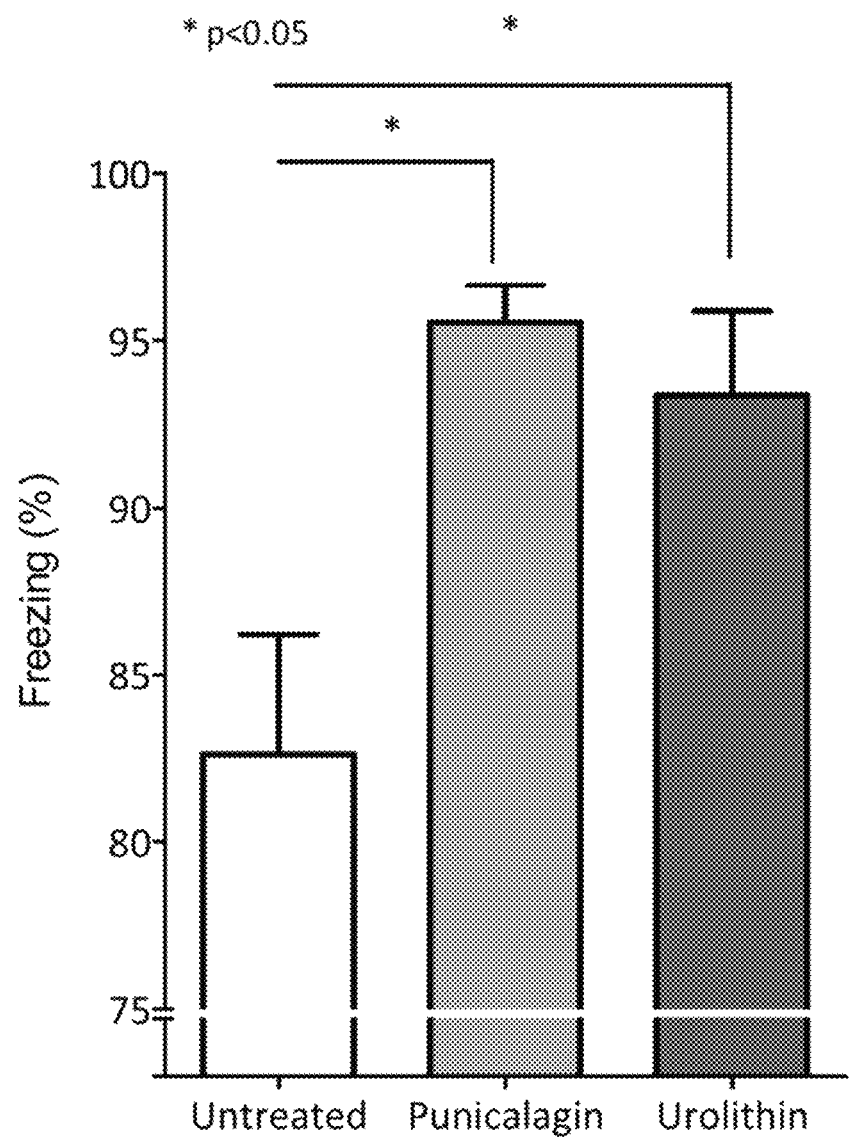

FIG. 46 is a bar graph depicting the effects of pomegranate-derived compounds on contextual recognition in normal mice, either untreated or treated with punicalagin or urolithin A. Results are expressed as mean±SEM. Significance: *p<0.05 (Student's t-test).

Figure 47:
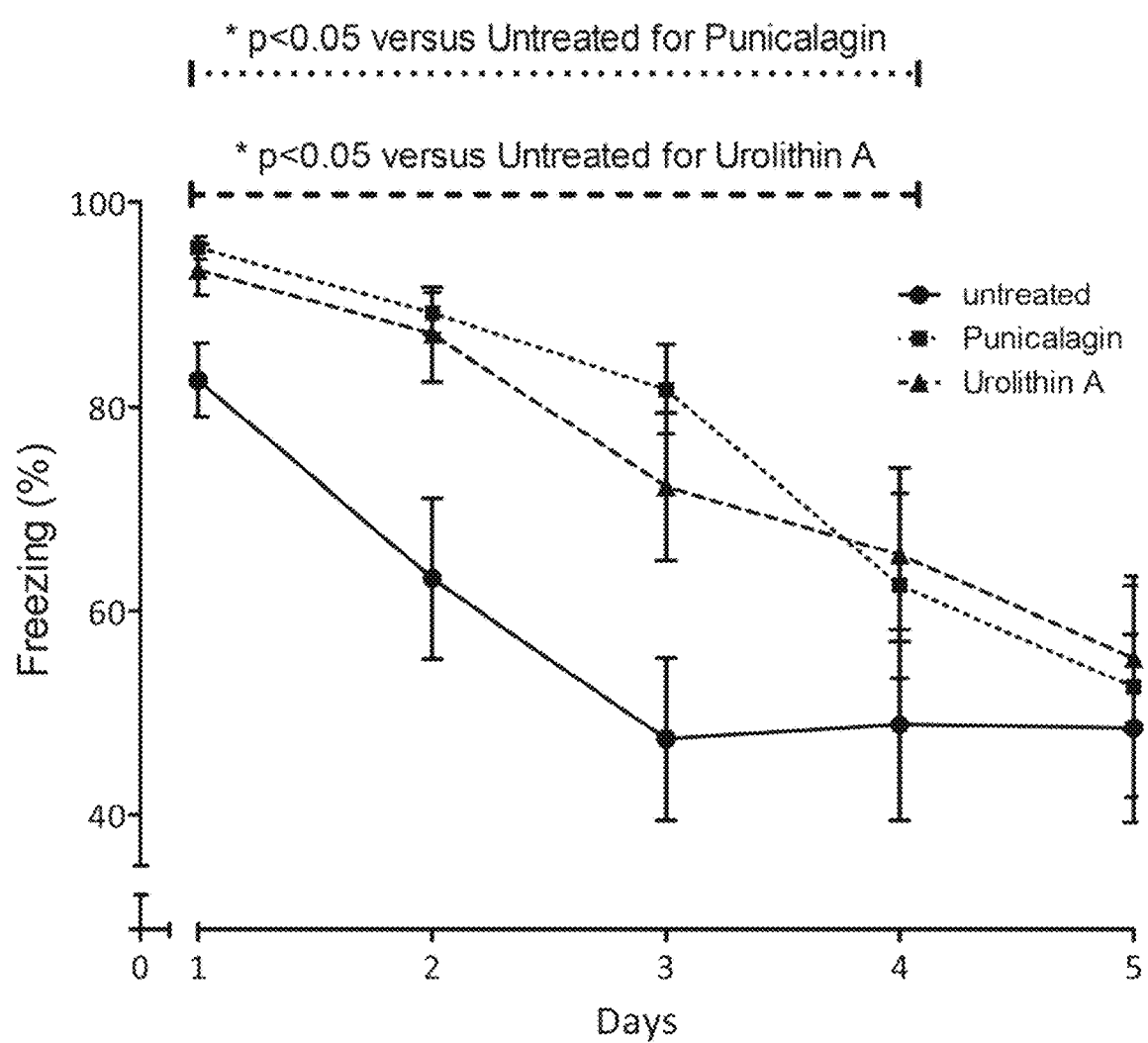

FIG. 47 is a bar graph depicting the effects of pomegranate-derived compounds on retention of memory for a particular context in normal mice, either untreated or treated with punicalagin or urolithin A. Results are expressed as mean±SEM. Significance: Data were analyzed using either one-way ANOVA or repeated measure ANOVA, followed by a Fisher post-hoc LSD multiple comparison test. *p<0.05.

Figure 48:
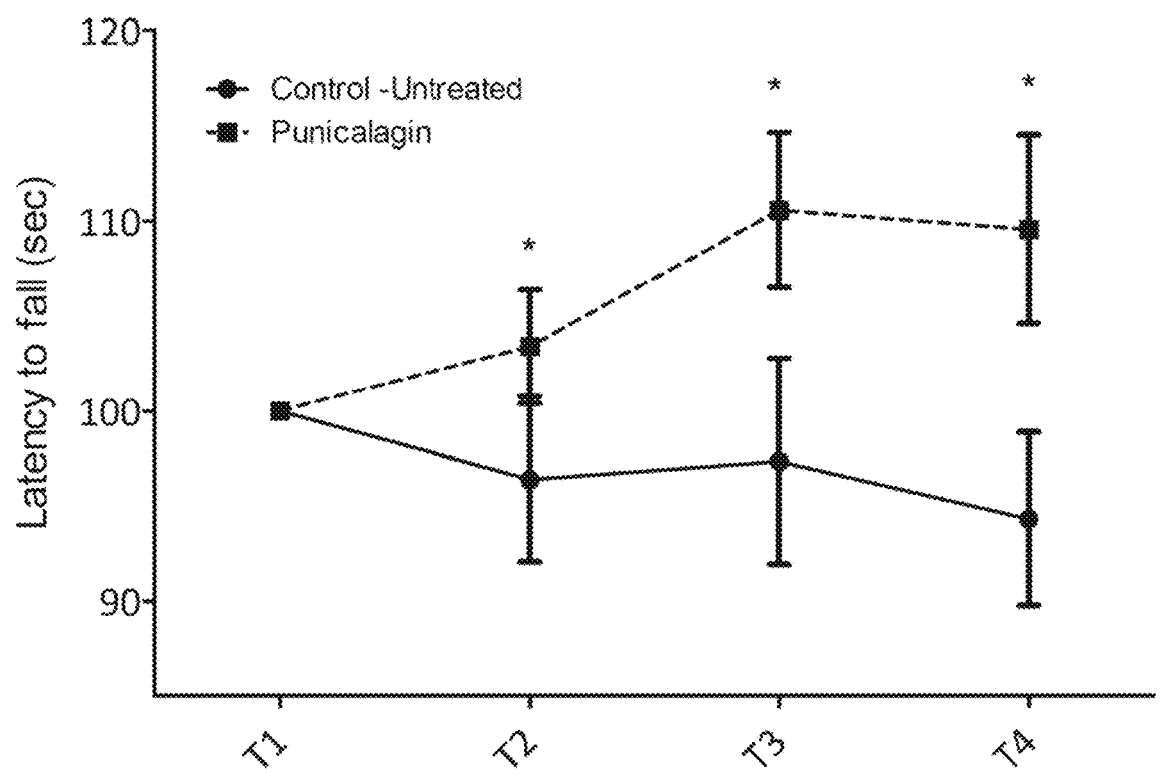

FIG. 48 is a line graph demonstrating muscle performance and motor skills as measured by the latency to fall in seconds from a turning rotarod. Data is shown for normally reared untreated control mice and mice that have been treated with the ellagitannin punicalagin. Significance: *p<0.05 by ANOVA analysis.

Figure 49:
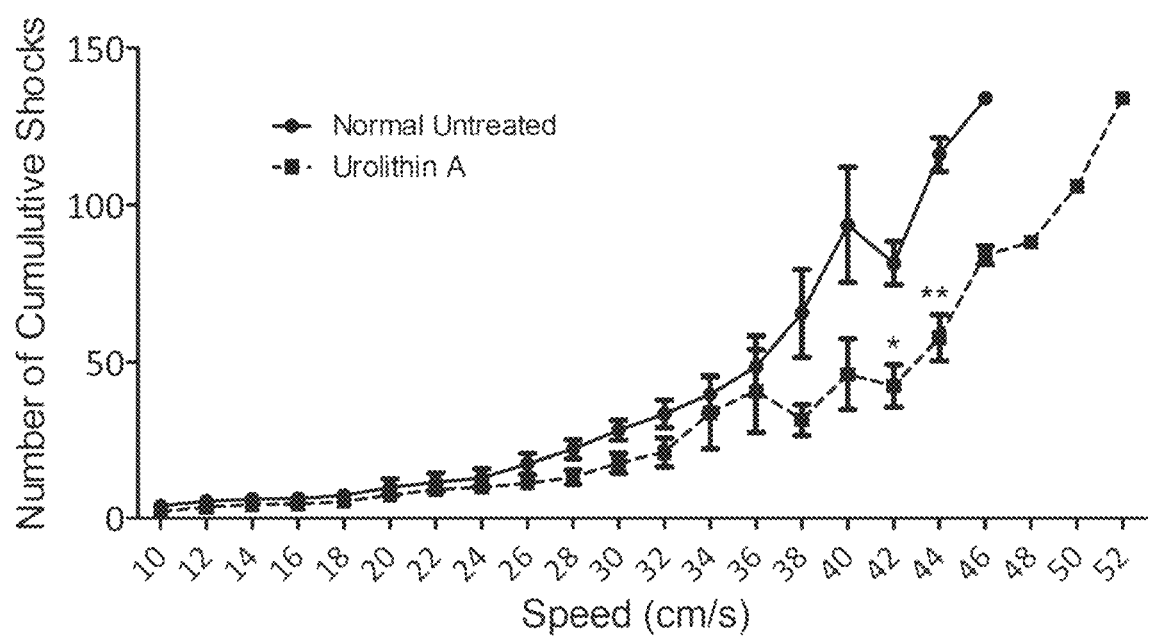

FIG. 49 is a line graph demonstrating the level of muscle performance and endurance as measured by ability of a mouse to run on a treadmill at elevated speeds. Data is shown for normally reared untreated control mice and mice that have been treated with urolithin A. Significance: *p<0.05, **p<0.01 (Student's t-test).

DETAILED DESCRIPTION OF THE INVENTION

In biology and psychology, the term "stress" refers to the consequence of the failure of a human or other animal to respond appropriately to physiological, emotional, or physical threats, whether actual or imagined. The term "stress" was first employed in a biological context by the endocrinologist Hans Selye in the 1930s. He later broadened and popularized the concept to include inappropriate physiological response to any demand. It covers a wide range of phenomena, from mild irritation to drastic dysfunction that may cause severe health breakdown.

All of these psychobiological features of stress may represent manifestations of oxidative stress, an imbalance between the production and manifestation of reactive oxygen species and the ability of a biological system readily to detoxify the reactive intermediates or to repair the resulting damage. Disturbances in the normal redox state of tissues can cause toxic effects through the production of peroxides and free radicals that damage all of the components of the cell, including proteins, lipids, and DNA. Some reactive oxidative species can even act as messengers through a phenomenon called "redox signaling."

In humans, oxidative stress is involved in many diseases. Examples include atherosclerosis, Parkinson's disease, heart failure, myocardial infarction, Alzheimer's disease, schizophrenia, bipolar disorder, fragile X syndrome, and chronic fatigue syndrome. One source of reactive oxygen under normal conditions in humans is the leakage of activated oxygen from mitochondria during oxidative phosphorylation.

Other enzymes capable of producing superoxide ($O_2$) are xanthine oxidase, NADPH oxidases and cytochromes P450. Hydrogen peroxide, another strong oxidizing agent, is produced by a wide variety of enzymes including several oxidases. Reactive oxygen species play important roles in cell signaling, a process termed redox signaling. Thus, to maintain proper cellular homeostasis a balance must be struck between reactive oxygen production and consumption.

The best studied cellular antioxidants are the enzymes superoxide dismutase (SOD), catalase, and glutathione peroxidase. Less-well-studied enzymatic antioxidants include the peroxiredoxins and the recently discovered sulfiredoxin. Other enzymes that have antioxidant properties (although this role is not primary) include paraoxonase, glutathione-S transferases, and aldehyde dehydrogenases.

Oxidative stress contributes to tissue injury following irradiation and hyperoxia. It is suspected to be important in neurodegenerative diseases, including Alzheimer's disease, Parkinson's disease, amyotrophic lateral sclerosis (ALS), and Huntington's disease. Oxidative stress is also thought to be linked to certain cardiovascular diseases, since oxidation of low-density lipoprotein (LDL) in the vascular endothelium is a precursor to plaque formation. Oxidative stress also plays a role in the ischemic cascade due to oxygen reperfusion injury following hypoxia. This cascade includes both strokes and heart attacks. Oxidative stress has also been implicated in chronic fatigue syndrome.

Remarkably, the inventors have discovered that certain compounds derived from ellagitannins are useful in the treatment and prevention of physiological and psychological manifestations of stress, including oxidative stress. Without meaning to be tied to any particular mechanism of action, it is believed that the compounds exert beneficial effects on mitochondria, promoting and restoring crucial mitochondrial functions and counteracting stress-induced mitochondrial dysfunction. These same compounds have been discovered, in accordance with the instant invention, to be useful in the treatment and prevention of any of a variety of conditions, diseases, and disorders related to mitochondrial dysfunction including, without limitation, neurodegenerative diseases and cognitive disorders, metabolic disorders including insulin resistance, mood disorders, and anxiety disorders.

Ellagitannins (ETs) are polyphenols included within the so called "hydrolyzable tannins" in which hexahydroxydiphenic acid forms diesters with sugars (most often (3-D-glucose). ETs can occur as complex polymers reaching molecular weights up to 4000 and higher. These polymers can be hydrolyzed with acids or bases to yield ellagic acid (EA), which can be used indirectly to quantify ETs. EA in turn is a source of additional metabolic products including urolithins.

Many plant species containing ellagitannins have been used for the treatment of diseases, particularly in Asia (Okuda et al., 2009). These include *Agrimonia pilosa* (agrimoniin), *Camelia japonica* (camelliatannin A), *Cornus officinalis* (cornussin A), *Geranium thunbergii* (geraniin), *Geum japonicum* (gemin-A), *Liquidambar formosana* (casuarictin), *Mallotus japonicus* (mallotusinic acid), *Oenothera erythrosepala* (oenothein B), *Punica granatum* (pomegranate) (granatin B), *Rosa rugosa* (rugosin), and *Terminalia chebula* (chebulinic acid), among others. The main uses of these medicinal plants have been associated to their antioxidant, anti-diarrheic, anti-microbial, and immunomodulatory activities.

Ellagitannins are also present in significant amounts in many berries, including strawberries, red and black raspberries (Zafrilla et al., 2001), blueberries, and blackberries. Ellagitannins have also been found in apples, cherries, cloudberries, cranberries, currants, grapes, lime, mango, pineapple, pomegranate, prune, rhubarbs. Serrano et al. (2009) *Mol Nutr Food Res*. 53:S310-29. The ellagitannin rubusuaviin C can be isolated from the leaves of the Chinese sweet tea *Rubus suavissimus* S. Lee. Ellagitannins have also been identified in appreciable amounts in nuts, including walnuts (Fukuda et al., 2003), pistachios, cashew nuts, chestnuts, oak acorns (Cantos et al., 2003) pecans (Villar-real-Lozoya et al., 2007) and peanuts.

They are also abundant in pomegranates (Gil et al., 2000), and muscadine grapes (Lee and Talcott, 2002) and are important constituents of wood, particularly oak (Glabasnia and Hofmann, 2006). Ellagitannins can be incorporated into food products, such as wines, and whiskey, through migration from wood to the food matrix during different aging processes. Ellagic acid has also been found in several types of honey and it has been proposed as a floral marker for heather honey (Ferreres et al., 1996). Free ellagic acid and different glycosidic derivatives are also present in these food products, including glucosides, rhamnosides, arabinosides and the corresponding acetyl esters (Zafrilla et al., 2001).

A number of studies have shown that the ellagitannin content of several food products can be quite high (Table 1). For example, a glass of pomegranate juice (200 mL) can provide as much as 1 g of ellagitannins and ellagic acid together, a raspberry serving (100 g raspberries) around 300 mg, a strawberry serving 70 mg, and four walnuts some 400 mg of ellagitannins.

Representative dietary ellagitannins include punicalagin of pomegranate, sanguiin-H-6 of strawberry and raspberry, and pedunculagin of walnuts. All of these release ellagic acid upon hydrolysis, although other metabolites can also be produced and are distinctive of individual ellagitannins (e.g., gallagic and ter-gallagic acids).

TABLE 1

Ellagitannins (ETs) and ellagic acid (EA) content in various food products.

| Food | Content |
|---|---|
| Fresh fruits | |
| Raspberry | 263-330 mg/100 g f.w |
| Raspberry | 51-330 mg/100 g f.w. |
| Strawberry | 77-85 mg/100 g f.w. |
| Strawberry | 25 mg/100 g f.w. |
| Cloudberry | 315 mg/100 g f.w. |
| Cloudberry | 56-360 mg/100 g f.w. |
| Blackberry | 1.5-2.0 mg/g d.w. |
| Arctic bramble | 69-320 mg/100 g f.w. |
| Pomegranates | 35-75 mg/100 g f.w. (arils) |
| Muscadine grapes | 36-91 mg/100 g f.w. |
| Nuts | |
| Walnut | 802 mg/50 g (8 nuts) |
| Pecan | 20.96-86.2 mg/g (EA) |
| Chestnut | 1.61-24.9 mg/kg d.w. (EA) |
| Processed fruits | |
| Pomegranate juice | 1500-1900 mg/L (punicalagin) |
| Pomegranate juice | 2020-2660 mg/L (ETs and EA) |
| Pomegranate juice | 5700 mg/L (ETs and EA) |
| Raspberry jam | 76 mg/100 g f.w. |
| Strawberry jam | 24 mg/100 g f.w. |
| Muscadine grape juice | 8-84 mg/L |
| Wines | |
| Oak-aged red wine | 9.4 mg/L |
| Oak-aged red wine | 50 mg/L |
| Muscadine grape wine | 2-65 mg/L |
| Spirits | |
| Whiskey | 1-2 mg/L |
| Cognac | 31-55 mg/L | f.w., fresh weight
d.w., dry weight

Ellagitannins have an enormous structural variability, forming dimeric and oligomeric derivatives. They also have a more widespread distribution than gallotanins. Additional ellagitannins and reported sources for same are shown in Table 2.

TABLE 2

Other Ellagitannins.

| | Molecular Weight | Source | Reference |
|---|---|---|---|
| 2-O-galloyl-punicalin | | European Oak Heartwood | (Puech, Mertz et al. 1999) |
| Casauricitin | | Rhu tree, Stachyrus plant | Wikipedia |
| Castalagin & Vecalagin | 934.63 | Pomegranate bark | (Tanaka, Nonaka et al. 1986) |
| Castalin | | | |
| Casuarictin | | *T. japonica* | |
| Casuariin | | Banaba tree leaves | (Bai, He et al. 2008) |
| Casuarinin | | Banaba tree leaves | (Bai, He et al. 2008) |
| Casuarinin | | Pomegranate | |
| Chebulagic acid | | *T. chebula* | |
| Chebulinic acid | | *T. chebula* | |
| Corilagin | | Pomegranate | |
| Cornusiin E | | | |
| Epipunicacortein A | | Banaba tree leaves | (Bai, He et al. 2008) |
| Flosin B | | Banaba tree leaves | (Bai, He et al. 2008) |
| Gemin D | | *T. japonica* | |
| Granatin A | | Pomegranate | |
| Granatin B | | Pomegranate | |
| Grandinin | | | |
| Lagerstroemin | | Banaba tree leaves | (Bai, He et al. 2008) |

TABLE 2-continued

Other Ellagitannins.

| | Molecular Weight | Source | Reference |
|---|---|---|---|
| Lambertianin C | | Raspberries | (Gasperotti, Masuero et al.) |
| Pedunculagin | 784.52 | Pomegrante bark, and pericarp | (Tanaka, Nonaka et al. 1986) |
| Punicacortein A | | Pomegranate | |
| Punicacortein B | | Pomegranate | |
| Punicacortein C | | Pomegranate | |
| Punicacortein D | | Pomegranate | |
| Punicafolin | | Pomegranate | |
| Punicalagin | | Pomegranate | |
| Punicalin | | Pomegranate | |
| Punigluconin | | Pomegranate | |
| Roburin A | | | |
| Roburin B | | | |
| Roburin C | | | |
| Roburin D | | | |
| Roburin E | | | |
| Rubusuaviin C | | Tea leaves | |
| Sanguiin H-4 | | Muscadine grapes | (Lee, Johnson et al. 2005) |
| Sanguiin H-5 | | Muscadine grapes | (Lee, Johnson et al. 2005) |
| Sanguiin H-6 | | Raspberries, Sanguisorba | (Vrhovsek, Palchetti et al. 2006) |
| Sanguiin H-10 | | | |
| Stachyurin | | Banaba tree leaves | (Bai, He et al. 2008) |
| Strictinin | | | |
| Tellimagrandin I | | Pomegranate | |
| Tellimigrandin II | | Pomegranate | |
| Terchebulin | | | |
| Terflavin A | | | |
| Terflavin B | | | |
| Tergallagin | | *T. catappa* | |
| Terminalin/ Gallagyldilacton | | Pomegranate | |

Many potentially active ellagitannins can be isolated from various species of *Terminalia* plants. In particular, both punicalagin and punicalin have been identified in several *Terminalia* species, including, e.g., *T. catappa*, *T. chebula* Retz, *T. myriocarpa*, and *T. citrine*. Punicalagin has also been isolated from *Cistus salvifolius* (a Mediterranean shrub) and *Combretum molle* (an African shrub).

Ellagic acid is normally found in relatively low amounts in plant tissues. Ellagic acid is thought to be derived from ellagitannins, which when broken down form Hexahydroxy-diphenic acid, which spontaneously convert to ellagic acid. Some additional sources of ellagic acid are shown in Table 3.

TABLE 3

Sources with Ellagic Acid.

| Fruit | Quantity | Reference |
|---|---|---|
| Acai | 55.4 ± 1.39 mg/L fresh pulp | (Del Pozo-Insfran, Brenes et al. 2004) |
| Umbu | 314 mg/100 g dry weight (commercial) | (De Souza Schmidt Goncalves, Lajolo et al.) |
| Camu-camu | 490 mg/100 g dry weight | (De Souza Schmidt Goncalves, Lajolo et al.) |
| Cagaita | 289 mg/100 g dry weight (commercial) | (De Souza Schmidt Goncalves, Lajolo et al.) |
| Araçá | 262 mg/100 g dry weight 218 mg/100 g dry weight (commercial) | (De Souza Schmidt Goncalves, Lajolo et al.) |

TABLE 3-continued

Sources with Ellagic Acid.

| Fruit | Quantity | Reference |
|---|---|---|
| Cambuci | 240 mg/100 g dry weight 512 mg/100 g dry weight (commercial) | (De Souza Schmidt Goncalves, Lajolo et al.) |
| Muscadine Grapes | 219 mg/100 g dry weight | (Lee, Johnson et al. 2005) |

Pomegranate (*Punica granatum*) fruits are ancient medicinal foods which have been used for centuries in folk medicine. They are consumed fresh and as juice, which is an excellent source of ellagitannins and ellagic acid. Ellagitannins in pomegranate fruit husk and juice include punicalin, punicalagin, corilagin, casuarinin, terminalin/gallagyldilacton, pedunculagin, tellimagrandin, granatin A, and granatin B. Other parts of the pomegranate plant contain additional ellagitannins, including punicafolin, punicacortein A, punicacortein B, punicacortein C, punicacortein D, and punigluconin. Commercial juices contain gallagyl-type ellagitannins, including punicalagin isomers (1500-1900 mg/L), undefined hydrolyzable tannins (400-500 mg/L), and ellagic acid and its glycosides (120-260 mg/L) (Gil et al., 2000). Punicalagins, ellagitannins in which gallagic and ellagic acids are linked to a glucose molecule, are abundant in pomegranate peel. Punicalagin isomers and ellagic acid derivatives are not present in the aril juice, but during industrial juice processing they are extracted from the husk and membrane surrounding the arils and released in large quantities into the juice.

Extracts of the invention can be prepared by first juicing a fruit, for example, the pomegranate may be juiced using standard industrial juicing methods know in the art which may include juicing the whole fruit by application of pressure to the entire fruit or by first deshelling the pomegranate and then applying pressure to the remaining material, consisting of the arils, the membranous materials which entrap the arils and the material of the husk produced during the deshelling process. Alternatively, the husk, which is a rich source of the ellagitannins, in particular punicalagin, may undergo a juicing process that includes a water extraction. Alternative, non-water extraction methods may employ other solvents such as ethanol, acetone, or methanol, as means of example.

The extract is typically an aqueous extract, which can consist essentially of the juice of the fruit, optionally with the addition of extra water. Such aqueous extracts can be concentrated, enriched or condensed by, for example, standard techniques, e.g., evaporation under reduced pressure and filtration methods. Examples of concentrates are those which are at least 2-fold concentrated, more usually at least 4-fold, for example at least 8-fold, at least 40-fold, at least 100-fold, at least 200-fold, or at least 1000-fold.

The extracts can be fractionated to isolate one or more active components therein by, for example, molecular weight filtration, or chromatography on a suitable solid support such as a sepharose gel (for size exclusion chromatography) or ion-exchange column using HPLC on a suitably treated silica or alumina, for example ODS coated silica, or by solvent extraction.

In vitro digestion simulation studies have shown that, in general, ellagitannins are quite stable under the physiological conditions of the stomach. The acidic conditions (HCl, pH 1.8-2.0) and the stomach enzymes do not hydrolyze the original ellagitannins to release free ellagic acid (EA), and no degradation of the ellagitannins has been observed (Tomas-Barberan et al., 2009). While the stomach seems to be the first important place for the absorption of free EA, ellagitannins are not absorbed. Under the physiological conditions of the small intestine, however, there is a release of free EA from ellagitannins. This hydrolysis seems to be due to the pH conditions (neutral to mild alkaline pH, 7.0-7.3) rather than to the effect of pancreatic enzymes and bile salts (Larrosa et al., 2006).

Animal studies have also been used to evaluate the bioavailability and metabolism of EA and ellagitannins. A rapid absorption and metabolism of EA was reported by Doyle and Griffiths (1980) in rats. These authors detected urolithin A (UA) and another metabolite (most probably urolithin B (UB)) in feces and urine. Both UA and UB were demonstrated to be of microfloral origin since none were found in germ-free animals. Unchanged EA was not detected in urine or feces. These urolithins are largely absorbed and glucuronidated by the intestinal cells. In this case, no methyl ethers are produced as UA and UB do not have ortho-dihydroxyl groupings in their molecules and therefore are not substrates for catechol-O-methyl transferase (COMT). In the case of UB, an additional hydroxyl can be introduced by cytochrome P450, and this increases the possibilities of glucuronidation and enhances the excretion of the metabolite. Teel and Martin (1988) found that both free EA and some conjugates (sulfate ester, glucuronide and glutathione conjugates) were detected in mice urine, bile and blood. Absorption of $^3$H-EA occurred mostly within two hours of oral administration. Levels in blood, bile and tissues were low, and absorbed compounds were excreted in urine. More than half of the administered $^3$H-EA remained in the gastrointestinal tract after 24 h.

The metabolism of various dietary ETs and EA derivatives has been assessed in humans. In a study involving forty healthy volunteers, divided into four groups, different ET-containing foodstuffs were administered, including strawberries (250 g), red raspberries (225 g), walnuts (35 g), and oak-aged red wine (300 mL). Strawberries and raspberries both contain the ET sanguiin H-6; walnuts contain the ET pedunculagin; and oak-aged wine contains the ET vescalagin. After the intake, five urine fractions were collected at 8, 16, 32, 40, and 56 h. Neither ETs nor EA were detected in urine using LC-MS/MS analysis. However, the microbial metabolite 3,8-dihydroxy-6H-dibenzo[b,d]pyran-6-one (urolithin B) conjugated with glucuronic acid was detected among the fractions starting at 32 h until 56 h in all of the subjects, independent of the consumed foodstuff. According to the results obtained, urolithin B derivatives were excreted independently of the ET consumed. A common monomeric moiety in the ETs consumed was EA (m/z—at 301), which could indicate that this subunit belonging to ET molecules was the critical molecule to produce urolithin B derivatives. A similar metabolic transformation to ellagic acid and urolithin was observed for the ellagitannins in humans consuming pomegranate juice (Cerda, Espin et al. 2004; Cerda, Periago et al. 2005).

Figure 2:
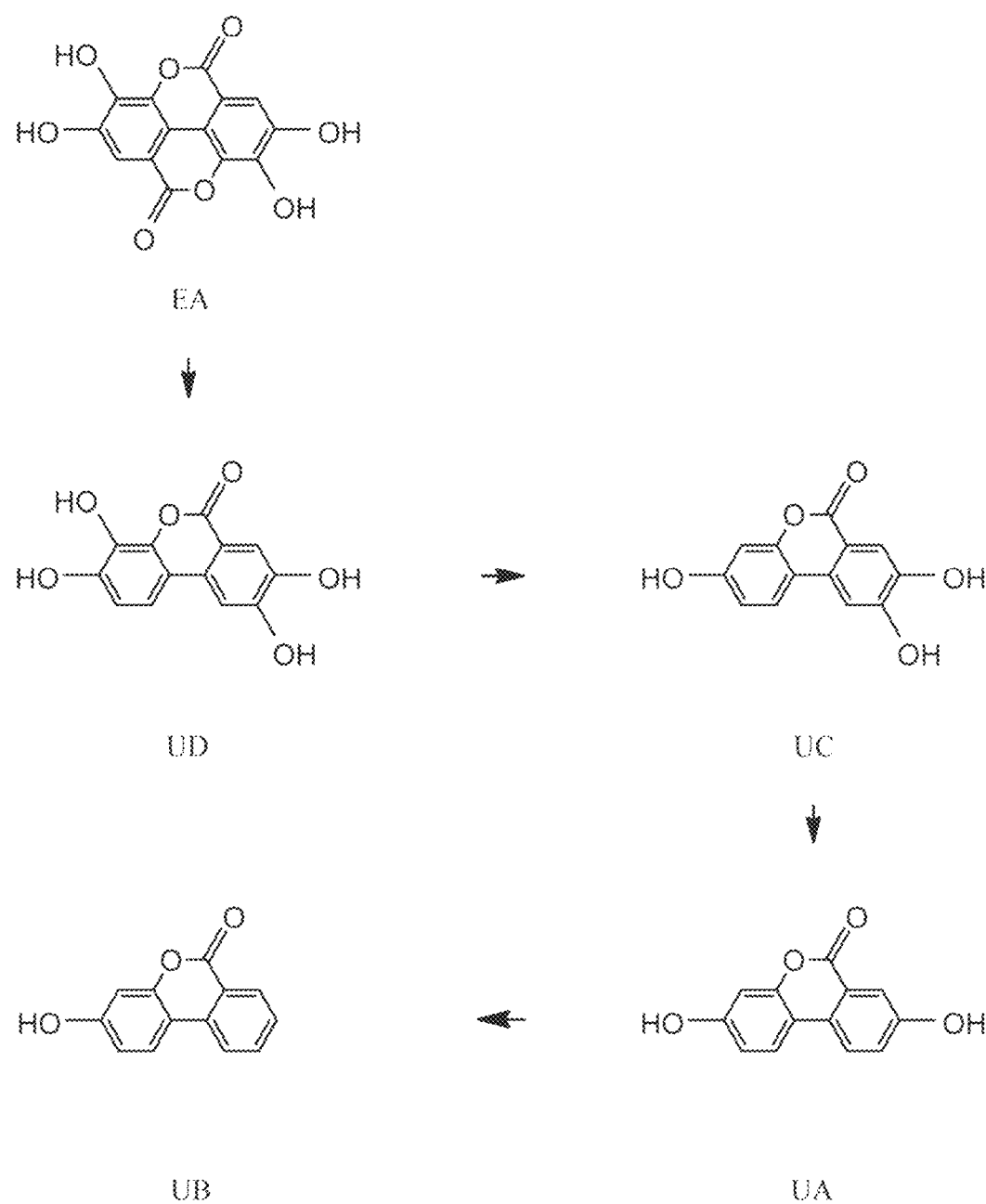
FIG. 2 depicts ellagic acid (EA) and its metabolites, urolithin D (UD), urolithin C (UC), urolithin A (UA), and urolithin B (UB), which are produced by intestinal microflora in animals, including humans.

One of the main factors in the metabolism and bioavailability of ellagitannins is their microbial transformation to render a series of urolithin derivatives (FIG. 2). Among them, the best characterized and known are urolithin A and B, but intermediates with three and four hydroxyls are also produced in the small intestine, absorbed, and excreted in the bile after conjugation with methyl ethers and glucuronides (Espin et al., 2007). Animal experiments show that these metabolites start to be formed in the small intestine, indicating that anaerobic bacteria may be responsible for this. The metabolism continues along the GI tract starting with urolithins D and C to end with the production of urolithins A and B. Differences in the production of these metabolites by human volunteers show that they may be produced by the activity of specific microorganisms present in the gut.

In the gastrointestinal tract and in other tissues (mainly in the liver), EA and ellagitannin microbial metabolites are further metabolized either by Phase I (hydroxylation) and Phase II (methylation, glucuronidation, and sulfation) enzymes to render more soluble metabolites that may be distributed among tissues and then excreted in urine.

Thus, UB can be hydroxylated to produce UA and this can be further hydroxylated to produce tri-hydroxy-derivatives.

Phase II products are also produced and methyl ethers (products of COMT) as well as different glucuronide conjugates are detected in different tissues and in urine. Sulphate conjugates of ellagitannin metabolites are less abundant in animals and humans than the glucuronide conjugates. These conjugates are first produced in the intestinal cells, and further metabolized in the liver before excretion in the urine or the bile.

To summarize, ellagitannins are generally not absorbed in the gut. Rather, they release EA in the gut, which is only poorly absorbed in the stomach and small intestine. EA is largely metabolized by unidentified bacteria in the intestinal lumen to produce urolithins. Microbial metabolism starts in the small intestine and the first metabolites produced retain four phenolic hydroxyls (urolithin D, four hydroxyl groups), and these are further metabolized along the intestinal tract to remove hydroxyl units leading to urolithin C (three hydroxyls), urolithin A (two hydroxyls) and B (one hydroxyl) in the distal parts of the colon (FIG. 2). The absorbed metabolites are conjugated with glucuronic acid (one or two units), and/or methyl ethers (when ortho-dihydroxyl groupings are present). Urolithin A and B conjugates are the main metabolites detected in plasma and urine, although some trihydroxy derivatives (hydroxyl-UA) or EA-dimethyl ether glucuronide have also been detected in smaller amounts. The tetrahydroxy-urolithins, trihydroxy-urolithins, and EA derivatives generally are not detected in peripheral plasma, but they are absorbed in the small intestine and they are transported to the liver where they are further metabolized and excreted with bile to the small intestine establishing an enterohepatic circulation that is responsible for the relatively long life of urolithins in plasma and urine.

In addition to natural food sources, many papers have appeared on the biosynthesis, isolation, and biological activity of tannins, especially ellagitannins, over the last twenty years (e.g., Xie et al., 1995, Yoshida et al., 1982, 1984, 1985, 1986, 1989, 1990a/b, 1991a-d, 1992a/b, 1995, Nonaka et al., 1980, 1984, 1989a-c, 1990, Tanaka et al., 1986a/b, 1990, 1992a/b, 2001, Hatano et al., 1988, 1989, 1990a-c, 1991, 1995, Lin et al., 1990, Nishizawa et al., 1982, 1983, Haddock et al., 1982a/b, Kashiwada et al., 1992a/b, 1993, Kadota et al., 1990, Okuda et al., 1982a-e, 1983a/b, El-Mekkawy et al., Chemistry and Biology of Ellagitannins 154 1995, Tsai et al., 1992, Han et al., 1995, Chen et al., 1995, Morimoto et al., 1986a/b, Saijo et al., 1989). Access to pure ellagitannins by isolation from natural sources may be cumbersome and yield only relatively small quantities of pure natural products. See, for example, Okuda et al., (1982) *Chem Pharm Bull.* 30:4230-4233; Okuda et al. (1982) *Chem Pharm Bull.* 30:234-4236. It is therefore notable that methods for total synthesis of many ellagitannins are known. See, for example, Khanbabaee, K., Strategies for the synthesis of ellagitannins, In: Chemistry and Biology of Ellagitannins, Ed. S. Quideau, World Scientific Publishing, Singapore, 2009, pp. 152-202, including references cited therein.

Antioxidant activities of food extracts rich in ellagitannins have been determined by using various in vitro assays, and the high activities of strawberries (Meyers et al., 2003, Aaby et al., 2005, 2007), raspberries (Liu et al., 2002, Beekwilder et al., 2005), cloudberries (Kähkönen et al., 2001) and other *Rubus* berries (Wada and Ou, 2002), pomegranates (Gil et al., 2000) and walnuts (Anderson et al., 2001) and their ellagitannins have been extensively reported. These foods also rank high when compared to other plant-based foods.

Less is known about the effects of consumption of ellagitannin-rich foods on the antioxidant status in vivo. In elderly women, the total antioxidant capacity of serum increased by about 10% during the 4-hour period after consumption of 240 g of strawberries (Cao et al., 1998). A single dose of standardized pomegranate extract (Mertens-Talcott et al., 2006) and long-term consumption of pomegranate juice (Rosenblat et al., 2006) also improved several antioxidant parameters in human volunteers. However, the daily consumption of walnuts for three weeks had no effect on the antioxidant status of subjects with metabolic syndrome (Davis et al., 2007).

Cancer cell growth is dependent on the balance between proliferation and apoptosis. Unregulated cell proliferation and suppression of apoptosis are key steps in initiation and progression of cancer. There is a substantial amount of evidence that extracts of ellagitannin-rich foods reduce the growth of cancer cells in vitro by inhibiting cell proliferation, inducing apoptotic cell death, and modulating cell cycle kinetics and signal transduction pathways.

In vitro studies carried out with cancer cell lines have shown that strawberries (Meyers et al., 2003, Olsson et al., 2004, Ramos et al., 2005, Wang et al., 2005, Wu et al., 2007), raspberries (Liu et al., 2002, Olsson et al., 2004, Wu et al., 2007), cloudberries (Wu et al., 2007) and rose hips (Olsson et al., 2004) inhibit cell proliferation, induce apoptosis and cause cell cycle arrest in human colon, liver, lung, breast or cervical cancer cells. In these studies, the contribution of ellagitannins on the activities of berry extracts was not assessed. However, a recent study (Ross et al., 2007) suggests that the anti-proliferative activity of raspberries is predominantly associated with ellagitannins.

Pomegranate juice and its ellagitannins also have been reported to inhibit proliferation, induce apoptosis, and suppress inflammatory cell signaling in colon cancer cell lines (Seeram et al., 2005, Adams et al., 2006, Larrosa et al., 2006). Likewise, polyphenols in muscadine grape skin inhibit the growth of colon cancer cells and induce apoptosis (Yi et al., 2005). Fractions isolated from red muscadine grapes and rich in ellagic acid, ellagic acid glycosides, and ellagitannins induce apoptosis, decrease cell number, and cause alterations in cell cycle kinetics in colon carcinoma cells (Mertens-Talcott et al., 2006).

Pomegranate fruit juice is effective against prostate cancer cells in vitro, but not against normal prostate epithelial cells. Treatment of highly aggressive human prostate cancer cells with pomegranate fruit extract resulted in inhibition of cell growth and viability and induction of apoptosis (Malik et al., 2005, Malik and Mukhtar, 2006).

In accordance with the instant invention, it has now been discovered that ellagitannins and their metabolites, including ellagic acid and, especially, urolithins, unexpectedly exhibit protective and restorative effects on mitochondria. Without meaning to be limited to any particular mechanism, it is believed that various types of stress result in stress injury to mitochondria, thereby reducing their ability to perform numerous functions essential to overall cell function. The methods of the invention are useful for treating conditions involving stress injury to mitochondria, which injury may be manifest in any of a number of ways including, but not limited to, mitochondrial disease.

Mitochondria are the "power centers" of cells. These double-membrane organelles play a critical role in generating the vast majority of cellular energy (ATP) via oxidative phosphorylation. Mitochondria are also essential for other key metabolic functions, such as fatty acid β-oxidation, catabolism of amino acids, ketogenesis, and generation of reactive oxygen species (ROS) with important signaling functions and control of calcium homeostasis.

The mitochondrial matrix contains the enzymatic machinery for fatty acid β-oxidation, which generates acetyl-CoA from acyl chains, and reducing equivalents in the form of reduced nicotinamide adenine dinucleotide (NADH) and reduced flavin adenine dinucleotide (FADH2) in the process. Acetyl-CoA fuels the tricarboxylic acid (TCA) cycle, also known as the citric acid cycle or Krebs cycle, which also produces NADH and FADH2. These products donate electrons to the electron transport chain (ETC), leading to the generation of a proton gradient across the inner mitochondrial membrane. Dissipation of this gradient through the mitochondrial ATP synthase generates energy in the form of ATP.

The ETC is composed of 4 large multisubunit complexes (complexes I to IV), which transport electrons generated by the TCA cycle to a final acceptor, molecular oxygen ($O_2$), forming $H_2O$ at complex IV. The transport of electrons is accompanied by release of large amounts of free energy, most of which is harnessed for the translocation of protons ($H^+$) from the matrix to the intermembrane space (proton motive force); the remainder is dissipated as heat. The energy contained in the $H^+$ electrochemical gradient generated by the ETC is then coupled to ATP production as $H^+$ flow back into the matrix through mitochondrial ATP synthase. Thus, oxidative phosphorylation results from electron transport, the generation of a proton gradient, and subsequent proton flux coupled to mitochondrial ATP synthase.

ROS can also activate uncoupling proteins (UCPs) that dissipate the proton gradient without producing ATP. UCPs are considered to be natural regulators of this process, responding to and controlling ROS production by mitigating the formation of a large proton gradient. Additionally, UCPs and respiration uncoupling are implicated in numerous important physiological and pathological processes, such as adaptive thermogenesis, regulation of fatty acid oxidation, participation in inflammation, prevention of ROS formation, glucose homeostasis, body weight regulation, and aging.

Citrate synthase is the initial enzyme of the mitochondrial TCA cycle. This enzyme catalyzes the reaction between acetyl coenzyme A (Acetyl CoA) and oxaloacetic acid to form citric acid. The activity of this enzyme reflects both mitochondrial biogenesis and mitochondrial oxidative phosphorylation, since its activity increases proportionally to mitochondrial density (number of mitochondrial per cell) and the activity of mitochondrial respiration. Consequently, citrate synthase measurement allows an overall assessment of mitochondrial functional status, with higher activity indicating an increased oxidative phosphorylation and ATP synthesis and lower activity indicating the contrary.

In order to better understand the underlying molecular mechanism leading to the improvement of mitochondrial function, a profile of key mitochondrial genes (encoding mitochondrial and genomic DNA) covering oxidative phosphorylation, mitochondrial chain complexes, TCA cycle, uncoupling proteins, transcriptional factors, co-factors and ROS-scavenging proteins may be performed.

The conventional teaching in biology and medicine is that mitochondria function only as "energy factories" for the cell. However, more than 95% (2900 of 3000) of genes encoding mitochondrial proteins are involved with other functions tied to the specialized duties of the differentiated cells in which they reside. These duties evolve during development from embryo to adult, and as tissues grow, mature, and adapt to the postnatal environment. These other, non-ATP-related functions are intimately involved with most of the major metabolic pathways used by a cell to build, break down, and recycle its molecular building blocks. Cells cannot even make the RNA and DNA they need to grow and function with out mitochondria. The building blocks of RNA and DNA are purines and pyrimidines. Mitochondria contain the rate-limiting enzymes for pyrimidine biosynthesis (dihydroorotate dehydrogenase) and heme synthesis (d-amino levulinic acid synthetase) required to make hemoglobin. In the liver, mitochondria are specialized to detoxify ammonia in the urea cycle. Mitochondria are also required for cholesterol metabolism, for estrogen and testosterone synthesis, for neurotransmitter metabolism, and for free radical production and detoxification. Mitochondria do all this in addition to oxidizing the fat, protein, and carbohydrates ingested in the diet.

Mitochondrial diseases are the result of either inherited or spontaneous mutations in mitochondrial DNA or nuclear DNA which lead to altered functions of the proteins or RNA molecules that normally reside in mitochondria. Problems with mitochondrial function, however, may only affect certain tissues as a result of factors occurring during development and growth that are not yet fully understood. Even when tissue-specific isoforms of mitochondrial proteins are considered, it is difficult to explain the variable patterns of affected organ systems in the mitochondrial disease syndromes seen clinically.

Mitochondrial diseases result from failures of the mitochondria, specialized compartments present in every cell of the body except red blood cells. Mitochondria are responsible for creating more than 90% of the energy needed by the body to sustain life and support growth. When they fail, less and less energy is generated within the cell. Cell injury and even cell death follow. If this process is repeated throughout the body, whole systems begin to fail, and the life of the person in whom this is happening is severely compromised. Mitochondrial diseases primarily affect children, but adult onset is becoming more recognized.

Diseases of the mitochondria appear to cause the most damage to cells of the brain, heart, liver, skeletal muscles, kidney, and the endocrine and respiratory systems.

Many symptoms in mitochondrial disorders are non-specific. The symptoms may also show an episodic course, with periodic exacerbations. The episodic condition of migraine, as well as myalgia, gastrointestinal symptoms, tinnitus, depression, chronic fatigue, and diabetes, have been mentioned among the various manifestations of mitochondrial disorders in review papers on mitochondrial medicine (Chinnery and Turnbull (1997) *QJM* 90:657-67; Finsterer (2004) *Eur J Neurol.* 11:163-86). In patients with mitochondrial disorders, clinical symptomatology typically occurs at times of higher energy demand associated with physiological stressors, such as illness, fasting, over-exercise, and environmental temperature extremes. Furthermore, psychological stressors also frequently trigger symptomatology, presumably due to higher brain energy demands for which the patient is unable to match with sufficient ATP production.

Depending on which cells are affected, symptoms may include loss of motor control, muscle weakness and pain, gastro-intestinal disorders and swallowing difficulties, poor growth, cardiac disease, liver disease, diabetes, respiratory complications, seizures, visual/hearing problems, lactic acidosis, developmental delays and susceptibility to infection.

Mitochondrial diseases include, without limitation, Alper's disease; Barth syndrome; beta-oxidation defects; carnitine deficiency; carnitine-acyl-carnitine deficiency; chronic progressive external ophthalmoplegia syndrome; co-enzyme Q10 deficiency; Complex I deficiency; Complex II deficiency; Complex III deficiency; Complex IV deficiency; Complex V deficiency; CPT I deficiency; CPT II deficiency; creatine deficiency syndrome; cytochrome c oxidase deficiency; glutaric aciduria type II; Kearns-Sayre syndrome; lactic acidosis; LCHAD (long-chain acyl-CoA dehydrogenase deficiency); Leber's hereditary optic neuropathy; Leigh disease; lethal infantile cardiomyopathy; Luft disease; MAD (medium-chain acyl-CoA dehydrogenase deficiency); mitochondrial cytopathy; mitochondrial DNA depletion; mitochondrial encephalomyopathy, lactic acidosis, and stroke-like symptoms; mitochondrial encephalopathy; mitochondrial myopathy; mitochondrial recessive ataxia syndrome; muscular dystrophies, myoclonic epilepsy and ragged-red fiber disease; myoneurogenic gastrointestinal encephalopathy; neuropathy, ataxia, retinitis pigmentosa, and ptosis; Pearson syndrome; POLG mutations; pyruvate carboxylase deficiency; pyruvate dehydrogenase deficiency; SCHAD (short-chain acyl-CoA dehydrogenase deficiency); and very long-chain acyl-CoA dehydrogenase deficiency.

An aspect of the invention is a food product or nutritional supplement comprising an effective amount of pomegranate extract: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

As used herein, a "food product" refers to a product prepared from a natural food. Non-limiting examples of food products include juices, wines, concentrates, jams, jellies, preserves, pastes, and extracts. As used herein, a "nutritional supplement" refers to a product suitable for consumption or other administration principally for its health-promoting properties rather than its caloric content.

As used herein, the term "metabolic syndrome" refers to a combination of medical disorders that, when occurring together, increase the risk of developing cardiovascular disease and diabetes. It affects one in five people in the United States and prevalence increases with age. Some studies have shown the prevalence in the United States to be an estimated 25% of the population. In accordance with the International Diabetes Foundation consensus worldwide definition (2006), metabolic syndrome is central obesity plus any two of the following:

Raised triglycerides: >150 mg/dL (1.7 mmol/L), or specific treatment for this lipid abnormality;

Reduced HDL cholesterol: <40 mg/dL (1.03 mmol/L) in males, <50 mg/dL (1.29 mmol/L) in females, or specific treatment for this lipid abnormality;

Raised blood pressure: systolic BP >130 or diastolic BP >85 mm Hg, or treatment of previously diagnosed hypertension; and Raised fasting plasma glucose: (FPG)>100 mg/dL (5.6 mmol/L), or previously diagnosed type 2 diabetes.

An aspect of the invention is a food product or nutritional supplement comprising an effective amount of an ellagitannin: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

In certain embodiments in accordance with this and other aspects of the invention, the ellagitannin is selected from the group consisting of 2-O-galloyl-punicalin, casaurictin, castalagin & vecalagin, castalin, casuarictin, casuariin, casuarinin, chebulagic acid, chebulinic acid, corilagin, cornusiin E, epipunicacortein A, flosin B, gemin D, granatin A, granatin B, grandinin, lagerstroemin, lambertianin C, pedunculagin, punicacortein A, punicacortein B, punicacortein C, punicacortein C, punicacortein D, punicafolin, punicalagin, punicalin, punigluconin, roburin A, roburin B, roburin C, roburin D, roburin E, rubusuaviin C, sanguiin H-4, sanguiin H-5, sanguiin H-6, sanguiin H-10, stachyurin, strictinin, tellimagrandin I, tellimigrandin II, terchebulin, terflavin A, terflavin B, Tergallagin, and terminalin/gallagyldilacton. Of course, additional ellagitannins are also contemplated by the invention.

An aspect of the invention is a food product or nutritional supplement comprising an effective amount of punicalagin: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

An aspect of the invention is a food product or nutritional supplement comprising an effective amount of ellagic acid: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

An aspect of the invention is a food product or nutritional supplement comprising an effective amount of a urolithin: for the treatment or prevention of a condition selected from the group consisting of obesity, reduced metabolic rate, metabolic syndrome, diabetes mellitus, cardiovascular disease, hyperlipidemia, neurodegenerative disease, cognitive disorder, mood disorder, stress, and anxiety disorder; for weight management; or to increase muscle performance or mental performance.

In certain embodiments in accordance with this and other aspects of the invention, the urolithin is urolithin A. In certain embodiments in accordance with this and other aspects of the invention, the urolithin is urolithin B. In certain embodiments in accordance with this and other aspects of the invention, the urolithin is urolithin C. In certain embodiments in accordance with this and other aspects of the invention, the urolithin is urolithin D.

In each of the foregoing, in one embodiment the condition is obesity.

In each of the foregoing, in one embodiment the condition is reduced metabolic rate.

In each of the foregoing, in one embodiment the condition is metabolic syndrome.

In each of the foregoing, in one embodiment the condition is diabetes mellitus.

In each of the foregoing, in one embodiment the condition is cardiovascular disease.

In each of the foregoing, in one embodiment the condition is hyperlipidemia.

In each of the foregoing, in one embodiment the condition is neurodegenerative disease.

In each of the foregoing, in one embodiment the condition is cognitive disorder.

In each of the foregoing, in one embodiment the condition is mood disorder.

In each of the foregoing, in one embodiment the condition is stress.

In each of the foregoing, in one embodiment the condition is anxiety disorder.

In each of the foregoing, in one embodiment the food product or nutritional supplement is for weight management.

In each of the foregoing, in one embodiment the food product or nutritional supplement is for increasing muscle performance.

In each of the foregoing, in one embodiment the food product or nutritional supplement is for increasing mental performance.

An aspect of the invention is a method of increasing or maintaining mitochondrial function. The method includes the step of contacting cells with an effective amount of a urolithin or a precursor thereof, to increase function of the mitochondria.

An aspect of the invention is a method of treating, preventing, or managing a mitochondria-related disease or condition associated with an altered mitochondrial function or a reduced mitochondrial density. The method includes the step of administering to a subject in need thereof a therapeutically effective amount of a urolithin or a precursor thereof, to treat the disease or condition associated with altered mitochondrial function or reduced mitochondrial density.

An aspect of the invention is a method of increasing metabolic rate. The method includes the step of administering to a subject in need thereof an effective amount of a urolithin or a precursor thereof, to increase metabolic rate. As described elsewhere herein, precursors of a urolithin can include, without limitation, an ellagitannin, punicalagin, and ellagic acid.

An aspect of the invention is a method of preventing or treating metabolic syndrome. The method includes the step of administering to a subject in need thereof an effective amount of a urolithin or a precursor thereof, to prevent or treat metabolic syndrome.

An aspect of the invention is a method of preventing or treating obesity. The method includes the step of administering to a subject in need thereof an effective amount of a urolithin or a precursor thereof, to prevent or treat obesity.

An aspect of the invention is a method of preventing or treating cardiovascular disease. The method includes the step of administering to a subject in need thereof an effective amount of a urolithin or a precursor thereof, to prevent or treat cardiovascular disease.

An aspect of the invention is a method of treating hyperlipidemia. The method includes the step of administering to a subject in need thereof an effective amount of a urolithin or a precursor thereof, to treat hyperlipidemia. In one embodiment, the hyperlipidemia is hypertriglyceridemia. In one embodiment, the hyperlipidemia is elevated free fatty acids.

An aspect of the invention is a method of treating a metabolic disorder. The method includes the step of administering to a subject in need thereof a therapeutically effective amount of a urolithin or a precursor thereof, to treat the metabolic disorder. In one embodiment, the metabolic disorder is diabetes mellitus. In one embodiment, the metabolic disorder is obesity.

Aging

By far the greatest risk factor for neurodegenerative diseases, such as Alzheimer's disease (AD), Parkinson's disease (PD), and amyotrophic lateral sclerosis (ALS), is aging. Mitochondria have been thought to contribute to aging through the accumulation of mitochondrial DNA (mtDNA) mutations and net production of reactive oxygen species (ROS). Although most mitochondrial proteins are encoded by the nuclear genome, mitochondria contain many copies of their own DNA. Human mtDNA is a circular molecule of 16,569 base pairs that encodes 13 polypeptide components of the respiratory chain, as well as the rRNAs and tRNAs necessary to support intramitochondrial protein synthesis using its own genetic code. Inherited mutations in mtDNA are known to cause a variety of diseases, most of which affect the brain and muscles—tissues with high energy requirements. It has been hypothesized that somatic mtDNA mutations acquired during aging contribute to the physiological decline that occurs with aging and aging-related neurodegeneration. It is well established that mtDNA accumulates mutations with aging, especially large-scale deletions and point mutations. In the mtDNA control region, point mutations at specific sites can accumulate to high levels in certain tissues: T414G in cultured fibroblasts, A189G and T408A in muscle, and C150T in white blood cells. However, these control-region "hot spots" have not been observed in the brain. Point mutations at individual nucleotides seem to occur at low levels in the brain, although the overall level may be high. Using a polymerase chain reaction (PCR)-cloning-sequencing strategy, it was found that the average level of point mutations in two protein-coding regions of brain mtDNA from elderly subjects was ~2 mutations per 10 kb. Noncoding regions, which may be under less selection pressure, potentially accumulate between twice and four times as many. The accumulation of these deletions and point mutations with aging correlates with decline in mitochondrial function. For example, a negative correlation has been found between brain cytochrome oxidase activity and increased point-mutation levels in a cytochrome oxidase gene (CO1).

Net production of ROS is another important mechanism by which mitochondria are thought to contribute to aging. Mitochondria contain multiple electron carriers capable of producing ROS, as well as an extensive network of antioxidant defenses. Mitochondrial insults, including oxidative damage itself, can cause an imbalance between ROS production and removal, resulting in net ROS production. The importance to aging of net mitochondrial ROS production is supported by observations that enhancing mitochondrial antioxidant defenses can increase longevity. In *Drosophila*, overexpression of the mitochondrial antioxidant enzymes manganese superoxide dismutase (MnSOD) and methionine sulfoxide reductase prolongs lifespan. This strategy is most successful in short-lived strains of *Drosophila*, and has no effect in already long-lived strains. However, it has recently been shown that overexpression of catalase experimentally targeted to mitochondria increased lifespan in an already long-lived mouse strain.

Cognitive decline during aging has been observed to occur in aging animals and is thought to occur as a result of changes in the synaptic physiology of aging neurons. These changes are thought to lead to an overall global loss of integrative function of the neuronal signaling in the brain (Bishop, Lu et al. 2010) and increased susceptibility to the long-term effects of oxidative stress and inflammation (Joseph, Shukitt-Hale et al. 2005). Cell loss which takes place during normal aging is thought to occur primarily due to oxidative stress as a result of free radicals produced by an inefficient and partially uncoupled oxidative pathway. Indeed, it has been shown that a common trait in aging among different species, (*C. elegans, D. melanogaster*, mice, rats, chimpanzees, and humans) has been evidence of reduced mitochondrial function. This interpretation is further validated by the observation that significant impairment of mitochondrial function shortens lifespan in both *C. elegans* (Rea, Ventura et al. 2007) and mice (Trifunovic, Wredenberg et al. 2004; Kujoth, Hiona et al. 2005). Improvement of mitochondrial function, through the overexpression of catalase in mice, resulted in extended life spans (Schriner, Linford et al. 2005).

With aging and the decline of mitochondrial function, neurons in the brain become more vulnerable to age-dependent pathologies, as well as cell death. This results in a loss of connections between neurons, as well as impaired neuronal function (loss of neurotransmitters, absence of firing). There is also increased evidence that neurons respond to unrepaired DNA damage by silencing gene expression through epigenetic mechanisms, thus leading to further suppression of cell functions. Additionally, aging neuronal cells show in all species an increased expression of genes involved in stress response pathways.

Many hallmarks of these changes are observed in in vitro culture of aging neuronal cells, which show decreased neurite outgrowth and process formation. A decrease that could be reversed by neuronal growth factors (Rozovsky, Wei et al. 2005).

Neurodegenerative Disorders

Neurodegenerative diseases are a heterogeneous group of disorders characterized by gradually progressive, selective loss of anatomically or physiologically related neuronal systems. Prototypical examples include Alzheimer's disease (AD), Parkinson's disease (PD), amyotrophic lateral sclerosis (ALS), and Huntington's disease (HD).

The early stages of neurodegeneration share many of the same hallmarks as the decline seen in aging. It is interesting to note that diseases such as Alzheimer's disease show an increased incidence with age, with over 50% of adults over the age of 85 presenting with the disease (Hebert, Scherr et al. 2003). As discussed above, declining mitochondrial function appears to be a hallmark of aging. This decline in neuronal function is likely to have a significant impact on neuronal populations with large bioenergetic demands, one such set of neurons are the large pyramidal neurons which degenerate in Alzheimer's disease (Bishop, Lu et al. 2010). The decline of these classes of neurons in response to impaired mitochondrial function may be responsible for the onset of neurodegenerative disease. The effects of neurodegenerative disorders on neuronal survival can be modeled in vitro. When N2 neuronal cells are incubated with A-beta (AP) peptide, which is thought to be the causative agent of Alzheimer's disease, there is a significant impact on neurite outgrowth, which can be reversed by anti-oxidants. Manczak et al. (2010) *J Alzheimers Dis.* 20 Suppl 2:S609-31.

The most common form of cell death in neurodegeneration is via the intrinsic mitochondrial apoptotic pathway. This pathway controls the activation of caspase-9 by regulating the release of cytochrome c from the mitochondrial intermembrane space. The concentration of ROS, normal byproducts of mitochondrial respiratory chain activity, is mediated in part by mitochondrial antioxidants, such as manganese superoxide dismutase (SOD2) and glutathione peroxidase. Overproduction of ROS (oxidative stress) is a central feature of all neurodegenerative disorders. In addition to the generation of ROS, mitochondria are also involved with life-sustaining functions, including calcium homeostasis, mitochondrial fission and fusion, the lipid concentration of the mitochondrial membranes, and the mitochondrial permeability transition (MPT). Mitochondrial disease leading to neurodegeneration is likely, at least on some level, to involve all of these functions (DiMauro and Schon, 2008).

There is evidence that mitochondrial dysfunction and oxidative stress play a causal role in neurodegenerative disease pathogenesis, including in four of the more well known diseases: Alzheimer's disease, Parkinson's disease, Huntington's disease, and amyotrophic lateral sclerosis (also known as Lou Gehrig's disease).

Alzheimer's disease (AD) is characterized clinically by progressive cognitive decline, and pathologically by the presence of senile plaques composed primarily of amyloid-β peptide (Aβ) and neurofibrillary tangles made up mainly of hyperphosphorylated tau. About 5-10% of cases are familial, occurring in an early-onset, autosomal-dominant manner. Three proteins are known to be associated with such familial cases: amyloid precursor protein (APP)—which is cleaved sequentially by ρ- and γ-secretases to produce Aβ—and presenilins 1 and 2 (PS1 and PS2), one or the other of which is a component of each γ-secretase complex. Extensive literature supports a role for mitochondrial dysfunction and oxidative damage in the pathogenesis of AD. Oxidative damage occurs early in the AD brain, before the onset of significant plaque pathology. Oxidative damage also precedes Aβ deposition in transgenic APP mice, with upregulation of genes relating to mitochondrial metabolism and apoptosis occurring even earlier and co-localizing with the neurons undergoing oxidative damage.

Several pathways connecting oxidative stress and AD pathology have recently been uncovered. Oxidative stress may activate signaling pathways that alter APP or tau processing. For example, oxidative stress increases the expression of β-secretase through activation of c-Jun amino-terminal kinase and p38 mitogen-activated protein kinase (MAPK), and increases aberrant tau phosphorylation by activation of glycogen synthase kinase 3. Oxidant-induced inactivation of critical molecules may also be important. In a proteomic study, the prolyl isomerase PIN1 was found to be particularly sensitive to oxidative damage. PIN1 catalyses protein conformational changes that affect both APP and tau processing. Knockout of Pin1 increases amyloidogenic APP processing and intracellular Aβ levels in mice. Pin1-knockout mice also exhibit tau hyperphosphorylation, motor and behavioral deficits, and neuronal degeneration. Oxidative induced damage of PIN1 and similarly sensitive proteins could thus be important in promoting neurodegenerative processes.

Mitochondria also play an important role in Parkinson's disease (PD) which is characterized clinically by progressive rigidity, bradykinesia and tremor, and pathologically by loss of pigmented neurons in the substantia nigra and the presence of Lewy bodies—distinctive cytoplasmic inclusions that immunostain for α-synuclein and ubiquitin.

Mitochondria were first implicated in PD because MPTP (1-methyl 4-phenyl-1,2,3,6-tetrahydropyridine), whose metabolite MPP+ inhibits complex I of the mitochondrial electron-transport chain, caused parkinsonism in designer-drug abusers. This model has since been refined in laboratory animals, in which chronic infusion of rotenone—another complex-I inhibitor—or MPTP results clinically in a parkinsonian phenotype and pathologically in nigral degeneration with cytoplasmic inclusions immunoreactive for α-synuclein and ubiquitin. The mechanism of toxicity in these complex-I inhibition models probably involves oxidative stress. Complex-I inhibition and oxidative stress were shown to be relevant to naturally occurring PD when complex-I deficiency and glutathione depletion were found in the substantia nigra of patients with idiopathic PD and in patients with pre-symptomatic PD.

Many of the genes associated with PD also implicate mitochondria in disease pathogenesis. So far, mutations or polymorphisms in mtDNA and at least nine named nuclear genes have been identified as causing PD or affecting PD risk: α-synuclein, parkin, ubiquitin carboxy-terminal hydrolase L1, DJ-1, phosphatase and tensin homologue (PTEN)-induced kinase 1 (PINK1), leucine-rich-repeat kinase 2 (LRRK2), the nuclear receptor NURR1, HTRA2, and tau. Of the nuclear genes, α-synuclein, parkin, DJ-1, PINK1, LRRK2, and HTRA2 directly or indirectly involve mitochondria. In a small number of cases, inherited mtDNA mutations result in parkinsonism, typically as one feature of a larger syndrome. In one family, the Leber's optic atrophy G11778A mutation was associated with 1-DOPA-responsive parkinsonism, variably co-occurring with dementia, dystonia, ophthalmoplegia and ataxia. Notably, this mutation is in a subunit of complex I. Mutations in the nuclear-encoded mtDNA polymerase-γ (POLG) gene impair mtDNA replication and result in multiple mtDNA deletions, typically causing chronic progressive external ophthalmoplegia and myopathy. In such families, POLG mutations also cosegregate with parkinsonism.

Amyotrophic lateral sclerosis (ALS) is characterized clinically by progressive weakness, atrophy and spasticity of muscle tissue, reflecting the degeneration of upper and lower motor neurons in the cortex, brainstem and spinal cord. Approximately 90% of cases are sporadic (SALS) and 10% are familial (FALS). About 20% of familial cases are caused by mutations in Cu/Zn-superoxide dismutase (SOD1). In both SALS and FALS, postmortem and biopsy samples from the spinal cord, nerves and muscles show abnormalities in mitochondrial structure, number and localization. Defects in activities of respiratory chain complexes have also been detected in muscle and spinal cord.

Huntington's disease (HD) is characterized clinically by chorea, psychiatric disturbances, and dementia, and pathologically by loss of long projection neurons in the cortex and striatum. HD is inherited in an autosomal dominant manner, and is due to expansion of a CAG trinucleotide repeat in the huntingtin (HTT) gene, which gives rise to an expanded polyglutamine stretch in the corresponding protein. The normal number of CAG (Q) repeats is less than 36; repeat numbers greater than 40 are associated with human disease. Various lines of evidence demonstrate the involvement of mitochondrial dysfunction in HD. Nuclear magnetic resonance spectroscopy reveals increased lactate in the cortex and basal ganglia. Biochemical studies show decreased activities of complexes II and III of the electron-transport chain in the human HD brain. In striatal cells from mutant Hu-knock-in mouse embryos, mitochondrial respiration and ATP production are significantly impaired.

An aspect of the invention is a method of treating a neurodegenerative disease, age-related neuronal death or dysfunction. As used herein, "neurodegenerative disease" or, equivalently, "neurodegenerative disorder", refers to any condition involving progressive loss of functional neurons in the central nervous system. In one embodiment, the neurodegenerative disease is associated with age-related cell death. Exemplary neurodegenerative diseases include, without limitation, Alzheimer's disease, Parkinson's disease, Huntington's disease, amyotrophic lateral sclerosis (also known as ALS and as Lou Gehrig's disease), as well as AIDS dementia complex, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Kennedy's disease, Krabbe disease, Lyme disease, Machado-Joseph disease, multiple sclerosis, multiple system atrophy, neuroacanthocytosis, Niemann-Pick disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome.

In one embodiment, the method is used to treat age-related neuronal death or dysfunction. Such method is directed to neurodegeneration that is not attributable to a specific neurodegenerative disease, e.g., Alzheimer's disease, amyotrophic lateral sclerosis, Huntington's disease, and Parkinson's disease.

In one embodiment, a neurodegenerative disease is selected from the group consisting of Alzheimer's disease, amyotrophic lateral sclerosis, Huntington's disease, and Parkinson's disease.

In one embodiment, a neurodegenerative disease is Alzheimer's disease.

The method includes the step of administering to a subject in need of treatment of a neurodegenerative disease a therapeutically effective amount of a urolithin or a precursor thereof, thereby treating the neurodegenerative disease.

Figure 1:
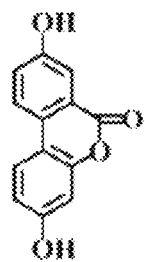
FIG. 1 depicts structural formulas for urolithin A (UA), ellagic acid (EA), tellimagrandin (TL), punicalagin (PA), and punicalin (PB).
Figure 1:
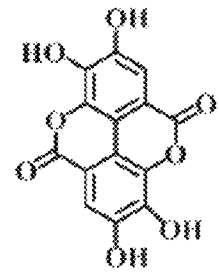
Figure 1:
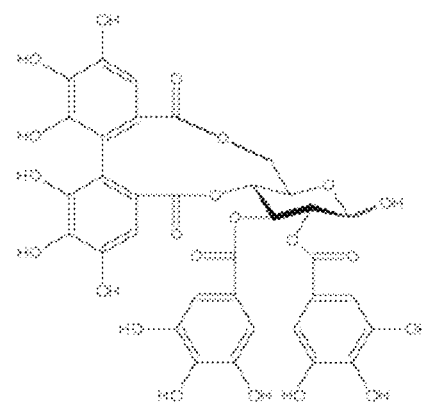
Figure 1:
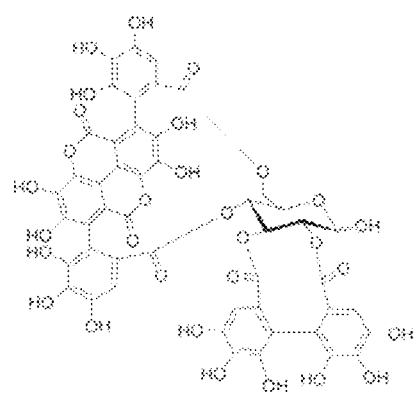
Figure 1:
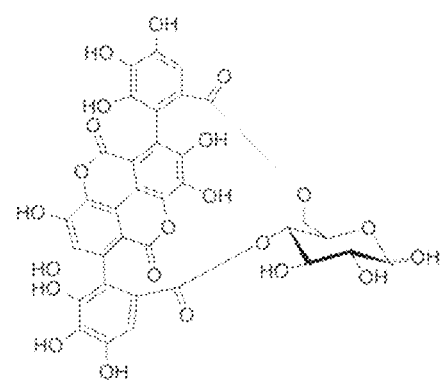

In accordance with this and other methods of the invention, a "urolithin," as used herein, refers to any one or combination of urolithin A, urolithin B, urolithin C, and urolithin D (see, for example, FIG. 1 and FIG. 2). In one embodiment, a urolithin is urolithin A, urolithin B, urolithin C, urolithin D, or any combination of urolithin A, urolithin B, urolithin C, and urolithin D. In one embodiment, a urolithin is urolithin A, urolithin B, or a combination of urolithin A and urolithin B. In one embodiment, a urolithin is urolithin A. In one embodiment, a urolithin is provided as an isolated urolithin, e.g., isolated from a natural source or prepared by total synthesis. Isolated urolithins may be synthesized de novo. See, for example, US Pat. Application Publication No. 2008/0031862 to Ghosal, the entire contents of which are incorporated herein by reference.

In one embodiment, urolithin A (3,8-Dihydroxydibenzo-α-pyrone) was synthesized in a two-stage synthesis as follows. Stage 1 is a copper-catalyzed reaction that occurs in the presence of a base (Hurtley reaction) where the starting materials 2-bromo-5-methoxybenzoic acid and resorcinol are reacted together to generate the dihydro-dibenzopyrone scaffold. In Stage 2 the demethylation of the benzopyrone with $BBr_3$ yields 3,8-Dihydroxydibenzo-α-pyrone (urolithin A).

A mixture of 2-bromo-5-methoxybenzoic acid 1 (27.6 g), resorcinol 2 (26.3 g) and sodium hydroxide (10.5 g) in water (120 mL) was heated under reflux for 1 hour. A 5% aqueous solution of copper sulfate (3.88 g of $CuSO_4$, $5H_2O$ in 50 mL water) was then added and the mixture was refluxed for additional 30 minutes. The mixture was allowed to cool down to room temperature and the solid was filtered on a Buchner filter. The residue was washed with cold water (50 mL) to give a pale red solid (38.0 g) which was triturated in hot MeOH (200 mL). The suspension was left overnight at 4° C. The resultant light red precipitate was filtered and washed with cold MeOH (75 mL) to yield the title compound 3 as a pale brown solid. $^1$H NMR is in accordance with the structure of 3.

To a suspension of 3 (10.0 g; 41 mmol; 1.0 eq.) in dry dichloromethane (100 mL) was added at 0° C. a 1 M solution of boron tribromide in dry dichloromethane (11.93 mL of pure $BBr_3$ in 110 mL of anhydrous dichloromethane). The mixture was left at 0° C. for 1 hour and was then allowed to warm up to room temperature. The solution was stirred at that temperature for 17 hours. The yellow precipitate was filtered and washed with cold water (50 mL) to give a yellow solid which was heated to reflux in acetic acid (400 mL) for 3 hours. The hot solution was filtered quickly and the precipitate was washed with acetic acid (50 mL) then with diethyl ether (100 mL) to yield the title compound 4 as a yellow solid. Structure and purity were determined by $^1$H and $^{13}$C-NMR.

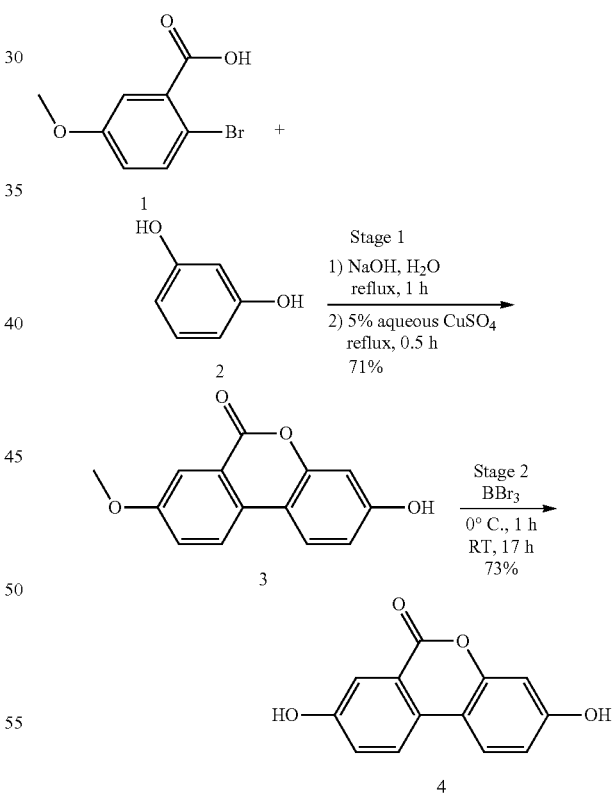

In one embodiment, a "urolithin" as used herein is or can include a glucuronated, methylated, or sulfated urolithin.

In accordance with this and other methods of the invention, a "urolithin precursor," as used herein, refers to an ellagitannin or an ellagitannin metabolite, including but not limited to ellagic acid (EA). In one embodiment, a urolithin precursor is punicalagin (PA). In one embodiment, a urolithin precursor is punicalin (PB). See, for example, FIG. 1.

In one embodiment, a urolithin precursor is ellagic acid (EA). In one embodiment, a urolithin precursor is provided as an isolated urolithin precursor, e.g., isolated from a natural food source or prepared by total synthesis. Isolated urolithin precursors are usually purified from natural sources or synthesized de novo; some urolithin precursors, including EA, are commercially available from suppliers, such as Sigma Aldrich.

Also in accordance with this and other methods of the invention, precursors of urolithins also include natural foods containing ellagitannins and ellagic acid, especially natural foods that are rich in ellagitannins, ellagic acid, or both ellagitannins and ellagic acid. Such foods include certain berries, grapes, pomegranates, rose hips, and nuts. In one embodiment, the natural food is pomegranate.

Additionally, precursors of urolithins include processed foods and drinks prepared from such natural foods. The processed food can take any form, including, for example, jams, jellies, preserves, pastes, spreads, juices, wines, extracts, concentrates, and the like. In one embodiment, the processed food is pomegranate juice.

In one embodiment, a urolithin precursor is provided as an extract, e.g., a fruit extract.

In one embodiment, a urolithin precursor is provided as concentrate, e.g., a fruit concentrate or fruit juice concentrate.

The method of the invention can be used alone or in combination with any method or compound known to be useful to treat neurodegenerative disease. For example, In one embodiment, the method of the invention can be combined with use of any one or more of acetylcholinesterase inhibitors, such as donezepil (Aricept®), galantamine (Razadyne®), and rivastigmine (Exelon®), and N-methyl D-aspartate (NMDA) receptor antagonists, such as memantine (Namenda®).

An aspect of the invention is a method of improving cognitive function. As used herein, "cognitive function" refers to any mental process that involves symbolic operations, e.g., perception, memory, attention, speech comprehension, speech generation, reading comprehension, creation of imagery, learning, and reasoning. In one embodiment, "cognitive function" refers to any one or more of perception, memory, attention, and reasoning. In one embodiment, "cognitive function" refers to memory.

The method includes the step of administering to a subject in need of improved cognition a therapeutically effective amount of a urolithin or a precursor thereof, thereby improving cognitive function.

Methods for measuring cognitive function are well known and can include, for example, individual or battery tests for any aspect of cognitive function. One such test is the Prudhoe Cognitive Function Test. Margallo-Lana et al. (2003) *J Intellect Disability Res.* 47:488-492. Another such test is the Mini Mental State Exam (MMSE), which is designed to assess orientation to time and place, registration, attention and calculation, recall, language use and comprehension, repetition, and complex commands. Folstein et al. (1975) *J Psych Res.* 12:189-198. Other tests useful for measuring cognitive function include the Alzheimer Disease Assessment Scale-Cognitive (ADAS-Cog) (Rosen et al. (1984) *Am J Psychiatry.* 141(11):1356-64) and the Cambridge Neuropsychological Test Automated Battery (CANTAB) (Robbins et al. (1994) *Dementia.* 5(5):266-81). Such tests can be used to assess cognitive function in an objective manner, so that changes in cognitive function, for example in response to treatment in accordance with methods of the invention, can be measured and compared.

The method of the invention can be used alone or in combination with any method or compound known to improve cognitive function. For example, In one embodiment, the method of the invention is combined with use of caffeine or nicotine or both.

In one embodiment, the subject does not have a cognitive disorder. For example, the method can be used to enhance cognitive function in a subject having normal cognitive function.

An aspect of the invention is a method of treating a cognitive disorder. As used herein, a cognitive disorder refers to any condition that impairs cognitive function. In one embodiment, "cognitive disorder" refers to any one or more of delirium, dementia, learning disorder, attention deficit disorder (ADD), and attention deficit hyperactivity disorder (ADHD). In one embodiment, the cognitive disorder is a learning disorder. In one embodiment, the cognitive disorder is attention deficit disorder (ADD). In one embodiment, the cognitive disorder is attention deficit hyperactivity disorder (ADHD).

The method includes the step of administering to a subject in need of treatment of a cognitive disorder a therapeutically effective amount of a urolithin or a precursor thereof, to treat the cognitive disorder.

The method of the invention can be used alone or in combination with any method or compound known to be useful to treat a cognitive disorder. For example, In one embodiment, the method of the invention is combined with use of a stimulant, such as methylphenidate (e.g., Ritalin®), dextroamphetamine (Dexedrine), mixed amphetamine salts (Adderall®), dextromethamphetamine (Desoxyn®), and lisdexamphetamine (Vyvanase®).

An aspect of the invention is a method of treating or preventing a stress-induced or stress-related cognitive dysfunction. As used herein, a "stress-induced or stress-related cognitive dysfunction" refers to a disturbance in cognitive function that is induced or related to stress. The method includes the step of administering to a subject in need of treatment or prevention of a stress-induced or stress-related cognitive dysfunction a therapeutically effective amount of a urolithin or a precursor thereof, to treat or prevent the stress-induced or stress-related cognitive dysfunction.

Mood Disorders

Brain tissue requires a high level of energy for its metabolism, including the maintenance of the transmembrane potential, signal transduction and synaptic remodeling. An increase of psychiatric symptoms and disorders, in particular depression, is likely present in patients with mitochondrial disorders.

Mitochondrial structure and function, measured by a variety of different techniques, have been shown to be abnormal in patients with mood disorders, including major depression as well as in the other affective spectrum disorders.

Two studies revealed that a several-fold increased likelihood of developing depression can be maternally inherited along with the mtDNA, which strongly argues that mtDNA sequence variants may induce mitochondrial dysfunction that can predispose individuals towards the development of depression (Boles et al., 2005; Burnett et al., 2005).

The relationship between mitochondrial dysfunction and unipolar depression has been explored in several studies. In studies of postmortem brain from subjects with probable or diagnosed major depression, of whom most subjects were (probably) medicated, no increase of the common 5 kb mtDNA deletion could be detected (Kato et al., 1997; Sabunciyan et al., 2007; Shao et al., 2008 Stine et al., 1993).

Alterations of translational products linked to mitochondrial function were found in the frontal, prefrontal and tertiary visual cortices (Karry et al., 2004; Whatley et al., 1996). Alterations of four mitochondrial located proteins in the anterior cingulate cortex have been reported (Beasley et al., 2006). Decreased gene expression for 6 of 13 mtDNA-encoded transcripts in frontal cortex tissue (Brodmann areas (BA) 9 and 46) (Shao et al., 2008), and of nDNA-encoded mitochondrial mRNA and proteins in the cerebellum, have also been reported in major depression (Ben-Shachar and Karry, 2008). Levels of an electron transport chain complex I subunit (NDUFS7), and complex I activity, in postmortem prefrontal cortex were found to be below or at the lowest range of the normal controls in half of the cases of major depressive disorder in a recent study (Andreazza et al., 2010). In the two latter studies, the authors were unable to detect any effect of medication on the results.

Decreases of respiratory chain enzyme ratios and ATP production rates, and an increased prevalence of small mtDNA deletions (but not of the common 5 kb mtDNA deletion), were found in muscle from patients with a lifetime diagnosis of major unipolar depression with concomitant physical symptoms. Medication did not seem to influence the results (Gardner et al., 2003b). Clinical relevance was suggested by the finding that essentially every depressed subject with very high degrees of somatic complaints demonstrated low ATP production rates in biopsied muscle (Gardner and Boles, 2008a).

An aspect of the invention is a method of treating a mood disorder (also known as an affective disorder). As used herein, a "mood disorder" refers to a disturbance in emotional state, such as is set forth in the *Diagnostic and Statistical Manual of Mental Disorders*, published by the American Psychiatric Association. Mood disorders include but are not limited to major depression, postpartum depression, dysthymia, and bipolar disorder. In one embodiment, the mood disorder is major depression.

The method includes the step of administering to a subject in need of treatment of a mood disorder a therapeutically effective amount of a urolithin or a precursor thereof, to treat the mood disorder.

The method of the invention can be used alone or in combination with any method or compound known to be useful to treat a mood disorder. For example, In one embodiment, the method of the invention is combined with use of an antidepressant agent. Antidepressant agents are well known in the art and include selective serotonin reuptake inhibitors (SSRIs), serotonin-norepinephrine reuptake inhibitors (SNRIs), noradrenergic and specific serotonergic antidepressants, norepinephrine reuptake inhibitors, norepinephrine-dopamine reuptake inhibitors, selective serotonin reuptake inhibitors, norepinephrine-dopamine disinhibitors, tricyclic antidepressants, and monamine oxidase inhibitors.

An aspect of the invention is a method of treating or preventing a stress-induced or stress-related mood disorder. As used herein, a "stress-induced or stress-related mood disorder" refers to a disturbance in emotional state that is induced or related to stress. Such mood disorders are sometimes referred to as reactive mood disorders and are to be distinguished from other mood disorders, e.g., so-called organic mood disorders. The method includes the step of administering to a subject in need of treatment or prevention of a stress-induced or stress-related mood disorder an effective amount of a urolithin or a precursor thereof, to treat or prevent the stress-induced or stress-related mood disorder.

An aspect of the invention is a method of treating an anxiety disorder. As used herein, an "anxiety disorder" refers to a dysfunctional state of fear and anxiety, e.g., fear and anxiety that is out of proportion to a stressful situation or the anticipation of a stressful situation. In one embodiment, an anxiety disorder is any one or combination of generalized anxiety disorder, panic disorder, panic disorder with agoraphobia, agoraphobia, social anxiety disorder, obsessive-compulsive disorder, and post-traumatic stress disorder. In one embodiment, an anxiety disorder is any one or combination of generalized anxiety disorder, obsessive-compulsive disorder, panic disorder, post-traumatic stress disorder, and social anxiety disorder. In one embodiment, an anxiety disorder is generalized stress disorder. In one embodiment, an anxiety disorder is post-traumatic stress disorder. In one embodiment, an anxiety disorder is a stress-induced anxiety disorder.

The method includes the step of administering to a subject in need of treatment of an anxiety disorder a therapeutically effective amount of a urolithin or a precursor thereof, to treat the anxiety disorder.

The method of the invention can be used alone or in combination with any method or compound known to be useful to treat an anxiety disorder. For example, In one embodiment, the method of the invention is combined with use of any one or combination of psychotherapy, benzodiazepines, buspirone (Buspar®), or beta-blockers.

Benzodiazepines are well known in the art and include, without limitation, clonazepam (Klonopin®), lorazepam (Ativan®), and alprazolam (Xanax®). Additional drugs that may be used in combination with the methods of the invention include imipramine (Tofranil®) and venlafaxine (Effexor®).

An aspect of the invention is a method of treating or preventing a stress-induced or stress-related anxiety disorder. As used herein, a "stress-induced or stress-related anxiety disorder" refers to a dysfunctional state of fear and anxiety that is induced or related to stress. Such anxiety disorders are sometimes referred to as reactive anxiety disorders and are to be distinguished from other anxiety disorders, e.g., so-called organic anxiety disorders. The method includes the step of administering to a subject in need of treatment or prevention of a stress-induced or stress-related anxiety disorder an effective amount of a urolithin or a precursor thereof, to treat or prevent the stress-induced or stress-related anxiety disorder.

An aspect of the invention is a method of promoting neurite outgrowth. In one embodiment, the method is an in vitro method. In one embodiment, the method is an in vivo method. As used herein, a "neurite" refers to any projection from the cell body of a neuron. In one embodiment, such projection is an axon. In one embodiment, such projection is a dendrite. The term is frequently used when speaking of immature or developing neurons, especially of cells in culture, because it can be difficult to tell axons from dendrites before differentiation is complete. Neurites are often packed with microtubule bundles, the growth of which is stimulated by nerve growth factor (NGF), as well as tau proteins, microtubule associated protein 1 (MAP1), and microtubule associated protein 2 (MAP2). The neural cell adhesion molecule N-CAM simultaneously combines with another N-CAM and a fibroblast growth factor receptor to stimulate the tyrosine kinase activity of that receptor to induce the growth of neurites.

Neurite outgrowth can be measured morphologically or functionally. Morphological measurement typically entails microscopic examination with measurement of the length and/or number of neurites.

As used herein, "promoting" refers to enhancing or inducing. In one embodiment, "promoting" means inducing. For example, neurite outgrowth in a negative control sample may be negligible, while neurite outgrowth in an experimental or treatment sample may be non-negligible. In one embodiment, "promoting" means enhancing. For example, neurite outgrowth in a negative control sample may be non-negligible, while neurite outgrowth in an experimental or treatment sample may be statistically significantly greater than the negative control. Of course "promoting" as used herein can encompass both enhancing and inducing.

In one embodiment, the method includes the step of contacting a nerve cell with an effective amount of a urolithin or a precursor thereof, to promote neurite outgrowth.

In one embodiment, the method includes the step of administering to a subject in need thereof a therapeutically effective amount of the urolithin or precursor thereof, to promote neurite outgrowth.

The methods of the invention can be used alone or in combination with any method or compound known to be useful to promote neurite outgrowth. For example, In one embodiment, a method of the invention can be combined with use of any one or more of NGF, tau protein, MAP1, MAP2, N-CAM, or an agent that induces the expression of any one or more of NGF, tau protein, MAP1, MAP2, N-CAM, or fibroblast growth factor receptor.

Using Neuronal Cells in vitro to Screen Compounds for Neuroprotective Activities In the processes of aging and neurodegeneration, the progressive deterioration of cognitive function is essentially due to the loss of entities sustaining neuronal communication. These entities are essentially composed of neuronal cell bodies, neurites and synaptic contacts that connect them to target cells. Neurons display very complex morphologies. The most complex neuronal cell types, such as motor neurons extending axonal processes up to one meter long or nigral dopaminergic neurons making more than 150,000 synaptic contacts, will often be the most vulnerable in normal aging or disease. To maintain such a complex architecture and effectively convey electrical and neurochemical signals, neurons heavily rely on energy supply. Therefore, axonal transport, synaptic activity, and the maintenance of ion gradients highly depend on mitochondrial function. To carry on these demanding cellular functions, neurons experience over time difficulties to sustain the delicate balance of mitochondrial activity and ensuing oxidative stress. Such imbalance is often considered the cause of neuronal dysfunction or premature degeneration.

Therefore, any treatment promoting neuronal survival, or the formation of the neuronal processes and synaptic contacts that build up neuronal complex architecture, is expected to positively impact neuronal functions. The measurement of compound effects on neuronal function typically relies on the tedious monitoring of animal behavioral outcomes, which is not amenable to medium- or high-throughput screening of biological activities. In vitro models based on neuroblastoma cell lines or primary neuronal cultures represent an accepted proxy to assess compound effects on crucial morphological parameters, which will reflect the ability of neurons to sustain their normal function in the mammalian brain. Indicators such as the number of processes, their length, or complexity will reveal compound effects on critical steps of intracellular signaling. Although one should keep in mind that such parameters only indirectly reflect the performance of higher brain functions, they provide a valuable appraisal of compound efficacy that may translate into improved cognitive or motor functions in normal or diseased conditions.

Metabolic Disorders

Mitochondrial function in key metabolic tissues (liver, muscle, adipose tissue, pancreas) is involved in the pathogenesis of metabolic diseases. In each of these tissues, mitochondrial oxidative activity must be appropriate to fully oxidize nutrient loads, particularly fatty acids. Failure of complete oxidation can lead to accumulation of lipid intermediates, incomplete fatty acid oxidation products, and ROS. Altogether, these cellular events contribute to fat accumulation, insulin resistance, altered insulin secretion, low grade inflammation, and oxidative stress, which are all components of type II diabetes mellitus and obesity.

The importance of mitochondrial activity in the pathogenesis of metabolic diseases has been established in several studies in humans. For example, insulin resistance in skeletal muscle has been associated with a defect in mitochondrial oxidative phosphorylation, where a 30% reduction in mitochondrial activity is observed in insulin-resistant offspring of patients with type 2 diabetes as compared to control subjects. Petersen K F, et al. (2004) *New Engl J Med*. 350:664-71. It has also been observed that obese patients display a 20% decrease in mitochondrial activity along with a 35% reduction in mitochondrial size compared to healthy lean subjects. Petersen K F, et al. (2003) *Science* 300:1140-2. Finally, age-associated decline in mitochondrial function contributes to insulin resistance in the elderly. Accordingly, a 40% reduction in mitochondrial oxidative and phosphorylation activity has been reported in the elderly compared to young subjects. These observations link disturbance in mitochondrial function to metabolic disorders, especially "diabesity" (Kelley D E, et al. (2002) *Diabetes* 51:2944-50).

Mitochondrial oxidative activity, also referred to as oxidative phosphorylation, can be considered as a key determinant underlying the risk of metabolic diseases. Reductions in mitochondrial activity can be mediated by genetic factors (e.g., family history, ethnicity), epigenetic mechanisms, developmental exposures, eating behavior and aging.

When sustained fuel excess (e.g., from overeating or impaired fat storage) surpasses energetic demands and/or oxidative capacity, and/or appropriate compensatory mechanisms are insufficient (for example, due to inactivity or failure of mitochondria to adapt to higher cellular oxidative demands), there is an increased risk of metabolic disorders. The resulting lipid accumulation and oxidative stress can alter transcriptional responses and damage mitochondria, further reducing oxidative phosphorylation capacity, compounding the deleterious effects of fuel excess elevating the risk of metabolic disorders.

The sufficiency fully to oxidize fatty acids resides in the balance between: (i) the net mitochondrial oxidative activity (determined by the need to generate energy to meet cellular demands, e.g., contraction and ion transport), and (ii) fuel availability (determined by food intake, adiposity, and adipose storage capacity). Balance is achieved when oxidative activity equals or exceeds fuel loads.

Under normal homeostatic conditions, both oxidative activity and cellular fuel availability can be altered to ensure that mitochondrial function is appropriate for the ambient metabolic environment. For example, cellular demand for energy can be increased through exercise, and fuel availability can be reduced through weight loss and/or reduced food intake. In this context, inter-individual variations in oxidative capacity and/or activity, fuel load, or ability to modulate mitochondrial activity (acute response), increase mitochondrial capacity (chronic response), or resolve oxidative stress could determine the set point of metabolic balance. Such differences could become prominent particularly in an obesogenic environment (one characterized by environments that promote increased overall food intake, intake of nonhealthful foods, and physical inactivity). Therefore, individuals with a high oxidative capacity or adaptive responses would have high tolerance to large fuel loads. Conversely, individuals with reduced oxidative capacity and/or suboptimal adaptive responses would be intolerant to moderate high fuel loads, leading to lipid accumulation, incomplete oxidation, production of ROS, and insulin resistance.

With time, insufficient compensation will result in chronic insulin resistance and metabolic disorders. Insufficient oxidative capacity could be resolved by compensatory mechanisms that increase oxidative capacity (e.g., exercise) or decrease fuel load (weight loss). However, these lifestyle changes appear usually insufficient or not achievable for most overweight/obese and type 2 diabetic or pre-diabetic subjects.

Mitochondria are particularly important for skeletal muscle function, given the high oxidative demands imposed on this tissue by intermittent contraction. Mitochondria play a critical role in ensuring adequate levels of ATP needed for contraction by the muscle sarcomere. This high-level requirement for ATP by sarcomeres has likely contributed to the distinct subsarcolemmal and sarcomere-associated populations of mitochondria in muscle. Moreover, muscle cells must maintain metabolic flexibility, the ability to rapidly modulate substrate oxidation as a function of ambient hormonal and energetic conditions. For example, healthy muscle tissue predominantly oxidizes lipid in the fasting state, as evidenced by low respiratory quotient (RQ), with subsequent transition to carbohydrate oxidation (increased RQ) during the fed state. Availability of fuels, particularly lipids, and capacity to oxidize them within mitochondria are also critical for sustained exercise. Thus, mitochondrial functional capacity is likely to directly affect muscle metabolic function and, because of its large contribution to total body mass, to have a significant impact on whole-body metabolism. This possibility is supported by the findings of increased mitochondrial content in skeletal muscle in an individual with hypermetabolism and resistance to weight gain (Luft syndrome).

Insulin Resistance and Diabetes Mellitus

Skeletal muscle is the largest insulin-sensitive organ in humans, accounting for more than 80% of insulin-stimulated glucose disposal. Thus, insulin resistance in this tissue has a major impact on whole-body glucose homeostasis. Indeed, multiple metabolic defects have been observed in muscle from insulin-resistant but normoglycemic subjects at high risk for diabetes development, including: (i) reduced insulin-stimulated glycogen synthesis; (ii) alterations in insulin signal transduction; and (iii) increased muscle lipid accumulation. Although it remains unclear at present whether any of these defects play a causal role in insulin resistance, intramyocellular lipid excess strongly correlates with the severity of insulin resistance, even after correction for the degree of obesity, and has been observed in muscles of multiple fiber types. Moreover, lipid excess has been linked experimentally to induction of insulin resistance and alterations in insulin signal transduction. Thus, one possible mechanism by which impaired mitochondrial function might contribute to insulin resistance is via altered metabolism of fatty acids. Increased tissue lipid load, as with obesity, and/or sustained inactivity, may lead to the accumulation of fatty acyl coenzyme A (CoA), diacylglycerols, ceramides, products of incomplete oxidation, and ROS, all of which have been linked experimentally to reduced insulin signaling and action. Additional mechanisms potentially linking impaired mitochondrial oxidative function to insulin resistance include: (i) reduced ATP synthesis for energy-requiring functions such as insulin-stimulated glucose uptake; (ii) abnormalities in calcium homeostasis (necessary for exercise-induced glucose uptake); and (iii) reduced ATP production during exercise, potentially contributing to reduced aerobic capacity, muscle fatigue, and decreased voluntary exercise over time—further feeding a vicious cycle of inactivity-fueled insulin resistance.

Mitochondrial capacity is central to the key function of the pancreatic beta (β)-cell-regulated insulin secretion. Both rapid (first phase) and more prolonged (second phase) insulin secretion are dependent on glucose metabolism and mitochondrial oxidative capacity; glucose oxidation increases the ATP/ADP ratio, inhibiting plasma membrane K-ATP channels and allowing voltage-gated calcium channels to open. Increased cytoplasmic calcium then triggers exocytosis of plasma-membrane docked insulin granules (first phase). Subsequent recruitment of granules to the plasma membrane (second phase) appears to depend on mitochondrial metabolites produced by anaplerosis. Mitochondrial metabolism is also required for the transient, controlled production of ROS, which is required for the mitochondrial signaling pathways that trigger granule exocytosis.

Mitochondrial diabetes only develops upon aging, with an average age of onset between 35 and 40 yr for maternally inherited diabetes with deafness (MIDD) and 48 yr for 14577 T/C, a mitochondrial DNA missense mutation in maternally inherited type 2 diabetes. This contrasts with the early childhood onset of diabetes in syndromes such as maturity-onset diabetes of the young 2 (MODY2), in which a mutation in glucokinase, the first step of glycolysis, results in attenuated glucose-stimulated ATP generation and insulin secretion. These data suggest that mitochondrial diabetes is more likely to result from a gradual deterioration of β-cell function, rather than from an acute functional impairment due to insufficient ATP production.

Mitochondrial function in tissues involved in the pathogenesis of diabetes mellitus (liver, muscle, adipose tissue, and pancreatic β-cells) is critical for multiple aspects of cellular metabolism. In each of these tissues, mitochondrial oxidative activity must be appropriate to fully oxidize nutrient loads, particularly fatty acids. Failure of complete oxidation can lead to accumulation of lipid intermediates, incomplete fatty acid oxidation products, and ROS, inducing both insulin resistance (muscle, liver, adipose) and altered secretion β-cells).

Mild deficiencies in mitochondrial activity, and/or an inability to increase activity and capacity in response to cellular energy demand, could explain the reduced exercise ability seen in individuals with a family history of diabetes mellitus. Over time, this phenotype could contribute to reduced voluntary exercise and increase the likelihood of an imbalance between mitochondrial activity and fatty acid load. Secondly, chronic imbalance in energy metabolism due to overnutrition, obesity, and inactivity could directly contribute to increased cellular and mitochondrial ROS production. In turn, excessive ROS can induce both insulin resistance and mitochondrial dysfunction. For example, a high-fat, high-sucrose diet in the diabetes-prone C57BL6 mouse causes mitochondrial alterations in parallel with enhanced ROS production and impaired insulin sensitivity. Similarly, exposure of muscle cells in vitro to saturated fatty acids or high-fat feeding in mice results in alterations in mitochondrial structure and insulin resistance, both of which are reversed by antioxidants. Thus, oxidative stress can induce mitochondrial dysfunction in parallel with insulin resistance—perhaps an adaptive response aimed at limiting further oxidative damage. Importantly, resolution of oxidative stress can reverse insulin resistance.

Muscle Performance

In other embodiments, the invention provides methods for enhancing muscle performance by administering a therapeutically effective amount of a mitochondria-enhancing or -activating extract, formulation or compound. For example, extracts containing ellagitannins or ellagic acid, or compositions containing ellagitannins, ellagic acid, or urolithins behave to activate mitochondria and may be useful for improving physical endurance (e.g., ability to perform a physical task such as exercise, physical labor, sports activities), inhibiting or retarding physical fatigue, enhancing blood oxygen levels, enhancing energy in healthy individuals, enhancing working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering an amount of an ellagitannin- or ellagic acid-containing natural extract, or compositions containing ellagitannins, ellagic acid or urolithin, that increase mitochondrial activity, increase mitochondrial biogenesis, and/or increase mitochondrial mass.

Sports performance refers to the ability of an athlete's muscles to perform when participating in sports activities. Enhanced sports performance, strength, speed, and endurance are measured by an increase in muscular contraction strength, increase in amplitude of muscle contraction, or shortening of muscle reaction time between stimulation and contraction. Athlete refers to an individual who participates in sports at any level and who seeks to achieve an improved level of strength, speed, or endurance in their performance, such as, for example, body builders, bicyclists, long distance runners, and short distance runners. Enhanced sports performance is manifested by the ability to overcome muscle fatigue, ability to maintain activity for longer periods of time, and have a more effective workout.

It is contemplated that the compositions and methods of the present invention will also be effective in the treatment of muscle-related pathological conditions, including myopathies, neuromuscular diseases, such as Duchenne muscular dystrophy, acute sarcopenia, for example, muscle atrophy and/or cachexia associated with burns, bed rest, limb immobilization, or major thoracic, abdominal, and/or orthopedic surgery.

Chronic Stress

Chronic stress has also been reported to have a significant effect on cognitive performance and more precisely on learning and memory processes (Sandi 2004; Sandi and Pinelo-Nava 2007). Several factors are determinant on the impact that chronic stress will have on cognitive function. The levels of stress are important in determining whether the stress will serve to facilitate cognitive function or be deleterious. It is thought that in response to stressful situations the body induces stress hormones, which produce an inverted U effect on learning, memory, and plasticity. Baldi et al. (2005) *Nonlinearity Biol Toxicol Med.* 3(1) 9-21; Joels (2006) *Trends Pharmacol Sci.* 27(5):244-50. Thus the level of stress has a great effect on cognitive function, with high levels of stress resulting in high levels of stress hormones and decreased performance.

The length of the stress, chronic vs. acute, has been also shown to play an important role, with distinct effects on cognitive function, as well as brain structure and function (Sandi and Loscertales 1999; Pinnock and Herbert 2001). Also, stress acts on the memory forming process resulting in different outcomes, with consolidation (memory storage) being facilitated by acute stress, and retrieval (memory recall) being inhibited (Roozendaal 2003). In addition, the predictability of the stress also plays a role on the severity of the effects observed on cognitive performance (Maier and Watkins 2005).

Additionally, the context in which the chronic stress occurs, as well as individual differences in stress response inherent to individuals and gender, play an important role in determining the final cognitive impact of chronic stress (Bowman, Beck et al. 2003; Shors 2004; Joels, Pu et al. 2006).

The biological basis for the effects of chronic stress is not yet well defined. However, a common observed feature is the key role of glucocorticoids in mediating both, the facilitating and impairing actions of stress, on different memory processes and phases. While the mechanism of glucocorticoids action has yet to be elucidated, it has been shown in vitro to impair neuronal outgrowth induced by nerve growth factor (NGF). Unsicker et al. (1978) *Proc Natl Acad Sci USA.* 75:3498-502. Furthermore, neuronal structure and neurite outgrowth induced by factors such as NGF correlate strongly with their neuroprotective activity, suggesting again that neuronal structure is important for cognition.

Stress and Structural Remodeling

Initially, the hippocampus was the brain region that received close attention due to the many reports indicating impairing effects of chronic stress in hippocampus-dependent memory tasks. However, intensive work is now providing evidence for a more integral impact of chronic stress throughout the brain, with major changes having also being reported for the prefrontal cortex and the amygdala. Changes in dendritic branching and synaptogenesis occurring in the amygdala are plausible candidates to participate in stress-induced mood alterations. Also, changes occurring at the level of the hippocampus and the prefrontal cortex are believed to play a key role in stress-induced mood alterations.

Hippocampus.

The hippocampus is well known for its crucial role in memory processes. Hippocampus-dependent tasks are generally affected by both acute and chronic stress manipulations. In humans, neuroimaging studies have reported hippocampal atrophy in association with stress- and glucocorticoid-related cognitive and neuropsychiatric alterations, including depression.

In rodents, a prominent and many times replicated effect is a dendritic atrophy in apical dendrites from CA3 pyramidal neurons. This reduced dendritic branching has been associated with (i) a reduction in synaptic density of excitatory glutamatergic synapses; (ii) a shrinkage of the volume of the complex dendritic spines termed dendritic excrescences, that are located on the proximal apical dendrite and soma of CA3 pyramidal cells and which serve as postsynaptic targets for the mossy fiber synaptic inputs; and (iii) a rearrangement of synaptic vesicles and mitochondria in the afferent mossy fiber terminals. On its turn, evidence for synaptic remodeling—in terms of changes in synaptic features—has also been reported for the hippocampal CA1 region.

Prefrontal Cortex.

The prefrontal cortex (PFC), and more particularly its medial part (mPFC), plays key roles in higher cognitive processes (including executive function, working memory, attention), as well as in the integration of cognitive and emotionally relevant information. It should be noted that the mPFC contains high levels of glucocorticoid receptors and is involved in the regulation of stress-induced hypothalamic-pituitary-adrenal (HPA) activity. As noted above, clinical evidence highlights the mPFC as an area that experiences marked alterations in a wide variety of neuropsychiatric disorders, including depression.

There is substantial evidence from rodent studies for stress-induced dendritic shrinkage in the PFC. In particular, major neuronal remodeling was described to occur in layer II/III of the mPFC as a consequence of repeated exposure to chronic stress or repeated glucocorticoid treatment. The major described changes in this area are (i) a dendritic atrophy, including both decrease of total length and number of apical dendrites from pyramidal neurons; and (ii) a decrease in apical dendritic spine density (approximately one-third of all axospinous synapses on apical dendrites of pyramidal neurons are lost).

Antidepressant Effects.

Treatment with the atypical (modified tricyclic) antidepressant tianeptine was shown to reverse dendritic atrophy induced by chronic stress in CA3 pyramidal neurons in rats. Moreover, antidepressants were also reported to facilitate axonal and dendritic sprouting. These findings suggest that antidepressants can have a major impact on neuronal remodeling, providing the basis for relevant circuits to be reorganized in the course of recovery from depression.

Early-Life Stress

An aspect of the invention is a method for treating mood effects of early-life stress. The method includes the step of administering to a subject in need thereof a therapeutically effective amount of urolithin or a precursor thereof, to treat the effects of early-life stress on mood, depression, anxiety, and risk-taking behavior.

Early-life stress has been reported to have a significant detrimental effect on cognitive performance, including psychological parameters such as increased rates of or susceptibility to depression, anxiety, and abnormal risk-taking behavior. Heim C, Nemeroff C B. (2001) *Biol Psychiatry* 49:1023-1039. Increased rates of attention-deficit/hyperactivity disorder (ADHD), post-traumatic stress disorder (PTSD), and major depression have been reported in individuals having experienced early-life stress. Famularo R et al. (1992) *J Am Acad Child Adolesc Psychiatry* 31:863-867; Pelcovitz D et al. (1994) *J Am Acad Child Adolesc Psychiatry* 33:305-312. Early-life stress is thought to have an impact on the hypothalamic-pituitary-adrenal (HPA) axis. Ladd C O et al. (2000) *Prog Brain Res* 122:81-103. The key effector thought to control the responsiveness of the HPA axis to stress is the central corticotrophin releasing factors (CRF).

CRF is a 41 amino acid peptide which is distributed throughout the CNS. This includes the cell bodies of the medial parvocellular region of the hypothalamic paraventricular nucleus (PVN), a central component of the HPA axis. Upon stress, CRF is released from the median eminence nerve terminals into the hypothalamo-hypophysial portal circulation and transported to the anterior pituitary where it binds to CRF receptors (CRF1 and CRF2). CRF binding to the CRF1 receptor produces effects that are reminiscent of stress, depression, and anxiety. CRF binding to CRF2 receptor stimulates the production and release of adrenocorticotropic hormone (ACTH), which in turn stimulates the production of glucocorticoids involved in the stress response.

In models of early-life stress caused by maternal separation, a consistent long-term elevated level of CRF mRNA is observed. Plotsky P M et al. (2005) Neuropsychopharmacology 30:2192-2204. Such increases in CRF have been shown to have effects at the level of amygdala in increasing anxiety response. It is thought that a persistent sensitization of the CRF neurocircuits is responsible for the abnormally elevated anxiety, depression, and risk-taking behavior observed in mice exposed to early-life stress.

Current Strategies Employing Antidepressants to Improve Psychological Disorders Due to Early-Life Stress A number of studies have shown that antidepressants decrease CRF activity in the HPA axis in rodents and primates, including humans. Banki C M et al. (1992) *J Affect Disord* 25:39-45; Brady L S et al. (1992) *Brain Res* 572: 117-125; Brady L S et al. (1991) *J Clin Invest* 87:831-837; De Bellis M D et al. (1993)*Am J Psychiatry* 150:656-657; Veith R C et al. (1993) *Psychiatry Res* 46:1-8. Several classes of antidepressant drugs appear to produce a decrease in the activity of one or more CRF neural systems. These include selective 5-HT reuptake inhibitors (SSRI), which have been shown to be effective in the treatment of several psychiatric disorders that have been associated with early-life stress (e.g., depression and PTSD). Hidalgo R B et al. (2000) *J Psychopharmacol* 14:70-76. Notably, in a randomized placebo-controlled trial, subjects having undergone early-life stress and suffering from PTSD were responsive to fluoxetine. van der Kolk B A et al. (1994) *J Clin Psychiatry* 55:517-522. Furthermore, SSRIs, including fluoxetine and paroxetine, show significant efficacy versus placebo in the treatment of early-onset depression in children and adolescents. Martin A et al. (2000) *Child Adolesc Psychiatr Clin N Am* 9:135-157. Tricyclic antidepressants have also been found to reverse increased HPA axis reactivity to stress in adult primates exposed to maternal deprivation. Suomi S J. (1991) *Ciba Found Symp* 156:171-183. It appears that several available drugs, including the SSRIs, may be beneficial in the treatment of children and adults exposed to early-life stress. Fisher P A et al. (2000) *J Am Acad Child Adolesc Psychiatry* 39:1356-1364.

Additional Indications

The invention will also find use in the treatment of any of a variety of additional diseases and conditions in which defective or diminished mitochondrial activity participates in the pathophysiology of the disease or condition, or in which increased mitochondrial function will yield a desired beneficial effect. As an example, the invention further includes methods and compounds that may be used to treat male infertility associated with diminished sperm motility. Nakada et al. (2006) *Proc Natl Acad Sci USA*. 103:15148-53. As another example, the invention further includes methods and compounds that may be used to treat macular degeneration and certain other age-related and inherited eye disorders. Khandhadia et al. (2010) *Expert Rev Mol Med.* 12: e34; Jarrett et al. (2010) *Ophthalmic Res.* 44:179-90. Another example is a method of treating hearing loss, including but not limited to age-related hearing loss. In each of these and other indications, the method involves administering to a subject in need of such treatment an effective amount of a urolithin or precursor thereof, as disclosed herein, to treat the indication.

Formulations and Clinical Use

A "subject" as used herein refers to a living vertebrate. In one embodiment, a subject is a mammal. In one embodiment, a subject is a human.

As used herein, the term "treat" as used in connection with a disease, disorder, or condition of a subject, means to reduce by a detectable amount at least one clinical or objective manifestation of the disease, disorder, or condition of a subject. In one embodiment, the term "treat" used in connection with a disease, disorder, or condition of a subject, means to cure the disease, disorder, or condition of a subject.

The urolithin or precursor thereof may be administered, alone or together with another agent, to a subject (e.g., mammal) in a variety of ways. For example, the urolithin or precursor thereof can be administered orally or parenterally. Parenterally includes, without limitation, intravenously, intramuscularly, intraperitoneally, subcutaneously, intra-articularly, intrasynovially, intraocularly, intrathecally, topically, or by inhalation. As such, the form of the urolithin or precursor thereof dose can be in a variety of forms, including natural foods, processed foods, natural juices, concentrates and extracts, injectable solutions, microcapsules, nano-capsules, liposomes, plasters, inhalation forms, nose sprays, nosedrops, eyedrops, sublingual tablets, and sustained-release preparations.

The compounds of this invention can be provided in isolated form. As used herein, the term "isolated" means substantially removed from other compounds or components with which the compound of interest may otherwise be found, for example, as found in nature. In one embodiment, a compound is isolated when it is essentially completely removed from other compounds or components with which the compound of interest may otherwise be found. In one embodiment, a compound is isolated when it is pure.

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, and intratracheal administration. The active agent may be systemic after administration or may be localized by the use of regional administration, intramural administration, or use of an implant that acts to retain the active dose at the site of implantation.

The compounds of the invention can also be formulated as food additives, food ingredients, functional foods, dietary supplements, medical foods, nutraceuticals, or food supplements.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier, wherein each dosage unit, for example, mL or L, contains a predetermined amount of the composition containing one or more compounds of the present invention.

Implants for sustained release formulations are well-known in the art. Implants are formulated as microspheres; slabs, etc., with biodegradable or non-biodegradable polymers. For example, polymers of lactic acid and/or glycolic acid form an erodible polymer that is well-tolerated by the host. The implant containing the inhibitory compounds may be placed in proximity to a site of interest, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to, be achieved, and the pharmacodynamics associated with each compound in the host The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

For clinical use, the urolithin or urolithin precursor is administered in a therapeutically effective amount. As used herein, an "effective amount" refers to an amount that is sufficient to realize a desired biological effect. As used herein, a "therapeutically effective amount" refers to an amount sufficient to realize, in a single dose or multiple doses, a desired therapeutic effect. A skilled artisan can determine therapeutically effective amounts based on in vitro, preclinical, or clinical studies, or any combination thereof.

Dosing will generally be daily to weekly. In one embodiment, dosing is at least weekly. For example, a subject may receive one dose once weekly, twice weekly, thrice weekly, or every other day. In one embodiment, dosing is at least daily. For example, a subject may receive one or more doses daily.

For clinical use, a urolithin will generally be administered in an amount ranging from about to 0.2-150 milligram (mg) of urolithin per kilogram (kg) of body weight of the subject. In one embodiment, the urolithin or precursor thereof is administered in a dose equal or equivalent to 2-120 mg of urolithin per kg body weight of the subject. In one embodiment, the urolithin or precursor thereof is administered in a dose equal or equivalent to 4-90 mg of urolithin per kg body weight of the subject. In one embodiment, the urolithin or precursor thereof is administered in a dose equal or equivalent to 8-30 mg of urolithin per kg body weight of the subject. Where a precursor of urolithin is to be administered rather than a urolithin, it is administered in an amount that is equivalent to the above-stated amounts of urolithin.

Any given dose may be given as a single dose or as divided doses.

In one embodiment, the urolithin or precursor thereof is administered in a dose sufficient to achieve a peak serum level of at least 0.001 micromolar ($\mu$M). In one embodiment, the urolithin or precursor thereof is administered in a dose sufficient to achieve a peak serum level of at least 0.01 $\mu$M. In one embodiment, the urolithin or precursor thereof is administered in a dose sufficient to achieve a peak serum level of at least 0.1 $\mu$M. In one embodiment, the urolithin or precursor thereof is administered in a dose sufficient to achieve a peak serum level of at least 1 $\mu$M. In one embodiment, the urolithin or precursor thereof is administered in a dose sufficient to achieve a peak serum level of at least 5 $\mu$M. In one embodiment, the urolithin or precursor thereof is administered in a dose sufficient to achieve a peak serum level of at least 10 $\mu$M.

In one embodiment, the urolithin or precursor thereof is administered in a dose sufficient to achieve a sustained serum level of at least 0.001 micromolar ($\mu$M). In one embodiment, the urolithin or precursor thereof is administered in a dose sufficient to achieve a sustained serum level of at least 0.01 $\mu$M. In one embodiment, the urolithin or precursor thereof is administered in a dose sufficient to achieve a sustained serum level of at least 0.1 $\mu$M. In one embodiment, the urolithin or precursor thereof is administered in a dose sufficient to achieve a sustained serum level of at least 1 $\mu$M. In one embodiment, the urolithin or precursor thereof is administered in a dose sufficient to achieve a sustained serum level of at least 5 $\mu$M. In one embodiment, the urolithin or precursor thereof is administered in a dose sufficient to achieve a sustained serum level of at least 10 $\mu$M. The sustained serum level can be measured using any suitable method, for example, high pressure liquid chromatography (HPLC) or HPLC-MS.

In one embodiment, the urolithin or precursor thereof is administered as pomegranate juice in the amount of 25 mL to 5 L, or an equivalent dose of ellagitannins, ellagic acid, urolithins, or any combination thereof. Table 4 shows the consumption of different pomegranate compounds for different levels of pomegranate juice. The range covers differences in compound concentration among different varieties of pomegranate. For the calculations of ellagic acid equivalents, it was assumed that the metabolism of each mole of punicalagin resulted in the release of 1 mole of ellagic acid, and that this conversion happened with 100% efficiency. Levels of urolithin were determined by assuming that all the ellagic acid present, including that derived from punicalagin, converted to urolithin with 100% efficiency. Not taken into consideration were other sources of ellagic acid besides punicalagin and ellagic acid.

TABLE 4

| Juice Equivalent (mL) | Punicalagin (mg/d) | Ellagic Acid (mg/d) | Ellagic Acid Equivalents (1:1) (mg/d) | Total Urolithin (1:1) (mg/d) |
|---|---|---|---|---|
| 25 | 10-65 | 3-30 | 20-35 | 15-25 |
| 50 | 20-130 | 6-60 | 40-70 | 30-50 |
| 75 | 30-195 | 9-90 | 60-105 | 45-75 |
| 100 | 40-260 | 12-120 | 80-140 | 60-100 |
| 150 | 60-390 | 18-180 | 120-210 | 90-150 |
| 200 | 80-510 | 24-240 | 160-280 | 120-200 |
| 250 | 100-650 | 30-300 | 200-350 | 150-250 |
| 500 | 200-1300 | 60-600 | 400-700 | 300-500 |
| 750 | 300-1950 | 90-900 | 600-1050 | 450-750 |
| 1000 | 400-1600 | 120-1200 | 800-1400 | 600-1000 |
| 2000 | 800-3200 | 240-2400 | 1600-2800 | 1200-2000 |
| 3000 | 1200-4800 | 360-3600 | 2400-4200 | 1800-3000 |
| 4000 | 1600-6400 | 480-4800 | 3200-5600 | 2400-4000 |
| 5000 | 2000-13000 | 600-6000 | 4000-7000 | 3000-5000 |

In one embodiment, the subject is not taking a urolithin or precursor thereof for any purpose other than for the treatment of a condition in accordance with the methods of the invention. In one embodiment, the subject is not taking a urolithin or precursor thereof for the treatment of atherosclerosis, thrombosis, cancer, unwanted angiogenesis, infection, or inflammation.

EXAMPLES

The invention now being generally described, it will be more readily understood by reference to the following, which is included merely for purposes of illustration of certain aspects and embodiments of the present invention, and is not intended to limit the invention.

Example 1

Preparation of Functional Extracts from Pomegranate Compounds

The pomegranate extracts described in this application containing specific molecules were prepared using an extraction procedure based on adsorption of polyphenols in a standard polymer adsorption-based column as described. For the preparation of the extracts 31008 and 1108 derived from pomegranate juice, pomegranates were juiced using a standard juicing and manufacturing process and adsorbed onto a polymeric chromatographic resin as pure juice. The resin Amberlite XAD-16 (Rohm & Haas) was packed into semi-preparative columns and loaded with the extracted juice. The column was washed with water to remove the sugars until completion (Brix levels were below 0.1%). The remaining polyphenols were eluted with 100% ethanol. The remaining ethanol was evaporated under vacuum to produce a concentrated extract containing 4.5 g of total polyphenol per liter as determined using the Folin assay for total polyphenol content. Extract 1011 was prepared in a similar manner as extract 31008 and 1108, but the liquid extract was then spray dried utilizing a spray dryer to produce a final powder extract. Utilizing HPLC-MS for the identification of compounds, extract 31008, 1108, and 1011 were found to contain the molecules punicalagin, punicalin, tellimagrandin, and pedunculagin.

The extract 71109 derived from the pomegranate husk was prepared by manually separating the husk from the pomegranate arils pulp, followed by pressing with a manual fruit press. To extract the maximal amount of polyphenols, the cake/pomace of pressed pomegranate parts were soaked in water consecutively for several periods of time (5 minutes) in order to increase extraction efficiency. The extracted pomegranate solution was clarified by centrifugation before being adsorbed onto the polymeric chromatographic Amberlite XAD-16 resin (Rohm & Haas), packed in semi-preparative columns, and loaded with the water extracted from pomegranate husk. The column was washed with water to remove the sugars until completion (Brix levels were below 0.1%). The polyphenols were eluted with 100% ethanol. The remaining ethanol was evaporated under vacuum to produce a concentrated extract containing 17.1 g of total polyphenol per liter as determined using the Folin assay for total polyphenol content. This technique is a modification of methods known in the art as described by several published methods for purification of polyphenols from various plants and berries. Tuck, K. L. and P. J. Hayball (2002) "Major phenolic compounds in olive oil: metabolism and health effects." *J Nutr Biochem* 13(11):636-644; and Schieber, A., P. Hilt, et al. (2003) "A new process for the combined recovery of pectin and phenolic compounds from apple pomace." *Innovative Food Sci. Emerging Technol.* 4:99-107.

For the preparation of Extract 61109, an aqueous extract of the pomegranate was fractionated utilizing centrifugal partition chromatography. The isolation fractions were lyophylized to produce extract 61109, highly enriched in punicalagin (>90%).

Purification of Punicalagin
Preparation of Extract

Extract from pomegranate was dissolved in 16 mL of the organic/aqueous phase mixture (1:1) and filtered on a Teflon filter (0.45 µm).

Separation of Punicalagin from Extract Using Centrifugal Partition Chromatography Separation of punicalagin from pomegranate extract was achieved by utilizing Centrifugal Partition Chromatography CPC. The CPC apparatus was a FCPC® 1000 apparatus provided by Kromaton Technologies (Angers, France) that is fitted with a rotor of 1000 mL capacity. The solvents were pumped by a 4-way binary high-pressure gradient pump. The samples were introduced into the CPC column via a high pressure injection valve (Rheodyne) equipped with a 20 mL sample loop. The effluent was monitored with a diode array detection (DAD) detector equipped with a preparative flow cell. Fractions were collected by a fraction collector. The separation steps were conducted at room temperature.

To accomplish the extraction, the stationary phase was first introduced into the column in the ascending mode without rotating, and mobile phase was then pumped through the stationary phase until an equilibrium stage was reached. Then, the rotation speed was increased from 0 to 1000 rpm and the mobile phase was pumped into the column at a flow-rate of 20 mL/min. After injection of 10 g of pomegranate extract, fractions of 20 mL were collected every minute. The content of the outgoing organic phase was monitored by online UV absorbance measurement at X=260 nm.

An elution-extrusion procedure was used to recover all the compounds from the column: after a classical elution of 100 min, the mobile phase was replaced by the stationary phase used as mobile liquid, until all volume contained (1000 mL) was pushed out the column. A fraction containing punicalagins (mixture of A and B isomers) with 94-97% chromatographic purity was obtained between 51 and 63 minutes of elution, and a second fraction with a chromatographic purity of 85-88% was obtained between 64 and 79 min.

To determine the level of purification, the purified sample was examined using by HPLC-DAD at a detection wavelength of 260 nm. The sample was run over a Prosontil C18, 5 µm, 250×4 mm column. The solvents used were $H_2O$ mQ+9.1% TFA/Acetonitrile+0.1% TFA at a flow rate of 1 mL/min.

Example 2

In Vitro Screening Assays for Compounds Promoting Enhancement of the Expression of Mitochondrial Genes in a Prototypical Skeletal Muscle Cell Line (C2C12 Myotubes)

Skeletal muscles have a pivotal role in the regulation of metabolic homeostasis since they are involved in metabolic functions such as energy expenditure and maintenance of insulin sensitivity. These functions are tightly linked to mitochondrial activity, and impairment of mitochondrial function has a causal role in defective metabolic homeostasis and development of metabolic disorders such as type 2 diabetes, obesity, and dyslipidemia. Gene expression profile of genes involved in mitochondrial activity in differentiated C2C12 cells (myotubes) is an appropriate model to assess the impact of compounds on mitochondrial activity by evaluating numerous pathways which reflect mitochondrial activity, e.g., mitochondrial biogenesis, glycolysis, fatty acid β-oxidation, electron transport chain (ETC), mitochondrial dynamics.

To assess the effects of compounds on mitochondrial gene expression, C2C12 myoblasts were differentiated into myotubes by serum deprivation for 4 days (Cantó et al. (2009) *Nature.* 458:1056-60). Myotubes were incubated for 48 hr with ellagic acid or urolithin A at a final concentration of 1, 10 or 50 µM (all dissolved in DMSO, final concentration 0.1%). DMSO was used as a control (final concentration 0.1%). At the end of the treatment, cells were washed with phosphate buffered saline (PBS) and mRNA were immediately extracted according to manufacturer's instructions (Trizol Reagent, Invitrogen) by adding 1 mL of Trizol reagent. After extraction, cDNA were produced by reverse transcription according to manufacturer's instructions.

Assessment of the expression levels of genes (PGC-1α, Tfam, PFKFB3, CPT1b, MCAD, LCAD, Ndufa2, Cyt c, and Mfn2) which control the mitochondrial function was performed by real time quantitative PCR (Watanabe et al. (2004) *J Clin Invest.* 113:1408-18) by using the following set of primers (Fwd: forward primer; Rev: reverse primer):

```
PGC-1α:
(Fwd)    AAGTGTGGAACTCTCTGGAACTG        (SEQ ID NO: 1)

(Rev)    GGGTTATCTTGGTTGGCTTTATG        (SEQ ID NO: 2)

Tfam:
(Fwd)    AAGTGTTTTTCCAGCATGGG           (SEQ ID NO: 3)

(Rev)    GGCTGCAATTTTCCTAACCA           (SEQ ID NO: 4)

PFKFB3:
(Fwd)    TCATGGAATAGAGCGCC              (SEQ ID NO: 5)

(Rev)    GTGTGCTCACCGATTCTACA           (SEQ ID NO: 6)

CPT1b:
(Fwd)    CCCATGTGCTCCTACCAGAT           (SEQ ID NO: 7)

(Rev)    CCTTGAAGAAGCGACCTTTG           (SEQ ID NO: 8)

MCAD:
(Fwd)    GATCGCAATGGGTGCTTTTGATAGAA     (SEQ ID NO: 9)

(Rev)    AGCTGATTGGCAATGTCTCCAGCAAA     (SEQ ID NO: 10)

LCAD:
(Fwd)    GTAGCTTATGAATGTGTGCAACTC       (SEQ ID NO: 11)

(Rev)    GTCTTGCGATCAGCTCTTTCATTA       (SEQ ID NO: 12)

Ndufa2:
(Fwd)    GCACACATTTCCCCACACTG           (SEQ ID NO: 13)

(Rev)    CCCAACCTGCCCATTCTGAT           (SEQ ID NO: 14)

Cyt c:
(Fwd)    TCCATCAGGGTATCCTCTCC           (SEQ ID NO: 15)

(Rev)    GGAGGCAAGCATAAGACTGG           (SEQ ID NO: 16)

Mfn2:
(Fwd)    ACGTCAAAGGGTACCTGTCCA          (SEQ ID NO: 17)

(Rev)    CAATCCCAGATGGCAGAACTT          (SEQ ID NO: 18)
```

PGC-1α (PPARγ-coregulator 1α) and Tfam (mitochondrial transcription factor A) are master regulators of the mitochondrial function, namely of mitochondrial biogenesis and mitochondrial phosphorylative oxidation (mOXPHOS). An increase in their expression levels reveals an overall enhancement of mitochondrial activity. The assessment of other target genes involved in key functions of the mitochondria allows identifying the enhanced pathways. PFKFB3 (6-phosphofructo-2-kinase/fructose-2,6-biphosphatase 3) is a key enzyme of glycolysis, i.e., the use of glucose to produce energy. In aerobic conditions (i.e., when there are supplies of oxygen), pyruvate produced from glucose via glycolysis is used by the mitochondria to produce energy (ATP) through the Krebs cycle. CPT1b (carnitine O-palmitoyltransferase 1b), MCAD (medium chain acyl CoA dehydrogenase), and LCAD (long chain acyl CoA dehydrogenase) play a pivotal role in mitochondrial fatty acid uptake and β-oxidation, two critical steps for energy production from fatty acids. Ndufa2 (NADH dehydrogenase [ubiquinone] 1 alpha subcomplex subunit 2) and Cyt c (cytochrome c) are subunits of complex I and IV of the mitochondrial electron transport chain, respectively. These proteins have an essential role in mitochondrial respiratory chain and energy production from reduced equivalent produced by the Krebs cycle. Mfn2 (Mitofusin 2) is involved in mitochondrial dynamics and fusion process. Its expression is increased in the context of increased mitochondrial remodeling and/or mitochondrial biogenesis (increased number of mitochondria per cell).

Figure 3:
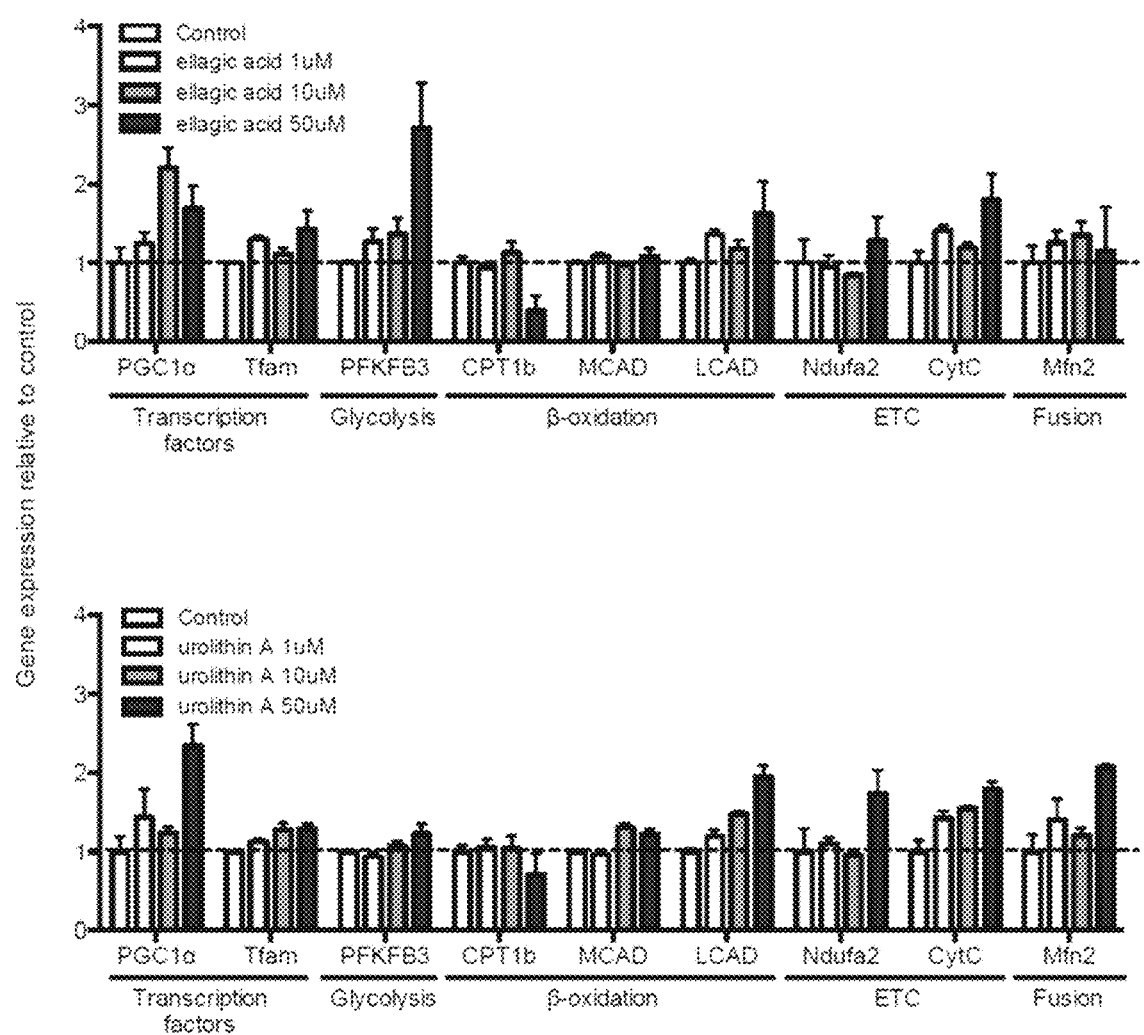
FIG. 3 is a pair of bar graphs depicting mitochondrial gene expression levels in response to the indicated concentrations of ellagic acid (upper panel) and urolithin A (lower panel).

The data depicted in FIG. 3 clearly indicate that ellagic acid and urolithin A increase mitochondrial activity in a dose-dependent manner by modulating the expression of numerous genes involved in several pathways of mitochondrial metabolism.

Example 3

In Vitro Screening Assay for Compounds Promoting Enhancement of Mitochondrial Activity in a Prototypical Skeletal Muscle Cell Line (C2C12 Myotubes)

Citrate synthase is the initial enzyme of the tricarboxylic acid (TCA) cycle and the rate limiting step to enter the TCA cycle. The TCA cycle will produce NADH2 and FADH2, which are then used to fuel the electron transport chain which will generate a proton (energy) gradient, which will be used in the generation of ATP. As such, citrate synthase is an exclusive marker of the mitochondrial number and of the mitochondrial activity. By measuring the effects of compounds or formulations on citrate synthase enzyme activity, it is possible to assess the ability of the compounds to stimulate mitochondria activity (i.e., OXPHOS and ATP production).

The enzyme citrate synthase catalyzes the reaction between acetyl coenzyme A (acetyl CoA) and oxaloacetic acid to form citric acid. The acetyl CoA contributes 2 carbons to the 4 carbons of oxaloacetate, resulting in citrate with 6 carbons. The hydrolysis of the thioester of acetyl CoA results in the formation of CoA with a thiol group (CoA-SH). The activity of citrate synthase is measured via the reaction between the thiol of CoA-SH with the DTNB in the mixture to form 5-thio-2-nitrobenzoic acid (TNB). This yellow product (TNB) is observed spectrophotometrically by measuring absorbance at 412 nm (Citrate Synthase Assay Kit, Cat Number CS0720, Sigma Aldrich).

C2C12 myoblasts were differentiated into myotubes by serum deprivation for 4 days (Canto et al. (2009) Nature. 458:1056-60). Myotubes were incubated for 48 hr with punicalagin at a final concentration of 1 or 10 μM or with ellagic acid or urolithin at a final concentration of 1, 10 or 50 μM (all dissolved in DMSO, final concentration 0.1%). DMSO was used as a control (final concentration 0.1%). At the end of the treatment, cells were washed 3 times with PBS and assayed for citrate synthase activity according to manufacturer's instructions (Citrate Synthase Assay Kit, Cat Number CS0720, Sigma Aldrich).

Figure 4:
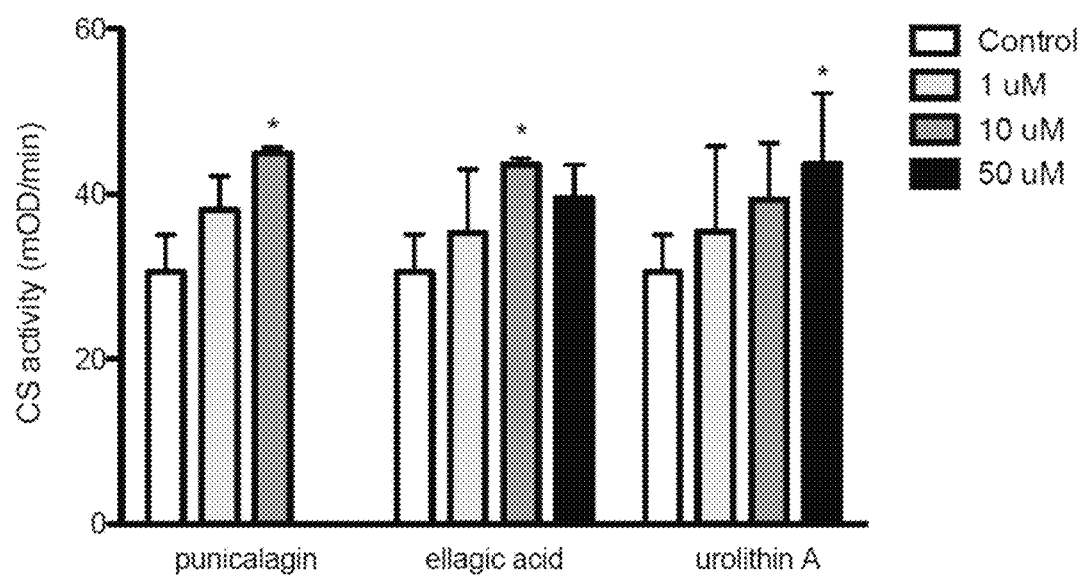
FIG. 4 is a bar graph depicting citrate synthase (CS) activity measured in vitro in the presence of the indicated concentrations of punicalagin, ellagic acid, urolithin A, or negative control.

As depicted in FIG. 4, punicalagin, ellagic acid, and urolithin increase citrate synthase activity in a dose-dependent manner, illustrating an overall increase in mitochondrial activity and/or mitochondrial density (number of mitochondria per cells). These results confirm the results obtained by gene expression profile of mitochondrial genes (Example 1) showing an enhancement of mitochondrial activity and mitochondrial biogenesis in treated differentiated C2C12.

Statistics: 1-way ANOVA*$p<0.05$.

Example 4

In Vitro Screening Assay for Compounds Promoting AMP-Activated Protein Kinase (AMPK) Activity in a Prototypical Skeletal Muscle Cell Line (C2C12 Myotubes)

AMPK acts as a metabolic master switch regulating several intracellular systems including the cellular uptake of glucose, the β-oxidation of fatty acids, and the biogenesis of glucose transporter 4 (GLUT4) and mitochondria. The energy-sensing capability of AMPK can be attributed to its ability to detect and react to fluctuations in the AMP:ATP ratio that take place during rest and exercise (muscle stimulation). As an example, during a bout of exercise, AMPK activity increases (phosphorylation of AMPK, P-AMPK) while the muscle cell experiences metabolic stress brought about by an extreme cellular demand for ATP. Upon activation (AMPK phosphorylation, P-AMPK), AMPK increases cellular energy levels by inhibiting anabolic energy-consuming pathways (fatty acid synthesis, protein synthesis, etc.) and stimulating energy-producing, catabolic pathways (fatty acid oxidation, glucose transport, etc.). Consequently, AMPK activation leads to an enhancement of mitochondrial function, including increased OXPHOS and mitochondrial biogenesis.

C2C12 myoblasts were differentiated to myotubes by serum deprivation for 4 days (Canto et al. (2009) *Nature.* 458:1056-60). Myotubes were incubated for 1 hr with resveratrol (RSV), which served as a positive control, or ellagic acid (EA) or urolithin A (UL) at a final concentration of 50 μM (all dissolved in DMSO, final concentration 0.1%). DMSO was used as a control (final concentration of DMSO: 0.1%). At the end of the treatment, cells were washed 3 times with PBS, and AMP-activated protein kinase (AMPK) was assessed by Western blot. Following compound treatment, C2C12 cells were lysed in buffer containing phosphatase inhibitors, and protein concentration was determined using a standard Bradford assay. The equivalent of 25 μg of protein was used for separation on a 10% SDS-PAGE gel and subsequently transferred by standard Western blotting procedures. Antibodies directed to AMPK (Cell Signaling) and phosphorylated AMPK (P-AMPK, Cell Signaling) were used for detection.

As depicted in FIG. 5A, Western blot analysis for the phosphorylated, and thus the activated form of AMPK—i.e., P-AMPK, indicated that the levels of phosphorylation of AMPK (P-AMPK) and hence activation of the AMP-activated protein kinase (AMPK) were indeed increased in cells treated with ellagic acid or urolithin relative to control treated cells. This data indicates that ellagic acid and urolithin A are both AMPK activators. This further supports the observations that ellagic acid and urolithins induce an increase in mitochondria function.

Example 5

Screening Assay for Compounds Promoting Neurite Outgrowth in PC-12 Cells

Neurite outgrowth and the number of mean processes per cell in neuronal culture have been shown to correspond to neuronal function. Chronic stress has been shown to result in reductions both of dendritic length and branch number, an effect which was reversed upon the removal of stress. Furthermore, it has been shown that this reversibility became inhibited with aging (Bloss, Janssen et al. 2010). There is also further evidence that learning and novel sensory experiences are associated with increases in spine formation and elimination of protracted processes. Hence synaptic structural plasticity plays an important role in learning and memory (Yang, Pan et al. 2009). Indeed, the level of neurite outgrowth and number of processes induced by compounds such as nerve growth factor (NGF) correlates strongly with their neuroprotective abilities. With aging this synaptic plasticity becomes compromised and there is an increased loss of spines and a decreased density of synapses (Dumitriu, Hao et al. 2010). Neurodegenerative diseases also have an effect on neurite outgrowth. A-beta (Aβ) peptide, which plays an important role in Alzheimer's disease, inhibited neurite outgrowth in mouse neuroblastoma cells. Therefore, by assaying the effects on neurite outgrowth in vitro, compounds and formulations with neuroprotective effects on neurons under chronic stress, neurons undergoing aging, and neurons present in neurodegenerative diseases can be identified.

The in vitro effects on neurite outgrowth of the different ellagitannins and their metabolites punicalagin (PA), punicalin (PB), tellimagrandin (TL), ellagic acid (EA), and urolithin (UA), were tested on cells of a noradrenergic rat pheochromocytoma cell line (PC-12 cells), which have been shown to differentiate in response to nerve growth factor (NGF) (Greene and Tischler 1976). Neuritic outgrowth in these differentiated PC-12 cells has been shown to be strongly promoted by dibutyryl cyclic AMP (dbcAMP) (Gunning, Landreth et al. 1981), and this compound was utilized as a positive control. As a negative control, the specific Janus N-terminal kinase (JNK) inhibitor SP600125, which has been shown to decrease different parameters of neurite outgrowth, was utilized (Xiao, Pradhan et al. 2006). The ellagitannins and their metabolites tested in the assays were synthesized or purchased from suppliers which included Funakoshi, Sigma, and Chemos. Stock solutions were aliquoted and stored at −20° C.

PC-12 cells (ATCC CRL-1721) were cultured at 37° C., 5% $CO_2$ in poly L-lysine-coated culture flasks in complete culture medium (RPMI 1640+10% heat-inactivated horse serum+5% fetal bovine serum).

Cell differentiation was performed in culture flasks 24 h after plating, in complete medium supplemented with 100 ng/mL NGF (2.5 S NGF, Invitrogen). The NGF-supplemented medium was renewed every third day, and differentiation was induced over an 8-day period.

All compounds to be tested were prepared just before the experiment as a 50 mM stock solution in dimethylsulfoxide (DMSO). The final DMSO concentration was 0.1% in the medium of all experimental groups.

For neurite outgrowth measurements, differentiated cells were washed with phosphate-buffered saline (PBS), collected after detachment and replated at a density of 5,000 cells/well (biocoat imaging 96 well plate) in complete medium supplemented with 100 ng/mL NGF, with or without 10 μM SP600125 (negative control), 1 mM dbcAMP (positive control), or tested compound at $5\times10^{-7}$ M. In the undifferentiated control group, no NGF was added after replating.

After 72 h in culture, PC-12 cells were washed with PBS and fixed in 1% paraformaldehyde solution for 20 minutes. After 3 washes with PBS, immunofluorescence labeling was performed with Texas Red Maleimide probe, which reacts with thiol groups of cysteine residues of proteins, permitting the visualization of the entire cell morphology, including neurites.

Immunofluorescence analysis was performed in automated confocal microscopy. Images were acquired with a BD pathway 855 system, under X20 objective with 8×8 field montage. Neurite outgrowth was then measured from acquired images with the neurite module of Metamorph® software. Total and mean outgrowth, total and mean number of processes per cell, and total and percentage of cells with extensive outgrowth (defined as outgrowth longer than 20 μm) were analyzed.

All compounds, except PA and PB, increased the number of PC-12 cells in the wells by >30%, as shown in FIG. 6, indicating a trophic effect for these compound at a concentration of 0.5 µM (p<0.001 for UA, EA, and TL versus differentiated control (ctrl)).

Promotion of Neurite Outgrowth

As shown in FIG. 7 and FIG. 8, all compounds tested (PA, PB, TL, EA and UA) were able to induce robust neurite outgrowth from differentiated PC-12 cells. The mean outgrowth (FIG. 7) showed an increase of >30% over differentiated control for all the compounds tested. The percent of cells showing significant outgrowth (FIG. 8) was significantly greater than that observed for differentiated cells for all compounds tested (p<0.05 for UA and PB (26% increase), p<0.01 for PA (>26% increase), p<0.001 for EA and TL, (>37% increase)).

Promotion of Process Formation and Branching

The compounds PA, PB, UA, EA, and TL, all induced an increase in the number of processes when applied to differentiated PC-12 cells. Compounds (UA, p<0.05 (15.7% increase); PA, p<0.01 (26.3% increase); EA and TL, p<0.001 (>31% increase) were either as effective as or more effective than dbcAMP, the positive control, in promoting process formation (FIG. 9).

Neurite branching was significantly higher than that observed in differentiated control, with most compounds inducing a two-fold increase in branching.

Example 6

Screening Assay for Compounds Promoting Neurite Outgrowth in Primary Dopaminergic TH-Positive Neurons Primary neurons due to their untransformed state, serve as a good in vitro model for the effects of compounds on markers of neuronal plasticity and differentiation, such as neuronal outgrowth, and formation of dendrites and processes. The effects of different ellagitannin metabolites punicalagin (PA), urolithin (UA), ellagic acid (EA), and tellimagrandin (TL) on this process were examined. The compounds tested in the assays were purchased from suppliers which included Funakoshi and Sigma, or were chemically synthesized. Stock solutions were aliquoted and stored at −20° C.

Primary mesencephalic cultures were prepared from rat E14 embryos. Ventral mesencephalon was carefully dissected and dissociated. Cells were then plated in DMEM F12 medium containing 10% heat inactivated horse serum at the density of 100,000 cells/well (96-well plate), with or without the JNK-specific inhibitor SP600125 (10 µM) (which served as a negative control) or dbcAMP (1 mM) (which served as a positive control), or the compounds tested each at the doses of 0.1 µM.

72 h after plating, the effects on the neurite outgrowth of dopaminergic tyrosine hydroxylase (TH)-positive neurons were measured from images acquired by automated confocal microscopy (X4 objective, montage 4×4) and covering the entire well surface, and quantified using the Neurite outgrowth module of Metamorph® software. Several representative parameters of neurite outgrowth were thus generated: total and mean outgrowth, total and mean number of processes per cell, and total and percentage of cells with extensive outgrowth (defined as outgrowth longer than 20 µm) were analyzed. All experiments were performed in quadruplicate.

Promotion of Neurite Outgrowth

As shown in FIGS. 10-16, compounds selected in the above PC-12 screening assay were also able to induce neurite outgrowth in primary mesencephalic neurons at a concentration of 0.1 µM. Most compounds were as effective as dbcAMP in promoting outgrowth per cell (>25% increase in outgrowth) as measured by the mean outgrowth per cell shown in FIG. 10 (p<0.001 for UA, GA, EA, TL vs control). All compounds tested performed as well or better than dbcAMP (FIG. 11).

Increase in Neurite Processes and Branching

All the compounds tested showed significant increases in the mean processes per cell (>10%) (FIG. 12), as well as in the maximum process length (>10%) (FIG. 13).

Primary cells showed an increase in branching in the presence of the positive control (dbcAMP). However, the JNK inhibitor SP600125 did not inhibit primary cell branching, as in PC12 cells, but was capable of promoting branching albeit not to the same level as dbcAMP (60% vs 86% increase seen for dbcAMP). The compounds UA, EA, and TL were able to promote branching to the same levels as dbcAMP (>111% increase in branching, FIG. 14).

Increases in Dendrites Per Cell and Dendrite Length

Dendrite number was increased significantly for UA, EA, and TL, at levels above that of dbcAMP, with all compounds showing an increase >18% (FIG. 15).

Ellagic acid, urolithin A, and tellimagrandin all produced increases in dendritic length >26%, higher than that observed for dbcAMP (FIG. 16).

Example 7

Pomegranate Extract, Punicalagin, Ellagic Acid, and Urolithin A Reduce Weight Gain and Fat Mass in Mice Fed a High Fat Diet Male C57BL6/J mice were purchased from Charles River Laboratory (L'Arbresle, France) at the age of 7 weeks and acclimatized to the animal facility for 2 weeks before initiation of experiments. Mice were housed in groups of 5 in standard housing conditions, with a 12 hr light-dark cycle and free access to food and water. Beginning at 9 weeks of age, mice were fed a high-fat diet (HFD) (60% kcal from fat; D12492; Research Diets Inc., New Brunswick, N.J., USA) for fourteen weeks. Body weight was monitored weekly.

Mice in different treatment groups were administered (i) urolithin A mixed with food (food admix) to reach a dosing of 55 mg/kg body weight/day (mkd); (ii) ellagic acid mixed with food (food admix) to reach a dosing of 75 mkd; (iii) punicalagin (gavage) to reach a dosing of 90 mkd; or (iv) pomegranate extract (PE) (gavage) to reach a dosing of 140 mkd of total polyphenols. A typical pomegranate extract used in these experiments had the following composition: polyphenols, 140 mkd; punicalagin, 13.1 mkd; and ellagic acid, 13.2 mkd. For animals treated by gavage, gavage was performed daily (7 days/week) between 8:00 and 10:00 a.m.; compounds were mixed with saline solution (0.9% NaCl) and provided at a final volume of 5 mL/kg of body weight. Mice in high-fat control groups were fed with the same diet as the experimental animals. Mice in corresponding different control groups were administered either high-fat diet alone or high-fat diet plus daily gavage with vehicle (saline). Another control group of mice were fed standard chow diet alone.

Body composition was monitored by EchoMRI (Echo Medical Systems, Houston, Tex., USA) 5 weeks after the initiation of the treatment for high-fat diet fed mice and 2 weeks after the initiation of the treatment for chow diet fed mice. Animals were placed individually into a plastic cylinder and then introduced into an EchoMRI system for about 2 min for body composition scanning (lean and fat mass).

Results are shown in FIGS. 17A-17C and 18A and 18B.

Mice fed with a high-fat diet (HFD) developed a severe obesity compared to control mice fed with a standard chow diet (CD) (FIG. 17A). Body weight gain in untreated high-fat fed mice was associated with an increase in the percentage of fat mass (FIG. 17B) and a decrease in the percentage of muscle mass (lean mass) (FIG. 17C), both as measured by EchoMRI after 5 weeks of treatment. In mice fed a high-fat diet, treatment with urolithin A (administered by food admix) or with punicalagin or pomegranate extract (PE) (both administered by gavage) prevented the onset of obesity with a strong reduction of body weight gain in treated HFD-fed mice compared to control HFD-fed mice (FIG. 17A). Along with this, fat mass was significantly reduced in HFD-fed mice treated with urolithin A, punicalagin, or PE compared to untreated HFD fed mice (FIG. 17B).

Mice fed a standard-chow diet and treated with either ellagic acid or urolithin A also saw a reduction in fat mass with a concomitant increase in muscle (lean mass), illustrating that these treatments favor the management of weight and a lean or muscular physique (FIG. 18B).

Example 8

Pomegranate Extract, Punicalagin, Ellagic Acid, and Urolithin A Increase Muscle Mass in Normal and Obese Mice Male C57BL6/J mice were grouped and treated as described in Example 7.

In both standard chow diet-fed mice and HFD-fed mice, treatment with PE, punicalagin, ellagic acid or urolithin A resulted in a statistically significant increase in the percentage of lean mass. Mice fed a high-fat diet and treated with urolithin A, punicalagin, or PE saw a reduction in fat mass with a concomitant increase in muscle (lean mass) (FIGS. 17B and 17C). Mice fed a chow diet and treated with either ellagic acid or urolithin A also saw a reduction in fat mass with a concomitant increase in muscle (lean mass), illustrating that these treatments favor the management of weight and a lean or muscular physique (FIGS. 18A and 18B). Since lean mass is predominantly represented by muscle mass, these results illustrate how treatments with either PE, punicalagin, ellagic acid or urolithin A result in an increase in the proportion of muscle mass in both normal and obese mice with respect to total body mass. This effect was observed after as little as two weeks of treatment.

Example 9

Pomegranate Extract, Punicalagin, Ellagic Acid, and Urolithin A Increase Energy Expenditure in Normal and Obese Mice Male C57BL6/J mice were grouped and treated as described in Example 7. In addition, however, basal energy expenditure of mice was measured by indirect calorimetry (oxygen consumption, carbon dioxide production, and respiratory exchange ratio), 8 weeks after the initiation of treatment for the HFD-fed mice and 2 weeks after the initiation of treatment for standard show diet-fed mice, using the Comprehensive Laboratory Animal Monitoring System (CLAMS; Columbus Instruments, Columbus, Ohio, USA). Animals were first acclimatized for 22 h to CLAMS cages (room temperature 22° C.±1° C.) starting between 11 to 12 am. Then measurement was performed for at least 20 h in the same condition. Measurement included an entire dark cycle. Parameters measured during CLAMS were the following: (i) Oxygen consumption ($VO_2$ in mL/kg/h): $VO_2$ is directly correlated to energy expenditure; (ii) Carbon dioxide production ($VCO_2$ in mL/kg/h); and (iii) Respiratory Exchange Ratio (RER): $VCO_2/VO_2$: RER is an indicator of the use of energy substrate. In a steady state, RER is equivalent to the Respiratory Quotient (RQ). Pure carbohydrate use gives RER=1, whereas pure fat burning yields an RER=0.7. A mixed diet gives a RER=0.85.

Results are shown in FIGS. 19A, 19B, 20A, and 20B.

Oxygen consumption is a physiological marker of mitochondrial activity and energy expenditure. Treatments with either PE, punicalagin, ellagic acid, or urolithin A significantly increased oxygen consumption in mice. Ellagic acid and urolithin A increased energy expenditure in standard chow-fed mice (FIGS. 19A and 19B). This effect was observed after as little as 2 weeks of treatment. Pomegranate extract (PE), punicalagin, and urolithin A treatment increased energy expenditure in HFD-fed mice (FIGS. 20A and 20B).

Example 10

Pomegranate Extract, Punicalagin, Ellagic Acid, and Urolithin A Increase Use of Fatty Acids as Energy Substrates in Normal and Obese Mice Male C57BL6/J mice were grouped and treated as described in Example 9.

As stated above, in addition to oxygen consumption, indirect calorimetry also monitors carbon dioxide production. The ratio between carbon dioxide production ($VCO_2$) and oxygen consumption ($VO_2$) is called Respiratory Exchange Ratio (RER). RER is an excellent indicator of the use of energy substrates. In a steady state, RER is equivalent to the Respiratory Quotient (RQ). A preferential use of carbohydrates as energy substrate gives a RER close to 1, whereas a use of fat as energy substrate (fat burning) yields a lower RER which is close to 0.7 when fatty acids are preferentially used.

As depicted in FIGS. 21A, 21B, 22A, and 22B, PE, punicalagin, ellagic acid, and urolithin A treatment significantly decreased RER in both chow diet and HFD-fed mice. This effect was dramatic in chow diet fed mice treated with ellagic acid and urolithin A (FIG. 21A and FIG. 21B). These results support the shifts in body composition observed following the consumption of PE, punicalagin, ellagic acid or urolithin A which favor a more muscular (lean) physique with reduced fat composition.

Example 11

Pomegranate Extract, Punicalagin, and Urolithin A Decrease Plasma Levels of Triglycerides and Free Fatty Acids in Obese Mice Male C57BL6/J mice were grouped and treated as described in Example 7. In addition, plasma biochemistry was performed 14 weeks after the initiation of the treatment using a standard automated clinical chemistry analyzer (Dimension Xpand, SIEMENS). Animals were fasted for 12 h (from 8 pm to 8 am) before blood collection. Approximately 500 µL of blood was collected from vena cava in anesthetized animals under isofluorane anesthesia. Blood was collected in heparinized tubes and immediately placed on wet ice. Plasma was prepared by centrifugation (1500×g, 15 min, 4° C.). Plasma samples were then transferred in clean 1.5 mL microtubes and stored at −80° C. until biochemical measurements were performed on a standard automated clinical chemistry analyzer (Dimension Xpand, SIEMENS) using corresponding kits.

Circulating levels of triglycerides and free fatty acids was measured by standard biochemistry in the blood of control and treated HFD-fed mice (FIG. 23A and FIG. 23B). PE, punicalagin and urolithin A treatment led to a statistically significant improvement of plasma levels of triglycerides and free fatty acids. These results indicate that PE, punicalagin, and urolithin A are effective in treating dyslipidemia in obese mice and consequently can act to improve cardiovascular function and prevent cardiovascular disease.

Example 12

Punicalagin, Ellagic Acid, and Urolithin A Improve Glucose Tolerance in Obese Mice Male C57BL6/J mice were grouped and treated as described in Example 7. In addition, glucose tolerance test (GTT) was performed for HFD-fed mice which developed glucose intolerance. Glucose tolerance test was monitored 10 weeks after the initiation of the treatment by Oral Glucose Tolerance Test (oGTT). Animals were fasted for 12 h (from 8 pm to 8 am) before oGTT. The day of the oGTT, a small drop of blood (<2 µL) was collected from the lateral tail vein and glycemia was monitored using a glucometer (AccuCheck Aviva, Roche Diagnosis). Each animal then received, at time 0, an oral dose of D-glucose at a dosing of 2 g/kg body weight. Glycemia was then monitored at times 15, 30, 45, 60, 90, 120, and 150 min after oral glucose load.

As in humans, high fat diet feeding in mice resulted in the onset of obesity and type 2 diabetes which is characterized by a severe glucose intolerance as assessed by the follow-up of glycemia immediately following an exposure to glucose (2 g/kg of body weight) (Glucose tolerance test) (FIG. 24A and FIG. 24B). As depicted FIG. 24A and FIG. 24B, punicalagin, ellagic acid, and urolithin A treatment improved glucose tolerance in HFD-fed mice. Consequently, these treatments may also be effective therapeutic approaches for the treatment of type 2 diabetes.

Example 13

Urolithin a Increases Mitochondrial Function in Aged *C. elegans*

*C. elegans* strains were cultured at 20° C. on nematode growth media (NGM) agar plates seeded with *E. coli* strain OP50. Strain used was wild-type Bristol N2 provided by the Caenorhabditis Genetics Center (University of Minnesota). Urolithin A was dissolved in DMSO. Animals were exposed to compounds from eggs on plates seeded with live OP50 bacteria. Control plates were prepared with the corresponding concentration of DMSO (0.1%).

Measurement of oxygen consumption is a direct indicator of mitochondrial activity. The effect of urolithin A on mitochondrial activity in aged *C. elegans* (10 days old) was assessed by treating *C. elegans* with urolithin A for 10 days of adulthood, at which time oxygen consumption was measured using the Seahorse XF24 equipment (Seahorse Bioscience Inc., North Billerica, Mass.). 250 ten-day-old *C. elegans* were used per condition. *C. elegans* were recovered from NGM plates with M9 medium, washed three times in 2 mL M9 to eliminate residual bacteria, and resuspended in 500 µL M9 medium. Worms were transferred into 24-well standard Seahorse plates (#100777-004) (50 worms per well) and oxygen consumption was measured. The basal oxygen consumption of the worms was first measured over 30 minutes at 5 minute intervals (0 min, 5 min, 15 min, 20 min, 25 min and 30 min) with 5 replicates per interval. Respiration rates were normalized to the exact number of worms per well determined after the completion of the experiment using a stereomicroscope. After determining the basal oxygen consumption, uncoupled oxygen consumption was measured by adding carbonylcyanide-p-(trifluoromethoxy) phenylhydrazone (FCCP) at the 30 minute time point to the media in order assess the maximal oxygen consumption capacity and maximal mitochondrial capacity. Uncoupled oxygen consumption was measured at 5 minute intervals (35 min, 40 min, 45 min, 50 min, 55 min and 60 min) to permit measuring the mitochondrial function over time. FCCP is a chemical uncoupling agent that abolishes the obligatory linkage between the respiratory chain and the phosphorylation system which is observed with intact mitochondria. This effect is due to the amphipathic properties of the molecule which dissolves in mitochondrial phospholipid bilayers. This dramatically increases ionic permeability of the mitochondrial membrane and generates dramatic proton leak leading to increase in oxygen consumption due to the quenching by oxygen of the electrons pumped into the respiratory chain in parallel to the proton leak. Since this oxygen consumption is dissociated (uncoupled) to ATP production (oxidative phosphorylation), FCCP increases oxygen consumption while decreasing the generation of energy (ATP) by the mitochondria. Fully uncoupled mitochondria, as achieved with FCCP, display the maximal capacity of their mitochondrial respiratory chain (maximal oxygen consumption) without the "brake" that oxidative phosphorylation and energy production represents).

The results depicted in FIG. 25A illustrate that urolithin A increases the maximal mitochondrial capacity of aged *C. elegans*, as depicted by a prolonged effect on increased uncoupled respiration in worms treated with urolithin A versus control (DMSO) treated worms. Control, untreated worms showed a brief increase in uncoupled respiration which quickly returned to basal levels of oxygen consumption. Urolithin A-treated worms showed a more extended elevation in oxygen consumption. The extent of enhanced mitochondrial activity is shown by comparing the area under the curves (AUC) during the decoupling period with the average coupled respiration employed as the baseline. It was observed that urolithin A significantly increased uncoupled respiration in aged worms as compared to control untreated worms over the 30 minute period evaluated.

Example 14

Urolithin A Increases Mitochondrial Activity in *C. elegans*

*C. elegans* strains were cultured at 20° C. on nematode growth media agar plates seeded with HT115 bacteria and containing 50 µM urolithin A or a corresponding concentration of DMSO as a control. The worms were treated for 24 hours. The strains used were the SJ4103 (zcIs14[myo-3::GFP(mit)]), which is a stable transgenic line expressing a mitochondrially localized green fluorescent protein (GFP) with a cleavable mitochondrial import signal peptide under the control of the specific body wall muscle promoter myo-3. GFP expression and quantification was carried out according to the protocol previously described (Durieux et al., 2011). Worms were treated with 50 µM urolithin A from eggs, and GFP was monitored after one day of adulthood. Fluorimetric assays were performed using a Victor X4 multilabel plate reader (Perkin-Elmer Life Science). Eighty worms were picked at random (20 worms per well of a black-walled 96-well plate) and each well was read four times and averaged.

The results in FIG. 26 show that treatment of worms with urolithin A induced the expression of the mitochondrial GFP-reporter driven by the muscle-specific myo-3 promoter in C. elegans. This striking increase in GFP expression provides clear evidence that mitochondrial capacity increased due to the urolithin A. To permit such an increase in observed GFP signal, mitochondria in muscle must either be enlarged or more numerous in these worms.

Example 15

Effects of Pomegranate-Derived Compounds on Mood and Cognition in Response to Chronic Stress 7-week-old C57BL/6J wild-type male mice were exposed to chronic unpredictable stress for a period of four weeks. Several behavioral experiments were carried out before, during, and after the chronic stress period to determine the impact on mood and cognition. As has been previously been reported, chronic stress negatively impacts mood and cognition. Natural compounds derived from pomegranate were administered to these mice to determine what impact these compounds would have on ameliorating this negative impact on mood and cognition.

Mice were habituated to our animal facility for 9 days before beginning the experiments. All mice were housed in groups of three in standard plastic cages, and they were kept under a 12 h light/dark cycle (7:00 a.m.-7:00 p.m.) with ad libitum access to food and water. All the procedures carried out were performed in accordance with the Swiss National Institutional Guidelines on Animal Experimentation and were approved by the Swiss Cantonal Veterinary Office Committee for Animal Experimentation.
Characterization of Animals After adaptation to the animal facility, all mice were characterized in terms of body weight, anxiety-like behavior in the elevated zero maze (EZM), and locomotion and exploration in the open field and novel object assays. The objective of these experiments was to match animals according to their anxiety and exploration rates in order to establish experimental and control groups that are equivalent according to these traits.
Elevated Zero Maze Anxiety was measured in an elevated zero maze (EZM). Mice were observed for 5 min in the EZM (a 5.5-cm-wide annular runway with a diameter of 46 cm and raised 46 cm above the ground) under dim and dispersed light conditions. Two opposing 90° sectors were protected by 13.5 cm high inner and outer walls. Thus, three zones were defined as follows: an intermediate zone comprising four 30° segments at the ends of the protection walls separated by the two 50° wide closed/protected and the two 70° wide open/unprotected exploration zones. With these boundaries, the entries into the open sectors were detected only when the animal entered into them with all four paws. The trajectories of each mouse were automatically recorded by video tracking (Ethovision 3.0, Noldus, Wageningen, Netherlands). The total number of entries into all the sectors served as an indicator of spontaneous locomotor activity, while differences in the number of entries and the time spent in the open sectors was taken as indicators of anxiety. Between sessions the maze was cleaned with 4% ethanol/water.
Open Field and Novel Object Locomotion and reactivity to an open field (OF) was assessed in a white quadratic box (50×50×37 cm) under dim and dispersed light conditions. The mouse is placed into the center of the field and allowed to move freely during 10 min. The total distance moved, frequency of entries to the center, time and percent time in the center of the OF were analyzed. Avoidance of the interior or "unprotected" area of the field is interpreted as an anxiety-like behavior. Measures of total distance are used as an index of activity. Exploratory behavior was assessed by using the novel object (NO) test. The NO test was performed immediately after the OF test. A small, metallic object (3×1.5×5 cm) was placed into the center of the open field while the mouse was inside. Mice were given then 5 min to freely explore the novel object. The time spent in the center and the periphery of the compartment, number and latency of entries to the center, and total distance moved in the center and the whole compartment were analyzed. Percent time and distance the mice spent in the center, exploring the novel object, were considered as indicators of "focused" exploratory activity.
Treatment with Pomegranate-Derived Extract Three weeks before the initiation of the chronic stress protocol mice were separated into four different groups. One group received standard mouse chow diet (Control), while the remaining three groups received varying doses of extract 1011, an extract derived from pomegranate juice. Low dose corresponded to an extract dose of 21 mg/kg/d of gallic acid equivalents of polyphenols (GAE PPE), the medium dose corresponded to an extract dose of 43 mg/kg/d of GAE PPE, the high dose corresponded to an extract dose of 86 mg/kg/d of GAE PPE (see Table 5).

TABLE 5

Pomegranate Powder Extract 1011.

| Extract 1011 | Polyphenols | Punicalagin | Punicalin | Ellagic Acid |
|---|---|---|---|---|
| Low Dose | 21 mg/kg/d | 2.1 mg/kg/d | 5.2 mg/kg/d | 2.0 mg/kg/d |
| Medium Dose | 43 mg/kg/d | 4.2 mg/kg/d | 10.5 mg/kg/d | 3.9 mg/kg/d |
| High Dose | 86 mg/kg/d | 8.5 mg/kg/d | 21 mg/kg/d | 7.8 mg/kg/d |

Treatment with the diet began three weeks before the initiation of the chronic stress protocol and continued until the termination of the experiment.
Treatment with Urolithin A, a Pomegranate-Derived Metabolite Three weeks before the initiation of the chronic stress protocol, mice were separated into two groups. One group received standard mouse chow diet (Control), while the other group received a diet containing urolithin A, delivered at a dose of 25 mg/kg/d.
Chronic Unpredictable Stress The unpredictable chronic stress protocol involved exposing animals to a daily stressful situation at an unpredictable moment for 4 weeks (between 8 am and 4 pm, and randomly distributed over the 28 days). The stress stimuli used were either: 6 min tail suspension; 3×0.4 mA inescapable footshock; 4 h exposure to soiled, damp sawdust; 2 h exposure on an elevated platform; 1 h immobilization in a plastic tube; 30 min exposure to 16° C.; 2 days inversed light/dark cycle; 10 min exposure to an older, aggressive conspecific; intense light exposure (600 lux); 2 h overcrowded cage (6 mice) and 8 h with a 40° cage inclination. All animals were weighed and the state of their coat was evaluated on a regular basis (every 3-5 days). During this experiment one group of mice was exposed to the chronic stress and the other group of animals was left undisturbed and served as controls.

Behavioral Assays

Tail Suspension Test

The tail suspension test (TST) is used as a model for assessing antidepressant-like activity in mice. The test is based on the fact that animals subjected to the short-term (6 min.), inescapable stress of being suspended by their tail, will develop an immobile posture. The mouse was hung on a metal bar by an adhesive tape placed 20 mm from the extremity of its tail. The distance between the floor and the bar was approximately 25 cm. Immobility is defined as the absence of initiated movements and includes passive swaying. Investigation time, which included immobility, struggling and climbing, was scored from videotape.

As shown in FIG. 27, chronic stress resulted in an increased immobility in the TST, an indicator of increased depression and sense of helplessness. However, mice treated with increasing doses of pomegranate extract demonstrated a reversal in this pattern and a restoration of mobility and struggling to levels observed in non-stressed mice. Thus the pomegranate extract prevents the depression response observed in chronically stressed non-treated mice.

Contextual Recognition

Contextual fear conditioning is a measurement of an animal's ability to remember a particular context. In this assay, mice are placed in a box and then receive two mild shocks, one minute apart. In reaction to the shocks mice freeze. The ability of mice to recognize the context in which they received the shock is tested by placing them back in the box at a later timepoint. If they recognize the context, mice will freeze in anticipation of receiving a shock.

In normal mice, the ability to recognize the context in the absence of any shocks is a measurement of contextual memory. Mice with better contextual memory recognize the initial context better and thus have a higher level of freezing.

This assay can also be used to measure anxiety in stressed mice. In stressed mice, increased anxiousness could be observed in increased freezing reaction time in response to the initial shocks, as well as a longer extinction period for the memory of the context. Extinction of the contextual memory is measured by placing the mouse in the same context once a day for several days in the absence of the initial adverse stimulus. With time mice unlearn the association of the context with the adverse stimulus, which is evidenced by a gradual decrease in freezing. In stressed mice that are anxious this extinction of the adverse memory takes longer.

Contextual fear conditioning was used to test the effect of pomegranate extract on anxiety induction (i.e., learned anxiety) in mice in response to contextual recognition. Training and testing took place in a rodent conditioning chamber (20×20×28 cm), placed into a plexiglass box and illuminated by a 20-W bulb. The side walls of the conditioning chamber were constructed of white methacrylate, and the door and the top cover were constructed of plexiglass. The floor consisted of 20 steel rods through which a scrambled shock from a shock generator could be delivered. Ventilation fans provided a background noise of 68 dB (whole system: Panlab, S. L., Barcelona, Spain). Fear conditioning to the context was performed during the third week of the chronic stress protocol in the stressed group. On the day of fear conditioning, mice were transported from the colony room to the adjacent behavioral laboratory and placed in the conditioning chamber. Training consisted of exposure of the mice to a conditioning context for 3 min followed by three electric foot-shocks (2 sec, 0.4 mA) delivered after every min. After the last foot-shock the animal stayed for 30 s in the chamber. The fear conditioning chamber was thoroughly cleaned with 0.5% acetic acid before each mouse was placed into the box. To determine the effect of chronic stress and the various doses of pomegranate extract on the level of anxiety induced by this contextual memory, the level of anxiety-induced behavior in response to this context was measured. The following behavioral responses, known to be sensitive to levels of anxiety, were examined: % freezing, % rearing, and % grooming. These behavioral measurements were performed 48 h later after re-exposing the mice to the conditioning context for 8 min. After training and testing sessions, animals were immediately returned to their home cages. Animals' behavior was recorded and later scored with in-house-made behavior observation software by an observer blind to the treatment of the animals.

Freezing, defined as a lack of movement except for heart beat and respiration, was scored and used as an index of anxiety. Freezing time was transformed to percentage freezing levels. Pomegranate extract showed a dose-dependent response, with a significant reduction in the % freezing at the highest dose (FIG. 28), indicating a protection against anxiety. Similar reduction in anxiety behavior is seen in rearing, with a significant and dose dependent protection of the rearing behavior upon administration of pomegranate extract (FIG. 29). Completing these observations is the strong suppression of anxiety-induced inhibition of grooming by the highest dose of pomegranate extract (FIG. 30). These results demonstrate that the pomegranate extract and compounds reduced experience-induced anxiety in mice.

This decrease in experience-induced anxiety in chronically stressed mice was also observed for urolithin A, a metabolite of punicalagin. In this study, levels of anxiety were measured by the extinction of memory of the adverse context provided in the contextual fear assay described above. In this study the mice that have undergone training using the contextual fear paradigm are exposed to this context daily for four days but in the absence of any adverse stimulus. The ability to recognize the context is measured by freezing during a period of 3 minutes of observation. Increased levels of anxiety have been shown to lead to a longer period for extinction for the memory of an adverse context. As shown in FIG. 31, mice that have undergone chronic stress showed a slower period of extinction than normal mice. However, upon treatment with urolithin A at a dose of 25 mg/kg/d, mice that had undergone chronic stress showed a significant improvement in adverse memory extinction, demonstrating that urolithin A, like punicalagin, is able to reduce anxiety in mice that have undergone chronic stress.

Morris Water Maze

Spatial memory and learning is affected by chronic stress. The Morris water maze apparatus consisted of a large white circular pool (140 cm diameter) filled with opaque colored water (25° C.+/−1° C.) and with a platform (10×10 cm$^2$) submerged 1 cm under the water surface. The water maze is surrounded by gray curtains (25 cm from the pool periphery) containing several prominent visual cues. Before testing the mouse is trained to learn the location of the platform. Utilizing the prominent visual cues, the mouse learns to locate the platform. The learning phase begins with a habituation phase in which mice are introduced to the room, apparatus, and the water by giving them a 2-min free swim trial with no platform present. Data is collected using a video camera fixed to the ceiling, connected to a video tracking system (Ethovision 3.0, Noldus, Wageningen, Netherlands).

Following a habituation session (day 0), mice were submitted to different protocols to sequentially assess their spatial learning abilities (days 1-3). Spatial learning sessions were conducted on three consecutive days (days 1-3), performing four trials per day with an inter-trial interval (ITI) of 6 min between each trial.

Each trial started by introducing the mouse into the maze with the aid of a cup, facing the pool wall, and at one of four possible positions that were randomly balanced between trials and days. The distance between the mouse and the platform was measured at each sampling time, with 25 sampling times collected per second. These distances were then summed for the 60 second period, to give a measurement of the distance to platform (cm) for each trial. If a mouse did not find the platform within 60 sec, it was gently guided toward it. Each mouse had to remain on the platform for 20 sec before it was returned into its waiting cage.

The results of this example demonstrated that chronic stress had a significant negative impact on learning and spatial memory. During the training session there was a significant increase in the distance travelled to reach the platform compared with non-stressed control, showing that chronic stress impairs the normal memory forming during learning (FIG. 32). Treatment of mice with pomegranate extract was able to protect against these negative effects of chronic stress on learning and associated memory. A dose-dependent effect was observed in mice receiving the pomegranate extract, and treated, chronically stressed mice were able to perform at the same levels of non-stressed controls (FIG. 33).

A similar effect was observed for mice treated with urolithin A, as shown in FIG. 34. Mice having undergone the chronic stress protocol showed erratic learning, as evidenced by the high variability between sequential trials. Treatment of chronically stressed mice with urolithin A at a dose of 25 mg/kg/d showed a stabilization of this variability. This highlights the fact that urolithin A, a downstream metabolite of punicalagin, is also able to protect against these negative effects of chronic stress on cognition, including learning and memory.

In summary, these results together demonstrate that pomegranate extract and derived compounds such as urolithin A are able to act to reduce the negative impacts of chronic stress on cognition, including memory and learning. Additionally, the pomegranate extract and derived compounds have anti-depressive activity as seen in the tail suspension test, and decrease anxiety caused by chronic stress. The results also demonstrate that pomegranate extract prevents the deterioration of memory and learning performance and spatial recognition normally observed following chronic stress.

Example 16

Effect on Memory and Cognition in the Aged Rat Model

During aging there are several effects on cognition and memory, which can be recapitulated in the rat model of aging. For a review see Gallagher and Rapp (1977) *Annu Rev Psychol.* 48:339-70. The aged rat model has been extensively used to characterize the effects of aging on memory and cognition. In the experiments presented here, improved performance was observed in the presence of pomegranate extract.

Aged Sprague-Dawley rats (beginning at 19 months old) received pomegranate extract (1108) in their drinking water, at a concentration of 0.34 mg/mL polyphenols (PPE). Polyphenols content were measured using the Folin-Ciocalteu spectrophotometric method, with the phenolic content expressed as gallic acid equivalents. Control treatment consisted of 1.36% sucrose, 0.12% D-glucose, and 0.12% D-fructose dissolved in water. The rats on average consumed 30 mL/day of both the control and 1108 treatments (see Table 6), with an average weight of 660 g/rat. This resulted in a dose of 15 mg PPE/kg/d or 1.1 mg punicalagin/kg/d for animals receiving the 1108 extract.

TABLE 6

Pomegranate liquid extract.

|  | Extract 1108 |
| --- | --- |
| Polyphenols dose delivered | 15 mg/kg/d |
| Punicalagin dose delivered | 1.11 mg/kg/d |

After 2.5 months of treatment, short term working memory was evaluated using a social recognition task, a standard test involving social cognition. Thor and Halloway (1981) *Animal Learning Behavior.* 9:561-5. In this task, each aged rat was placed in its home cage together with a juvenile male Sprague-Dawley rat (<5 weeks old) for 5 minutes. Thirty minutes later, the same exact procedure was repeated with the same juvenile to determine a second time the degree of interaction between the two animals. Less contact is expected in the second interaction, as the two animals have had a previous interaction. This decrease in contact between the animals is a measure of cognitive performance and memory retention. Thirty minutes later, a novel juvenile rat was placed for 5 minutes together with the aged rat, in order to measure whether the animal can discriminate between the two different juvenile individuals. During each period of contact between the two animals, the total time of contact was measured to assess the intensity of social interaction.

Results are shown in FIG. 35. Control-treated aged animals showed no preference for the familiar object and spent equal time exploring both objects, an effect that has been previously shown in aged rats and thought to reflect a decline in temporal order memory during aging. Hauser et al. (2009) *Behav Neurosci.* 123:1339-45. However, rats treated with extract 1108 showed a decrease in the time spent with the same juvenile during the second exposure period, as well as an increase in the time of interaction with a novel juvenile rat. This observed difference illustrates the protective benefit of extract 1108 on memory development and retention.

Example 17

Effect on Spatial Memory in Aged Rat Model

Spatial memory also has been reported to be affected by aging, with a decline in performance resulting from aging. Bergado et al. (e-pub Oct. 29, 2010) Spatial and emotional memory in aged rats: a behavioral analysis. Neuroscience. To examine the effects of pomegranate extract on spatial memory decline during aging, aged Sprague-Dawley rats (beginning at 19 months old) were treated with pomegranate extract 1108 or control in their drinking water as described for Example 16.

Aged rats were treated with the extract 1108 or an isocaloric control for three months, after which their learning and memory performance were evaluated using the Morris water maze task, described in Example 15.

The learning abilities of each animal were evaluated through their performance on the reversal task (three trials). In this task the animals were first taught the location of the platform in quadrant (WEST) through three training trials. The location of the platform is then changed and it is placed in the opposite quadrant (EAST). The animals underwent three new training sessions to learn the new location of the platform. The effort to determine the new location of the platform, as measured by the distance traveled before locating the platform, was measured. Results are shown in FIG. 36. Animals treated with the extract were significantly more efficient at localizing the platform in the reversal test (one-way ANOVA, P<0.02; control N=11; PJ: N=13; extract: N=14), demonstrating a therapeutic benefit of the administered extract for this aspect of spatial memory.

Example 18

Effects of Pomegranate-Derived Compounds on Spatial and Working Memory in Alzheimer's Disease Alzheimer's Disease (AD) has been shown to have detrimental effects on spatial memory, an effect that is also observed in AD mouse models of the disease. To determine the effects of pomegranate-derived compounds on ameliorating spatial and working memory in AD, various pomegranate extracts and punicalagin were tested in two behavioral assays of spatial memory, the Y maze and the Morris water maze.

Y Maze

In this study, the 5XFAD mouse model of AD was utilized. The 5XFAD mouse model for Alzheimer's disease is based on genetic modifications (introduction of the mutated human APP and PS1 genes) leading to the production of amyloid β peptide (A(β)) in brain tissue. These mice were found to have a significant decline in cognitive performance in the Y maze as early as 7 months of age.

To determine the effect of pomegranate-derived compounds, a pomegranate extract (PE) derived from whole pomegranate was delivered by gavage at a dose of 60 mg/kg/d of polyphenols, which includes approximately 5.6 mg/kg/d of punicalagin. Mice were gavaged 3 times weekly beginning at 3 months of age until the end of treatment. Mice were tested after 7 months of age for the effects of PE on working memory on the Y maze. Mice were placed in the Y maze for 15 minutes and were allowed to explore two arms, the third arm being closed. Four hours later, the animal was placed again in the maze for five minutes, this time with the third arm open, allowing the mouse to have the possibility to explore freely all three arms. Exploration activity in the novel arm assessed the ability of the animal to recognize that this particular zone has not been explored yet, according to spatial clues. Mice were scored as making a correct alteration during exploration if they explored each of the three arms, and not just the first two presented.

As shown in FIG. 37, a significant improvement in working memory performance, as measured by the number of correct alterations, was observed in 5XFAD mice treated with PE.

Morris Water Maze

The pomegranate extracts 31008, 61109 and 71109 were tested in a second transgenic animal model of Alzheimer's disease expressing both the amyloid mutant London mutations and the prenisilin-1 human mutation. Animals in this model develop plaques by 4 months of age and memory deficits by 6 months. Dense plaque load is visible after 7 months.

In one set of experiments, four-month-old APP-PS1 transgenic mice were fed with a fixed dose of approximately 97 mg total polyphenols/kg/day, which includes approximately 15 mg/kg/d of punicalagin of the extract 31008, which was derived from whole pomegranate, via their drinking water. In one set of experiments, four-month-old APP-PS1 transgenic mice were fed with a fixed dose of approximately 468 mg total mg/kg/day of the extract 61109, which was highly enriched for punicalagin (>91%), via drinking water. In one set of experiments, four-month-old APP-PS1 transgenic mice were fed with a fixed dose of approximately 180 mg total polyphenols/kg/day of the extract 71109, which was derived from pomegranate husk, via drinking water. After 3 months of feeding, the mice (then 7 months old) were tested in the Morris water maze spatial test.

The Morris water maze was performed during days 84-87 of treatment. The pool (a white, circular vessel 1 m in diameter) contained water at 20° C. with titanium-dioxide as an odorless, nontoxic additive to hide the escape platform (1 cm beneath the water level). Swimming of each mouse was videotaped and analyzed (Ethovision, Noldus information Technology, Wageningen, Netherlands). Prior to training, each mouse was placed on top of the platform for 15 seconds. For place navigation tests, mice were trained to locate the hidden platform in five blocks of three trials over three consecutive days. Each trial consists of a forced swim test of maximum 120 seconds, followed by 60 seconds of rest. The time each mouse needed to locate the platform was measured during the five consecutive blocks of training to determine a learning curve for each mouse.

Twenty-four hours after the final training, each animal underwent a probe trial with the platform removed. Mice were allowed to search for the missing platform for 60 seconds and the search time spent in each quadrant of the pool, as well as the number of crossings of the original platform position was measured. As shown in FIG. 38, the mice fed with Extract 31008 showed an increase performance in the probe test as demonstrated by the increased frequency of crossings of the area were the platform was formally located. Mice fed with extracts 61109 and 71109 had even better performance.

The compositions of the extracts 61109 used in this experiment are shown in Table 7.

TABLE 7

| | Extract 61109 |
| --- | --- |
| Punicalagin | 91.3% (w/w) |
| Punicalagin dose delivered | 295 mg/kg/d |

Example 19

Effects of Pomegranate-Derived Compounds on Depression, Anxiety and Cognition in Response to Early-Life Stress Pomegranate-derived compounds were assessed for their ability to improve brain functions, including cognition, depression and anxiety, in an early-life stress model associated with maternal separation.

Early life stress has a significant impact on cognitive performance in later adult life, including (i) increasing abnormal decision making and excessive risk-taking; (ii) susceptibility to increased rates of depression and anxiety; and (iii) impaired learning and memory.

All procedures carried out were performed in accordance with the Swiss National Institutional Guidelines on Animal Experimentation and were approved by the Swiss Cantonal Veterinary Office Committee for Animal Experimentation.

Early Life Stress Produced by Maternal Separation

At postnatal day 1, pups were culled to have 6 pups per mother. From postnatal day 1 to 14, unpredictable maternal separation (MS) of a period of 3 hours daily was carried out. Maternal separation was performed at random times (from 8 am to 2 pm) to avoid the habituation of the mother to the procedure. The protocol consisted of removing pups from their mother to another cage at room temperature for a 3 hour period, after which the pups were returned to their original nest. These groups are denoted as early-life stress in the figures. A control group of dam/pups was left undisturbed and is denoted in the figures as normal.

Treatment with Punicalagin Isolated from the Pomegranate

One week after maternal separation mice were separated into two groups. One control group received the standard mouse chow diet (Untreated), while the other group received the ellagitannin punicalagin admixed into the food and designed to deliver a dose of 90 mg/kg/day to the mice. Treatment with the diet began 1 week after the termination of the maternal separation treatment.

Behavioral Assays

The effects of early-life stress on depression, anxiety and cognition were examined utilizing the following behavioral assays which were carried out 166 days after the completion of the maternal separation protocol. Normally raised mice were compared versus maternally separated mice (early-life stress) and maternally separated mice treated with punicalagin.

Dark/Light Box Test

In this assay mice are placed in a PVC box which is separated into two compartments: a dark compartment (15× 20×25 cm, black PVC, and covered above) and a lit compartment (30×20×25 cm, white PVC and illuminated at 200 lux), both linked by an interconnecting door (5×5 cm) (Ligna, Paris, France). The experiment is started by placing the animal in the dark compartment, after which a camera records for a 5 minute period the amount of time the mouse spends in the lit area, the number of transitions from the dark to lit area, and the latency to escape from dark to lit area.

Normally, mice will avoid the illuminated area in the box. Maternally separated mice spent an abnormally long time in the illuminated compartment as compared to their non-maternally separated littermates as a consequence of their early-life stress (FIG. 39). This increase in time spent exploring the lit area reflects an impaired decision-making behavior characterized by abnormal and excessive risk-taking.

Punicalagin treatment of maternally separated mice reversed and normalized the excessive risk-taking behavior observed and restored the decision making process to normal (FIG. 39).

Elevated O-Maze (EOM)

Another behavioral assay that measures abnormal risk taking is the elevated O maze (EOM). In this assay an apparatus consisting of a ring with a diameter of 41.5/46.5 cm (internal/external diameter) is divided into four equal parts. Two parts of the ring, opposite each other, are enclosed by walls that are 5 cm high. The remaining two parts of the ring have no walls. The maze is elevated 1 m above the floor. The natural tendency of mice is to avoid open surfaces and spend more time in the enclosed regions of the ring that have the 5 cm walls, as opposed to the open regions of the ring.

To examine the effect of early life stress, mice were placed at the entrance of one of the areas of the maze with the 5 cm walls, with the nose facing the closed arm, and were allowed to explore the EOM for 5 min. During this period animal behavior was videotaped. The time spent in each arm (closed versus open) was calculated, with an entry into the arm only being considered to have occurred when the animal placed all four paws in the arm.

Normally, mice placed in the elevated O-maze will avoid the open regions of the ring and spend limited time exploring this area. Mice stressed by maternal separation spent an abnormally long time in the open sections of the O-maze as compared to their non-stressed littermates (FIG. 40). As also observed in the dark/light box test, this reflects an impaired decision-making behavior in early-life stressed mice which is characterized by abnormal and excessive risk-taking.

Punicalagin treatment of maternally separated mice reversed and normalized their abnormal excessive risk taking behaviour due to early-life stress (FIG. 40).

Forced Swim Test

The Porsolt or Forced Swim Test is commonly used to test antidepressant treatments (Porsolt et al., 1977a; Porsolt et al., 1977b). For this behavioral test, a mouse is placed in a 5 L cylinder (11 cm diameter and 25 cm height) filled two-thirds full with water at 23° C.

Animals were considered to be engaged in swimming and mobile if there was a clear displacement of the body. Animals floating with minimal movement during the analysis period were considered to be immobile. Animal behavior was recorded over a 6-minute test period using a camera and a mirror behind the cylinder. The first 2 minutes and the last 4 minutes of the swimming were analyzed separately for mouse swimming activity. Increasing level of depression is correlated to an increase in mouse immobility, particularly during the last 4 minutes. Animals that have undergone early-life stress showed a significant increase in immobility as compared to their non-stressed littermates, indicating an elevated level of depression (FIG. 41). Punicalagin treatment of early-life stressed mice reversed this abnormal behavior (increased immobility) and increased swimming activity to levels seen in non-stressed mice. This behavioral effect of punicalagin demonstrates its activity as an anti-depressant (FIG. 41).

Contextual Fear Conditioning

Contextual fear conditioning was used to determine the effects of the ellagitannin punicalagin on the susceptibility of adult animals, subjected to early life stress, to anxiety. Animals were trained in a fear conditioning chamber (Context A, W×L×H: 30 cm×24 cm×26 cm) (PanLab) that contained a grid floor with stainless steel rods and was connected to a shock generator developed by Panlab. During training, animals were placed into the chamber one at a time. After four minutes of exploration inside the chamber, one foot shock (2 seconds and 0.4 mA) was administered, followed by a second foot shock (2 seconds and 0.4 mA) one minute later. Thirty seconds after the second foot shock, the mouse was placed back into its home cage. Animal behavior was monitored every 2 seconds throughout the duration of the experiment. The period that mice spent immobile in the chamber was considered as "freezing" and was scored throughout these periods. The time the mice spent immobile after the first shock was recorded for a 60 second period and expressed as a percentage.

The behavior of mice to rest immobile and "freeze" in response to a foot shock is a measure of their level of anxiety. The longer the duration the "freezing" lasts during this behavioral test, the higher the animals' level of anxiety.

Differences in freezing between the groups tested (normal non-stressed, early-life stress, and early-life stress+punicalagin) were observed after the first shock (FIG. 42). Early-life stress led to increased anxiety in mice as evidenced by the increased time spent freezing following the foot shock, as compared to their non-stressed littermates (FIG. 42). Punicalagin treatment decreased and normalized these elevated anxiety levels resulting from early-life stress, as shown by a reduced freezing time following the foot shock (FIG. 42). These observations in the early-stress model illustrate the anxiolytic effects of punicalagin.

The increased anxiety experienced by animals exposed to early life stress is also observed in the extinction (i.e., disappearance) of the contextual memory (i.e., the memory associating the context of the environment to the shock) induced by this assay. To examine the strength of the anxiety developed during the contextual fear conditioning (as described above), animals were placed into the same chamber and context for 3 min daily (same time of day, however no shock this time) for the 12 days that followed the initial testing. Freezing behavior induced by the simple recognition by the animals of the chamber, where they received the initial shock, was measured during each of these daily 3-minute periods.

Animal groups (normal non-stressed, early-life stress, and early-life stress+punicalagin) showed differences in the decline of their contextual recall of the shock over the subsequent 12 days (FIG. 43). In this graph, the duration of freezing is presented as the percent of time spent immobile on day 1 (for example, if a mouse was immobile for 60 seconds on day 1 and 30 seconds on day 8, percent immobility is 100% on day 1 and is 50% on day 8).

Normal, non-stressed mice showed a predictable decline in contextual recall during the 12 day period (FIG. 43). Early-life stressed mice had a heightened contextual recall, which is illustrated by a higher level of freezing than their non-stressed littermates (FIG. 43). This shows a prolonged elevated level of anxiety in these maternally separated mice. Punicalagin treatment of early-life stressed mice had a clear impact on reducing anxiety as seen by the extinction of the contextual recall. Treated early-life stressed mice showed a faster extinction than untreated early-life stressed mice, characterized by reduced period of time spent freezing between days 8 and 12 (FIG. 43).

Rotarod

To measure the effects of pomegranate-derived compounds on the negative cognitive impacts of maternal separation, effects on motor learning were assayed using the rotarod behavioral assay. The rotarod apparatus consists of a rod of 2 cm diameter. A mouse is placed on a rotating rod which is started at an initial speed of 5 rpm. The rod speed is gradually accelerated at a rate of 8 rpm/min until reaching a speed of 45 rpm. The latency to fall was measured with a cutoff time of 300 sec. As shown in FIG. 44, mice that have undergone early-life stress suffered from impaired motor learning. Maternally separated mice fell off the rotarod faster than normal non-stressed mice. Treatment with punicalagin restored motor learning skills in early-life stressed animals to performance levels observed in normal non-stressed littermates.

Morris Water Maze

The Morris water maze behavioral assay was employed to assess the cognitive impact of maternal separation. In this assay, cognitive learning is measured by the ability of a mouse to locate a hidden platform in a pool of opaque water. The apparatus consists of a pool (140 cm diameter) filled with water at 22° C. Mice escape from the water by swimming to a hidden circular platform (15 cm diameter) placed 1 cm under the surface of the water. By using visual cues located outside of the maze, mice are able to locate the platform and recall its location during subsequent trials. During the training phase, mice were placed at two starting positions (alternating) every hour. The Morris water maze task was performed with 8 trials at T1, 6 trials at T2, and 4 trials at T3 (on days 1, 2 and 3). Mice had a maximum of 60 sec to reach the platform. Escape latency to reach the platform was measured by a video tracking system. As can be observed in FIG. 45, early-life stress had a significant impact on cognitive learning, with mice taking a longer period of time to learn the location of the hidden platform, as shown by the increased escape latency versus normal non-stressed mice. Treatment of these maternally-separated mice with punicalagin reversed this negative impact of early-life stress, reducing the time to learn the location of the hidden platform to levels observed in normal non-stressed mice. These results demonstrate the ability of punicalagin to reverse the long-term negative cognitive impacts of early-life stress on learning and memory formation.

Pomegranate-Derived Compounds

Taken together the data above demonstrate that compounds derived from ellagitannins are able to reverse to long-term negative impact of early-life separation on depression, anxiety, and cognition.

Example 20

Effects of Pomegranate-Derived Compounds on Memory and Cognition in Normal Mice

Treatment with Pomegranate-Derived Compounds

Beginning at 3 months of age, mice were either fed (i) a standard control diet such as AIN-93G; (ii) a diet containing punicalagin at a concentration of 0.87 mg/kg, so as to deliver an approximate dose of 90 mg/kg/day (for a period of 3 months); or (iii) a diet containing urolithin A at a concentration of 0.57 mg/kg, so as to deliver an approximate dose of 55 mg/kg/day (for a period of 2.5 months). Actual doses vary slightly depending on the food consumption of each individual mouse, as well as the weight of the mouse. Behavioral assessment of cognition was measured after this period.

Behavioral Assay to Measure Effects of Pomegranate-Derived Compounds on Cognition To examine the effect of pomegranate-derived compounds on memory and cognition, mice were examined for improvements in contextual memory utilizing the contextual fear conditioning assay. Mice were trained in a fear conditioning chamber as described in Example 19.

During training, animals were placed into the chamber one at a time. After four minutes of exploration inside the chamber, one foot shock (2 seconds and 0.4 mA) was administered, followed by a second foot shock (2 seconds and 0.4 mA) one minute later. Thirty seconds after the second foot shock, the mouse was placed back into its home cage.

One day later, trained animals were returned to the chamber for a period of three minutes. During this period mice were monitored for their movement. The amount of time spent immobile or "frozen" was scored as a percentage of the total time (3 minutes) under observation. The time spent immobile is a measure of the strength of the memory of the mice to recall the context in which they were trained. Treatment with both the pomegranate-derived ellagitannin punicalagin and the ellagic acid metabolite urolithin A led to significant improvements in contextual memory over untreated control mice as determined by their contextual memory 24 hours following the training period (FIG. 46).

To determine the effect of these pomegranate-derived compounds on memory retention, normal mice fed either (i) a control diet; (ii) punicalagin (for a period of 3 months) or (iii) urolithin A (for a period of 2.5 months) were studied for their memory recall on days 1, 2, 3, 4 and 5 after the initial contextual fear training.

Animals were placed in the same chamber and context for 3 min daily (same time of day, however no shock this time) for the 5 days that followed the initial testing. Freezing behavior induced by the simple contextual recognition by the animals of the chamber, where they received the initial shock, was measured during each of these daily 3-minute periods. The ability to recognize this environment in the absence of the stimulus is a measurement of contextual memory.

With each passing day control untreated mice begin to have an extinction of their memory for this contextual stimulus, as evidenced by a decrease in extent of freezing (FIG. 47). Mice treated with either punicalagin or urolithin A demonstrated an improved memory retention as compared to control, untreated mice. This is illustrated by an ability to remember the initial context for a longer period, evidenced by a significantly longer period for the extinction of the contextual memory (FIG. 47).

These results demonstrate that treatment with either punicalagin or urolithin A lead to improved cognition, as evidenced by a significant increase in context recognition and improved memory retention.

Example 21

Effects of Pomegranate-Derived Compounds on Improving Muscle Performance in Normal Mice Ellagitannin-derived compounds punicalagin and urolithin A were evaluated for their ability to improve muscle performance. To examine the benefits of punicalagin and urolithin A on improving muscle performance, their effects were examined using two behavioral assays: (i) the rotarod assay, which measures muscle performance and motor skills, including coordination, and (ii) the treadmill endurance test, which measures muscle performance and endurance.

Behavioral Assays to Measure the Effects of Pomegranate-Derived Compounds on Muscle Performance Rotarod Assay Beginning at 3 months of age, mice were fed either a standard control diet such as AIN-93G or a diet containing punicalagin to deliver a dose of 90 mg/kg/day for a period of 3 months.

To examine the effect of pomegranate derived compounds on muscle performance and motor skills, mice were tested on the rotarod behavioral assay. The rotarod apparatus consists of a rod with a diameter of 2 cm with 5 compartments, 5 cm wide. A mouse is placed on a rotating rod which is started at an initial speed of 5 rpm. The rod speed is gradually accelerated at a rate of 8 rpm/min. The latency to fall was measured with a cutoff time of 300 seconds. Mice were tested for four trials. The latency to fall is a measure of the muscle performance and motor skills of the mice, with a better performance reflected by a longer latency to fall. Both control untreated and punicalagin-treated mice were tested. The ellagitannin punicalagin was able to significantly improve muscle performance and motor skills as compared to untreated mice. Punicaligin-treated mice were able to remain on the rotarod for a longer time and at higher speeds compared to untreated mice during sequential trial periods (FIG. 48).

Endurance Test

Normal 8-week-old mice were acclimated for 2 weeks prior to the start of the study. Mice were fed with a standard rodent diet (chow diet) or a diet containing urolithin A mixed with the food to reach a dosing of 55 mg/kg/day delivered to the mice. Following 6 weeks of treatment, mice were tested for their muscle performance by means of an endurance test.

An endurance test was performed using a variable speed belt treadmill enclosed in a plexiglass chamber with a stimulus device consisting of a shock grid attached to the rear of the belt (Panlab, Barcelona, Spain). Mice were run at 10 cm/sec and a 0° of incline for 5 min. Speed was then incremented by 2 cm/sec every 5 min, until mice were exhausted. The distance run and the number of shocks obtained over 5 min intervals were recorded. Mice were considered exhausted and removed from the experiment when they received approximately 20 shocks in a period of 1 min. Control untreated and urolithin A-treated mice were tested and compared for their performance.

Improved muscle performance and endurance is reflected by an ability to run at higher speeds on the treadmill. Mice will seek to avoid the shock and will run despite the increasing speed. At a certain point the mice are unable to keep up with the treadmill speed and are shocked. After reaching the threshold levels of shocks, mice are removed from the treadmill. Mice having better muscle performance and improved endurance will be able to keep up with the increasing speed of the treadmill and will experience fewer shocks at a particular speed. Urolithin A-treated mice ran at higher speeds than untreated control mice in this behavioral assay, illustrating that urolithin A improved muscle performance and endurance in this context (FIG. 49).

These results demonstrate that the ellagitannin punicalagin and its metabolite urolithin A are able to improve muscle performance and motor skills in mammals.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right physically to incorporate into this application any and all materials and information from any such articles, patents, patent applications, or other physical and electronic documents.

REFERENCES CITED

Bai, N., K. He, et al. (2008). "Active compounds from *Lagerstroemia speciosa*, insulin-like glucose uptake-stimulatory/inhibitory and adipocyte differentiation-inhibitory activities in 3T3-L1 cells." *J Agric Food Chem* 56(24): 11668-74.

Bishop, N. A., T. Lu, et al. (2010). "Neural mechanisms of ageing and cognitive decline." *Nature* 464(7288): 529-35.

Bloss, E. B., W. G. Janssen, et al. (2010). "Interactive effects of stress and aging on structural plasticity in the prefrontal cortex." *J Neurosci* 30(19): 6726-31.

Bowman, R. E., K. D. Beck, et al. (2003). "Chronic stress effects on memory: sex differences in performance and monoaminergic activity." Horm Behav 43(1): 48-59.

Cerda, B., J. C. Espin, et al. (2004). "The potent in vitro antioxidant ellagitannins from pomegranate juice are metabolised into bioavailable but poor antioxidant hydroxy-6H-dibenzopyran-6-one derivatives by the colonic microflora of healthy humans." *Eur J Nutr* 43(4): 205-20.

Cerda, B., P. Periago, et al. (2005). "Identification of urolithin A as a metabolite produced by human colon microflora from ellagic acid and related compounds." *J Agric Food Chem* 53(14): 5571-6.

De Souza Schmidt Goncalves, A. E., F. M. Lajolo, et al. "Chemical composition and antioxidant/antidiabetic potential of Brazilian native fruits and commercial frozen pulps." *J Agric Food Chem* 58(8): 4666-74.

Del Pozo-Insfran, D., C. H. Brenes, et al. (2004). "Phytochemical composition and pigment stability of Acai (*Euterpe oleracea* Mart)." *J Agric Food Chem* 52(6): 1539-45.

Dumitriu, D., J. Hao, et al. (2010). "Selective changes in thin spine density and morphology in monkey prefrontal cortex correlate with aging-related cognitive impairment." *J Neurosci* 30(22): 7507-15.

Gasperotti, M., D. Masuero, et al. "Profiling and accurate quantification of *Rubus ellagitannins* and ellagic acid conjugates using direct UPLC-Q-TOF HDMS and HPLC-DAD analysis." *J Agric Food Chem* 58(8): 4602-16.

Gil, M. I., F. A. Tomas-Barberan, et al. (2000). "Antioxidant activity of pomegranate juice and its relationship with phenolic composition and processing." *J Agric Food Chem* 48(10): 4581-9.

Greene, L. A. and A. S. Tischler (1976). "Establishment of a noradrenergic clonal line of rat adrenal pheochromocytoma cells which respond to nerve growth factor." *Proc Natl Acad Sci USA* 73(7): 2424-8.

Gunning, P. W., G. E. Landreth, et al. (1981). "Differential and synergistic actions of nerve growth factor and cyclic AMP in PC12 cells." *J Cell Biol* 89(2): 240-5.

Harper, M. E., K. Green, et al. (2008). "The efficiency of cellular energy transduction and its implications for obesity." *Annu Rev Nutr* 28: 13-33.

Hebert, L. E., P. A. Scherr, et al. (2003). "Alzheimer disease in the US population: prevalence estimates using the 2000 census." *Arch Neurol* 60(8): 1119-22.

Joels, M., Z. Pu, et al. (2006). "Learning under stress: how does it work?" *Trends Cogn Sci* 10(4): 152-8.

Joseph, J. A., B. Shukitt-Hale, et al. (2005). "Reversing the deleterious effects of aging on neuronal communication and behavior: beneficial properties of fruit polyphenolic compounds." *Am J Clin Nutr* 81(1 Suppl): 313S-316S.

Kujoth, G. C., A. Hiona, et al. (2005). "Mitochondrial DNA mutations, oxidative stress, and apoptosis in mammalian aging." *Science* 309(5733): 481-4.

Lee, J. H., J. V. Johnson, et al. (2005). "Identification of ellagic acid conjugates and other polyphenolics in muscadine grapes by HPLC-ESI-MS." *J Agric Food Chem* 53(15): 6003-10.

Maier, S. F. and L. R. Watkins (2005). "Stressor controllability and learned helplessness: the roles of the dorsal raphe nucleus, serotonin, and corticotropin-releasing factor." *Neurosci Biobehav Rev* 29(4-5): 829-41.

Puech, J. L., C. Mertz, et al. (1999). "Evolution of castalagin and vescalagin in ethanol solutions. Identification of new derivatives." *J Agric Food Chem* 47(5): 2060-6.

Pinnock, S. B. and J. Herbert (2001). "Corticosterone differentially modulates expression of corticotropin releasing factor and arginine vasopressin mRNA in the hypothalamic paraventricular nucleus following either acute or repeated restraint stress." *Eur J Neurosci* 13(3): 576-84.

Rea, S. L., N. Ventura, et al. (2007). "Relationship between mitochondrial electron transport chain dysfunction, development, and life extension in *Caenorhabditis elegans*." *PLoS Biol* 5(10): e259.

Roozendaal, B. (2003). "Systems mediating acute glucocorticoid effects on memory consolidation and retrieval." *Prog Neuropsychopharmacol Biol Psychiatry* 27(8): 1213-23.

Rozovsky, I., M. Wei, et al. (2005). "Reversible age impairments in neurite outgrowth by manipulations of astrocytic GFAP." *Neurobiol Aging* 26(5): 705-15.

Sandi, C. (2004). "Stress, cognitive impairment and cell adhesion molecules." *Nat Rev Neurosci* 5(12): 917-30.

Sandi, C. and M. Loscertales (1999). "Opposite effects on NCAM expression in the rat frontal cortex induced by acute vs. chronic corticosterone treatments." *Brain Res* 828(1-2): 127-34.

Sandi, C. and M. T. Pinelo-Nava (2007). "Stress and memory: behavioral effects and neurobiological mechanisms." *Neural Plast* 2007: 78970.

Satomi, H., K. Umemura, et al. (1993). "Carbonic anhydrase inhibitors from the pericarps of *Punica granatum* L." *Biol Pharm Bull* 16(8): 787-90.

Schriner, S. E., N. J. Linford, et al. (2005). "Extension of murine life span by overexpression of catalase targeted to mitochondria." *Science* 308(5730): 1909-11.

Shors, T. J. (2004). "Learning during stressful times." *Learn Mem* 11(2): 137-44.

Tanaka, K., G. Nonaka, et al. (1986). "Tannins and Related Compounds. XLI. 1) Isolation and Characterization of Novel Ellagitannins, Punicacorteins A, B, C, and Punigluconin from the brak of *Punica granatum* L." *Chem. Pharm. Bull* 34(2): 656-663.

Tanaka, K., G. Nonaka, et al. (1986). "Tannins and Related Compounds. XLI. 1) Isolation and Characterization of Novel Ellagitannins, Punicacorteins A, B, C, and Punigluconin from the brak of *Punica granatum* L." *Chem. Pharm. Bull* 34(2): 656-663.

Tanaka, K., G. Nonaka, et al. (1986). "Tannins and Related Compounds. XLI. 1). Revision of the Structures of Punicalin and Punicalagin, and Isolation and Characterization of 2-O-Galloylpunicalin from the Bark of *Punica granatum* L." *Chem. Pharm. Bull* 34(2): 650-655.

Trifunovic, A., A. Wredenberg, et al. (2004). "Premature ageing in mice expressing defective mitochondrial DNA polymerase." *Nature* 429(6990): 417-23.

Vrhovsek, U., A. Palchetti, et al. (2006). "Concentration and mean degree of polymerization of *Rubus ellagitannins* evaluated by optimized acid methanolysis." *J Agric Food Chem* 54(12): 4469-75. Wang, C. H., C. C. Wang, et al. (2010). "Mitochondrial dysfunction in insulin insensitivity: implication of mitochondrial role in type 2 diabetes." *Ann N Y Acad Sci* 1201: 157-65.

Xiao, J., A. Pradhan, et al. (2006). "Functional role of JNK in neuritogenesis of PC12-N1 cells." *Neurosci Lett* 392 (3): 231-4.

We claim:

1. A method of treating a neurodegenerative disease, comprising:
   administering to a subject in need thereof a therapeutically effective amount of urolithin A, thereby treating the neurodegenerative disease; wherein the effective amount of urolithin A is about 140 mg to about 8,400 mg; and the neurodegenerative disease is selected from the group consisting of AIDS dementia complex, Alzheimer's disease, dementia with Lewy bodies, Huntington's disease, and Parkinson's disease.

2. The method of claim 1, wherein the urolithin A is administered orally.

3. The method of claim 1, wherein the urolithin A is administered parenterally.

4. The method of claim 1, wherein the urolithin A is administered at least weekly.

5. The method of claim 1, wherein the urolithin A is administered at least daily.

6. The method of claim 1, wherein the neurodegenerative disease is selected from the group consisting of Alzheimer's disease, Huntington's disease, and Parkinson's disease.

7. The method of claim 1, wherein the neurodegenerative disease is Alzheimer's disease.

8. The method of claim 1, wherein the neurodegenerative disease is Parkinson's disease.

9. The method of claim 1, wherein the neurodegenerative disease is Huntington's disease.

10. The method of claim 1, wherein the subject is a human.

11. The method of claim 6, wherein the subject is a human.

12. The method of claim 7, wherein the subject is a human.

13. The method of claim 8, wherein the subject is a human.

14. The method of claim 9, wherein the subject is a human.

15. The method of claim 1, wherein the urolithin A is administered in the form of a pharmaceutical.

16. The method of claim 1, wherein the urolithin A is administered in the form of a medical food.

17. The method of claim 1, wherein the urolithin A is administered in the form of a functional food.

18. The method of claim 1, wherein the urolithin A is administered in the form of a food additive.

19. The method of claim 1, wherein the urolithin A is administered in the form of a dietary supplement.

20. The method of claim 1, wherein the urolithin A is administered in the form of a food product.

21. The method of claim 1, wherein the urolithin A is administered in the form of a nutritional supplement.

* * * * *